(12) United States Patent
Murthy et al.

(10) Patent No.: US 12,059,407 B2
(45) Date of Patent: Aug. 13, 2024

(54) COMPOSITIONS AND METHODS FOR DELIVERY OF MACROMOLECULES

(71) Applicants: The Regents of the University of California, Oakland, CA (US); Niren Murthy, Berkeley, CA (US); Joachim Justad Roeise, Berkeley, CA (US); Chung Hak Taing, Berkeley, CA (US)

(72) Inventors: Niren Murthy, Berkeley, CA (US); Joachim Justad Roeise, Berkeley, CA (US); Chung Hak Taing, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 795 days.

(21) Appl. No.: 16/766,226

(22) PCT Filed: Dec. 3, 2018

(86) PCT No.: PCT/US2018/063675
§ 371 (c)(1),
(2) Date: May 21, 2020

(87) PCT Pub. No.: WO2019/112965
PCT Pub. Date: Jun. 13, 2019

(65) Prior Publication Data
US 2020/0368206 A1    Nov. 26, 2020

Related U.S. Application Data

(60) Provisional application No. 62/594,319, filed on Dec. 4, 2017.

(51) Int. Cl.
| | | |
|---|---|---|
| A61K 31/4192 | (2006.01) | |
| A61K 31/192 | (2006.01) | |
| A61K 38/46 | (2006.01) | |
| A61K 47/61 | (2017.01) | |

(52) U.S. Cl.
CPC ........ *A61K 31/4192* (2013.01); *A61K 31/192* (2013.01); *A61K 38/465* (2013.01); *A61K 47/61* (2017.08)

(58) Field of Classification Search
CPC .................................................. A61K 31/4192
See application file for complete search history.

(56) References Cited

U.S. PATENT DOCUMENTS

| | | |
|---|---|---|
| 6,300,317 B1 | 10/2001 | Szoka, Jr. et al. |
| 7,056,901 B2 | 6/2006 | Frechet et al. |
| 2002/0072121 A1 | 6/2002 | Lam et al. |
| 2006/0222657 A1 | 10/2006 | Dowdy et al. |

OTHER PUBLICATIONS

Vippagunta et al. (2001).*
Alsaiari, et al.; "Endosomal Escape and Delivery of CRISPR/Cas9 Genome Editing Machinery Enabled by Nanoscale Zeolitic Imidazolate Framework"; JACS; vol. 140, pp. 143-146 (2018).
Dowdy; "Overcoming cellular barriers for RNA therapeutics"; Nature Biotechnology; vol. 35, No. 3, pp. 222-229 (Mar. 2017).
Kaczmarek, et al.; "Advances in the delivery of RNA therapeutics: from concept to clinical reality"; Genome Medicine; vol. 9, No. 60, 16 pages (2017).
Naka, et al.; "Molecular Harpoons. Membrane-Disruptive Surfactants That Can Recognize Osmotic Stress in Phospholipid Bilayers"; vol. 115, No. 6, pp. 2278-2286 (1993).
Sun, et al.; "Efficient Delivery of CRISPR-Cas9 for Genome Editing via Self-Assembled DNA Nanoclews**"; Angew Chem Int Ed Engl; vol. 54, No. 41, pp. 12029-12033 (Oct. 5, 2015).

* cited by examiner

*Primary Examiner* — Paul V Ward
(74) *Attorney, Agent, or Firm* — Rudy J. Ng; Paula A. Borden; Bozicevic, Field & Francis LLP

(57) ABSTRACT

The present disclosure provides endosomal disruptors, which are useful for facilitating delivery of a macromolecule to the cytoplasm of a cell. The present disclosure provides compositions comprising an endosomal disruptor and a macromolecule. The present disclosure provides methods of delivering a macromolecule to the cytoplasm of a cell.

12 Claims, 25 Drawing Sheets

Specification includes a Sequence Listing.

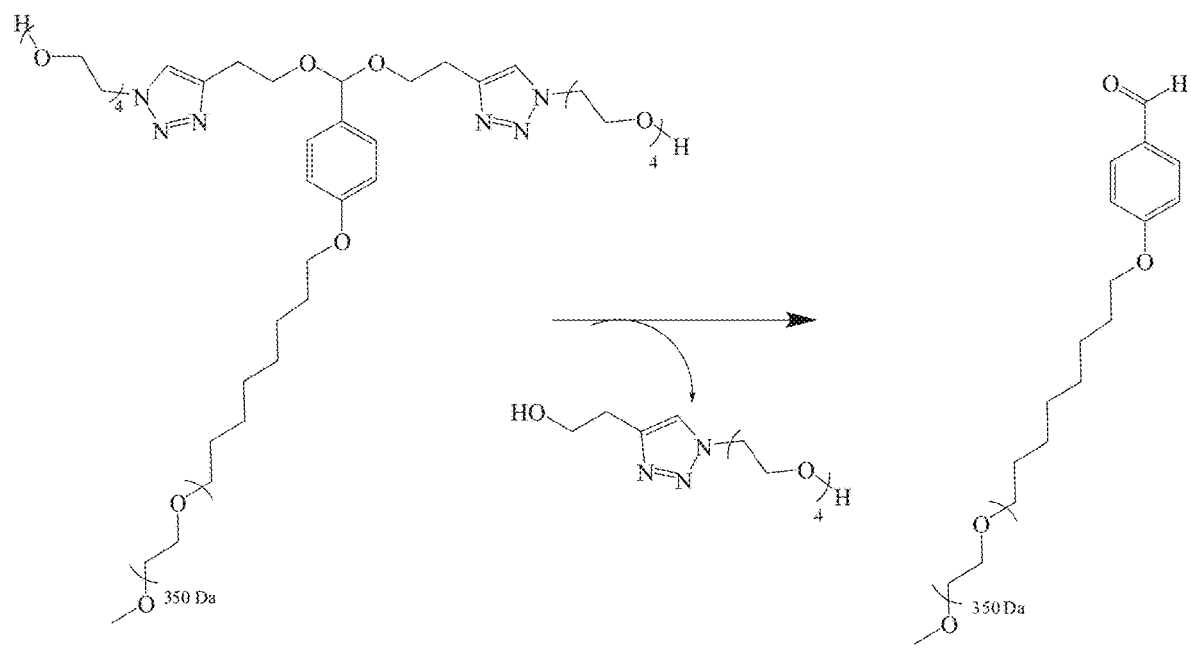
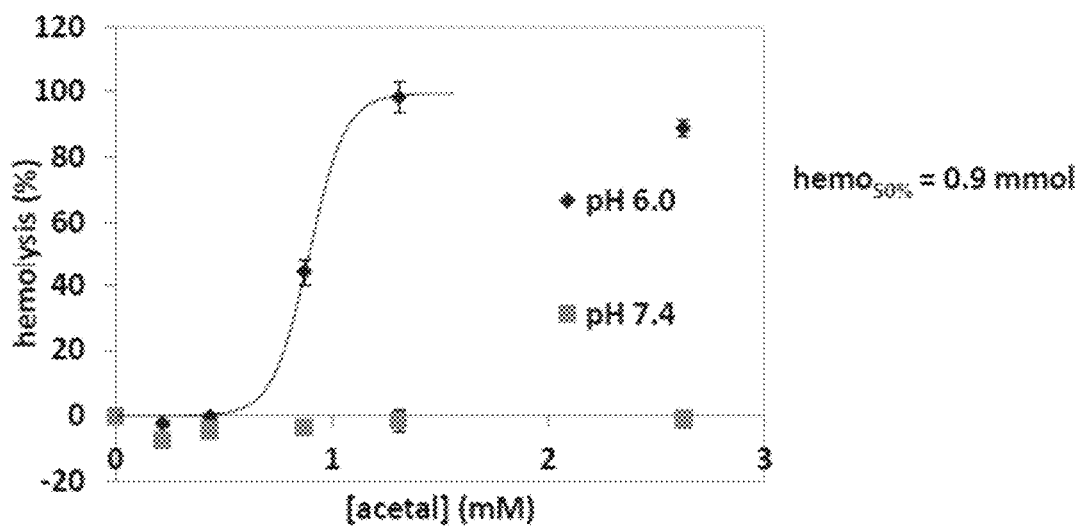
FIG. 1A

FIG. 6A

*Streptococcus pyogenes* Cas9

MDKKYSIGLDIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYAHLFDDKVMKQLKRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYLQNGRDMYVDQ
ELDINRLSDYDVDHIVPQSFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELALPSKYVNFLYL
ASHYEKLKGSPEDNEQKQLFVEQHKHYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD

FIG. 6B

>nSpCas9 (SpCas9 D10A)
MDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIHL
GELHAILRRQEDFYPFLKDNREKIEKILTFRIPYYVGPLARGNSRFAWMTRKSEETITPWNFEEVVDKGASAQSFIERMTNFD
KNLPNEKVLPKHSLLYEYFTVYNELTKVKYVTEGMRKPAFLSGEQKKAIVDLLFKTNRKVTVKQLKEDYFKKIECFDSVEIS
GVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVDE
LVKVMGRHKPENIVIEMARENQTTQKGQKNSRERMKRIEEGIKELGSQILKEHPVENTQLQNEKLYLYYLQNGRDMYVDQE
LDINRLSDYDVDHIVPQSFLKDDSIDNKVLTRSDKNRGKSDNVPSEEVVKKMKNYWRQLLNAKLITQRKFDNLTKAERGGL
SELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVRKMIAKSEQEIGKATAKYFFYSNIMNFFKTEITLANGEIRKRPLIETNGETGEIV
WDKGRDFATVRKVLSMPQVNIVKKTEVQTGGFSKESILPKRNSDKLIARKKDWDPKKYGGFDSPTVAYSVLVVAKVEKGK
SKKLKSVKELLGITIMERSSFEKNPIDFLEAKGYKEVKKDLIIKLPKYSLFELENGRKRMLASAGELQKGNELALPSKYVNFLY
LASHYEKLKGSPEDNEQKQLFVEQHKHYLDEIIEQISEFSKRVILADANLDKVLSAYNKHRDKPIREQAENIIHLFTLTNLGAP
AAFKYFDTTIDRKRYTSTKEVLDATLIHQSITGLYETRIDLSQLGGD

FIG. 6C

SpCas9 (H840A)
MDKKYSIGLDIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYYLQNGRDMYVDQ
ELDINRLSDYDVDAIVPQSFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELALPSKYVNFLYL
ASHYEKLKGSPEDNEQKQLFVEQHKHYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD

FIG. 6D

SpCas9 (D10A; H840A)
MDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETITPWNFEEVVDKGASAQSFIERMTN
FDKNLPNEKVLPKHSLLYEFTVYNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYYLQNGRDMYVDQ
ELDINRLSDYDVDAIVPQSFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELALPSKYVNFLYL
ASHYEKLKGSPEDNEQKQLFVEQHKHYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD

FIG. 6E

>enSpCas9 (nCas9 with K848A/K1003A/R1060A mutations
Slaymaker, Ian M., et al. "Rationally engineered Cas9 nucleases with improved specificity." Science 351.6268 (2016): 84-88.

MDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIHL
GELHAILRRQEDFYPFLKDNREKIEKILTFRIPYYVGPLARGNSRFAWMTRKSEETITPWNFEEVVDKGASAQSFIERMTNFD
KNLPNEKVLPKHSLLYEYFTVYNELTKVKYVTEGMRKPAFLSGEQKKAIVDLLFKTNRKVTVKQLKEDYFKKIECFDSVEIS
GVEDRFNASLGTYHDLLKIIKDKDFLDNEENEDILEDIVLTLTLFEDREMIEERLKTYAHLFDDKVMKQLKRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYLQNGRDMYVDQE
LDINRLSDYDVDHIVPQSFLADDSIDNKVLTRSDKNRGKSDNVPSEEVVKKMKNYWRQLLNAKLITQRKFDNLTKAERGGL
SELDKAGFIKRQLVETRQITKHVAQILDSRMNTKYDENDKLIREVKVITLKSKLVSDFRKDFQFYKVREINNYHHAHDAYLN
AVVGTALIKKYPALESEFVYGDYKVYDVRKMIAKSEQEIGKATAKYFFYSNIMNFFKTEITLANGEIRKAPLIETNGETGEIV
WDKGRDFATVRKVLSMPQVNIVKKTEVQTGGFSKESILPKRNSDKLIARKKDWDPKKYGGFDSPTVAYSVLVVAKVEKGK
SKKLKSVKELLGITIMERSSFEKNPIDFLEAKGYKEVKKDLIIKLPKYSLFELENGRKRMLASAGELQKGNELALPSKYVNFLY
LASHYEKLKGSPEDNEQKQLFVEQHKHYLDEIIEQISEFSKRVILADANLDKVLSAYNKHRDKPIREQAENIIHLFTLTNLGAP
AAFKYFDTTIDRKRYTSTKEVLDATLJHQSITGLYETRIDLSQLGGD

FIG. 6F

>nSpCas9-HF1
Kleinstiver, Benjamin P., et al. "High-fidelity CRISPR-Cas9 variants with undetectable genome-wide off-targets." Nature 529.7587 (2016): 490.

DKKYSIGLAIGTNSVGWAVITDEYKVPSKKFKVLGNTDRHSIKKNLIGALLFDSGETAEATRLKRTARRRYTRRKNRICYLQE
IFSNEMAKVDDSFFHRLEESFLVEEDKKHERHPIFGNIVDEVAYHEKYPTIYHLRKKLVDSTDKADLRLIYLALAHMIKFRGH
FLIEGDLNPDNSDVDKLFIQLVQTYNQLFEENPINASGVDAKAILSARLSKSRRLENLIAQLPGEKKNGLFGNLIALSLGLTPNF
KSNFDLAEDAKLQLSKDTYDDDLDNLLAQIGDQYADLFLAAKNLSDAILLSDILRVNTEITKAPLSASMIKRYDEHHQDLTLL
KALVRQQLPEKYKEIFFDQSKNGYAGYIDGGASQEEFYKFIKPILEKMDGTEELLVKLNREDLLRKQRTFDNGSIPHQIHLGE
LHAILRRQEDFYPFLKDNREKIEKILTFRIPYYVGPLARGNSRFAWMTRKSEETITPWNFEEVVDKGASAQSFIERMTAFDKN
LPNEKVLPKHSLLYEYFTVYNELTKVKYVTEGMRKPAFLSGEQKKAIVDLLFKTNRKVTVKQLKEDYFKKIECFDSVEISGV
EDRFNASLGTYHDLLKIIKDKDFLDNEENEDILEDIVLTLTLFEDREMIEERLKTYAHLFDDKVMKQLKRRRYTGWGALSRK
LINGIRDKQSGKTILDFLKSDGFANRNFMALIHDDSLTFKEDIQKAQVSGQGDSLHEHIANLAGSPAIKKGILQTVKVVDELV
KVMGRHKPENIVIEMARENQTTQKGQKNSRERMKRIEEGIKELGSQILKEHPVENTQLQNEKLYLYLQNGRDMYVDQELD
INRLSDYDVDHIVPQSFLKDDSIDNKVLTRSDKNRGKSDNVPSEEVVKKMKNYWRQLLNAKLITQRKFDNLTKAERGGLSE
LDKAGFIKRQLVETRAITKHVAQILDSRMNTKYDENDKLIREVKVITLKSKLVSDFRKDFQFYKVREINNYHHAHDAYLNAV
VGTALIKKYPKLESEFVYGDYKVYDVRKMIAKSEQEIGKATAKYFFYSNIMNFFKTEITLANGEIRKRPLIETNGETGEIVWD
KGRDFATVRKVLSMPQVNIVKKTEVQTGGFSKESILPKRNSDKLIARKKDWDPKKYGGFDSPTVAYSVLVVAKVEKGKSKK
LKSVKELLGITIMERSSFEKNPIDFLEAKGYKEVKKDLIIKLPKYSLFELENGRKRMLASAGELQKGNELALPSKYVNFLYLAS
HYEKLKGSPEDNEQKQLFVEQHKHYLDEIIEQISEFSKRVILADANLDKVLSAYNKHRDKPIREQAENIIHLFTLTNLGAPAAF
KYFDTTIDRKRYTSTKEVLDATLIHQSITGLYETRIDLSQLGGD

FIG. 7

*Staphylococcus aureus* Cas9

MKRNYILGLDIGITSVGYGIIDYETRDVIDAGVRLFKEANVENNEGRRSKRGARRLKRRRRHRIQRVKKLLFDYNLLTDHSEL
SGINPYEARVKGLSQKLSEEEFSAALLHLAKRRGVHNVNEVEEDTGNELSTKEQISRNSKALEEKYVAELQLERLKKDGEV
RGSINRFKTSDYVKEAKQLLKVQKAYHQLDQSFIDTYIDLLETRRTYYEGPGEGSPFGWKDIKEWYEMLMGHCTYFPEELR
SVKYAYNADLYNALNDLNNLVITRDENEKLEYYEKFQIIENVFKQKKKPTLKQIAKEILVNEEDIKGYRVTSTGKPEFTNLKVY
HDIKDITARKEIIENAELLDQIAKILTIYQSSEDIQEELTNLNSELTQEEIEQISNLKGYTGTHNLSLKAINLILDELWHTNDNQIAI
FNRLKLVPKKVDLSQQKEIPTTLVDDFILSPVVKRSFIQSIKVINAIIKKYGLPNDIIIELAREKNSKDAQKMINEMQKRNRQTN
ERIEEIIRTTGKENAKYLIEKIKLHDMQEGKCLYSLEAIPLEDLLNNPFNYEVDHIIPRSVSFDNSFNNKVLVKQEENSKKGNR
TPFQYLSSSDSKISYETFKKHILNLAKGKGRISKTKKEYLLEERDINRFSVQKDFINRNLVDTRYATRGLMNLLRSYFRVNNL
DVKVKSINGGFTSFLRRKWKFKKERNKGYKHHAEDALIIANADFIFKEWKKLDKAKKVMENQMFEEKQAESMPEIETEQEY
KEIFITPHQIKHIKDFKDYKYSHRVDKKPNRELINDTLYSTRKDDKGNTLIVNNLNGLYDKDNDKLKKLINKSPEKLLMYHHDP
QTYQKLKLIMEQYGDEKNPLYKYYEETGNYLTKYSKKDNGPVIKKIKYYGNKLNAHLDITDDYPNSRNKVVKLSLKPYRFDV
YLDNGVYKFVTVKNLDVIKKENYYEVNSKCYEEAKKLKKISNQAEFIASFYNNDLIKINGELYRVIGVNNDLLNRIEVNMIDITY
REYLENMNDKRPPRIIKTIASKTQSIKKYSTDILGNLYEVKSKKHPQIIKKG

FIG. 8A

*Francisella tularensis* Cpf1

```
   1  MSIYQEFVNK  YSLSKTLRFE  LIPQGKTLEN  IKARGLIIDD  EKRAKDYKKA  KQIIDKYHQF
  61  FIEEILSSVC  ISEDLLQNYS  DVYFKLKKSD  DDNLQKDFKS  AKDTIKKQIS  EYIKDSEKFK
 121  NLFNQNLIDA  KKGQESDLIL  WLKQSKDNGI  ELFKANSDIT  DIDEALEIIK  SFKGWTTYFK
 181  GFHENRKNVY  SSNDIPTSII  YRIVDDNLPK  FLENKAKYES  LKDKAPEAIN  YEQIKKDLAE
 241  ELTFDIDYKT  SEVNQRVFSL  DEVFEIANFN  NYLNQSGITK  FNTIIGGKFV  NGENTKRKGI
 301  NEYINLYSQQ  INDKTLKKYK  MSVLFKQILS  DTESKSFVID  KLEDDSDVVT  TMQSFYEQIA
 361  AFKTVEEKSI  KETLSLFDD   LKAQKLDLSK  IYFKNDKSLT  DLSQQVFDDY  SVIGTAVLEY
 421  ITQQIAPKNL  DNPSKKEQEL  IAKKTEKAKY  LSLETIKLAL  EEFNKHRDID  KQCRFEEILA
 481  NFAAIPMIFD  EIAQNKDNLA  QISIKYQNQG  KKDLLQASAE  DDVKAIKDLL  DQTNNLLHKL
 541  KIFHISQSED  KANILDKDEH  FYLVFEECYF  ELANIVPLYN  KIRNYITQKP  YSDEKFKLNF
 601  ENSTLANGWD  KNKEPDNTAI  LFIKDDKYYL  GVMNKKNNKI  FDDKAIKENK  GEGYKKIVYK
 661  LLPGANKMLP  KVFFSAKSIK  FYNPSEDILR  IRNHSTHTKN  GSPQKGYEKF  EFNIEDCRKF
 721  IDFYKQSISK  HPEWKDFGFR  FSDTQRYNSI  DEFYREVENQ  GYKLTFENIS  ESYIDSVVNQ
 781  GKLYLFQIYN  KDFSAYSKGR  PNLHTLYWKA  LFDERNLQDV  VYKLNGEAEL  FYRKQSIPKK
 841  ITHPAKEAIA  NKNKDNPKKE  SVFEYDLIKD  KRFTEDKFFF  HCPITINFKS  SGANKFNDEI
 901  NLLLKEKAND  VHILSIDRGE  RHLAYYTLVD  GKGNIIKQDT  FNIIGNDRMK  TNYHDKLAAI
 961  EKDRDSARKD  WKKINNIKEM  KEGYLSQVVH  EIAKLVIEYN  AIVVFEDLNF  GFKRGRFKVE
1021  KQVYQKLEKM  LIEKLNYLVF  KDNEFDKTGG  VLRAYQLTAP  FETFKKMGKQ  TGIIYYVPAG
1081  FTSKICPVTG  FVNQLYPKYE  SVSKSQEFFS  KFDKICYNLD  KGYFEFSFDY  KNFGDKAAKG
1141  KWTIASFGSR  LINFRNSDKN  HNWDTREVYP  TKELEKLLKD  YSIEYGHGEC  IKAAICGESD
1201  KKFFAKLTSV  LNTILQMRNS  KTGTELDYLI  SPVADVNGNF  FDSRQAPKNM  PQDADANGAY
1261  HIGLKGLMLL  GRIKNNQEGK  KLNLVIKNEE  YFEFVQNRNN
```

FIG. 8B

Acidaminococcus sp. BV3L6 type V CRISPR-associated protein Cpf1

TQFEGFTNLYQVSKTLRFELIPQGKTLKHIQEQGFIEEDKARNDHYKELKPIIDRIYKTYADQCLQLVQLDWENLSAAIDSYR
KEKTEETRNALIEEQATYRNAIHDYFIGRTDNLTDAINKRHAEIYKGLFKAELFNGKVLKQLGTVTTTEHENALLRSFDKFTT
YFSGFYENRKNVFSAEDISTAIPHRIVQDNFPKFKENCHIFTRLITAVPSLREHFENVKKAIGIFVSTSIEEVFSFPFYNQLLTQTQ
IDLYNQLLGGISREAGTEKIKGLNEVLNLAIQKNDETAHIIASLPHRFIPLFKQILSDRNTLSFILEEFKSDEEVIQSFCKYKTLLR
NENVLETAEALFNELNSIDLTHIFISHKKLETISSALCDHWDTLRNALYERRISELTGKITKSAKEKVQRSLKHEDINLQEIISAA
GKELSEAFKQKTSEILSHAHAALDQPLPTTLKKQEEKEILKSQLDSLLGLYHLLDWFAVDESNEVDPEFSARLTGIKLEMEPSL
SFYNKARNYATKKPYSVEKFKLNFQMPTLASGWDVNKEKNNGAILFVKNGLYYLGIMPKQKGRYKALSFEPTEKTSEGFD
KMYYDYFPDAAKMIPKCSTQLKAVTAHFQTHTPILLSNNFIEPLEITKEIYDLNNPEKEPKKFQTAYAKKTGDQKGYREALC
KWIDFTRDFLSKYTKTTSIDLSSLRPSSQYKDLGEYYAELNPLLYHISFQRIAEKEIMDAVETGKLYLFQIYNKDFAKGHHGKP
NLHTLYWTGLFSPENLAKTSIKLNGQAELFYRPKSRMKRMAHRLGEKMLNKKLKDQKTPIPDTLYQELYDYVNHRLSHDLS
DEARALLPNVITKEVSHEIIKDRRFTSDKFFFHVPITLNYQAANSPSKFNQRVNAYLKEHPETPIIGIDRGERNLIYITVIDSTGKI
LEQRSLNTIQQFDYQKKLDNREKERVAARQAWSVVGTIKDLKQGYLSQVIHEIVDLMIHYQAVVLENLNFGFKSKRTGIAE
KAVYQQFEKMLIDKLNCLVLKDYPAEKVGGVLNPYQLTDQFTSFAKMGTQSGFLFYVPAPYTSKIDPLTGFVDPFVWKTIK
NHESRKHFLEGFDFLHYDVKTGDFILHFKMNRRNLSFQRGLPGFMPAWDIVFEKNETQFDAKGTPFIAGKRIVPVIENHRFTGR
YRDLYPANELIALLEEKGIVFRDGSNILPKLLENDDSHAIDTMVALIRSVLQMRNSNAATGEDYINSPVRDLNGVCFDSRFQN
PEWPMDADANGAYHIALKGQLLNHLKESKDLKLQNGISNQDWLAYIQELRN

FIG. 8C

>nCpf1 (AsCpf1 R1225A)
TQFEGFTNLYQVSKTLRFELIPQGKTLKHIQEQGFIEEDKARNDHYKELKPIIDRIYKTYADQCLQLVQLDWENLSAAIDSYR
KEKTEETRNALIEEQATYRNAIHDYFIGRTDNLTDAINKRHAEIYKGLFKAELFNGKVLKQLGTVTTEHENALLRSFDKFTT
YFSGFYENRKNVFSAEDISTAIPHRIVQDNFPKFKENCHIFTRLITAVPSLREHFENVKKAIGIFVSTSIEEVFSFPFYNQLLTQTQ
IDLYNQLLGGISREAGTEKIKGLNEVLNLAIQKNDETAHIIASLPHRFIPLFKQILSDRNTLSFILEEFKSDEEVIQSFCKYKTLLR
NENVLETAEALFNELNSIDLTHIFISHKKLETISSALCDHWDTLRNALYERRISELTGKITKSAKEKVQRSLKHEDINLQEIISAA
GKELSEAFKQKTSEILSHAHAALDQPLPTTLKKQEEKEILKSQLDSLLGLYHLLDWFAVDESNEVDPEFSARLTGIKLEMEPSL
SFYNKARNYATKKPYSVEKFKLNFQMPTLASGWDVNKEKNNGAILFVKNGLYYLGIMPKQKGRYKALSFEPTEKTSEGFD
KMYYDYFPDAAKMIPKCSTQLKAVTAHFQTHTTPILLSNNFIEPLEITKEIYDLNNPEKEPKKFQTAYAKKTGDQKGYREALC
KWIDFTRDFLSKYTKTTSIDLSSLRPSSQYKDLGEYYAELNPLLYHISFQRIAEKEIMDAVETGKLYLFQIYNKDFAKGHHGKP
NLHTLYWTGLFSPENLAKTSIKLNGQAELFYRPKSRMKRMAHRLGEKMLNKKLKDQKTPIPDTLYQELYDYVNHRLSHDLS
DEARALLPNVITKEVSHEIIKDRRFTSDKFFFHVPITLNYQAANSPSKFNQRVNAYLKEHPETPIIGIDRGERNLIYITVIDSTGKI
LEQRSLNTIQQFDYQKKLDNREKERVAARQAWSVVGTIKDLKQGYLSQVIHEIVDLMIHYQAVVLENLNFGFKSKRTGIAE
KAVYQQFEKMLIDKLNCLVKDYPAEKVGGVLNPYQLTDQFTSFAKMGTQSGFLFYVPAPYTSKIDPLTGFVDPFVWKTIK
NHESRKHFLEGFDFLHYDVKTGDFILHFKMNRNLSFQRGLPGFMPAWDIVFEKNETQFDAKGTPFIAGKRIVPVIENHRFTGR
YRDLYPANELIALLEEKGIVFRDGSNILPKLLENDDSHAIDTMVALIRSVLQMANSNAATGEDYINSPVRDLNGVCFDSRFQN
PEWPMDADANGAYHIALKGQLLLNHLKESKDLKLQNGISNQDWLAYIQELRN

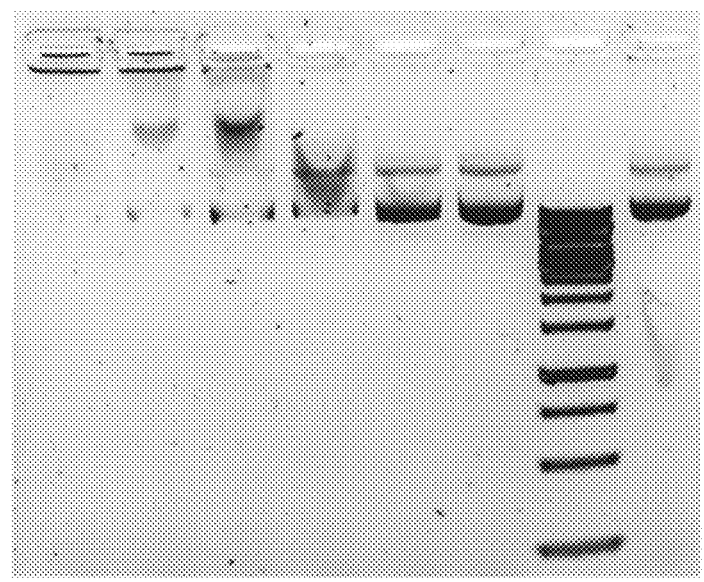
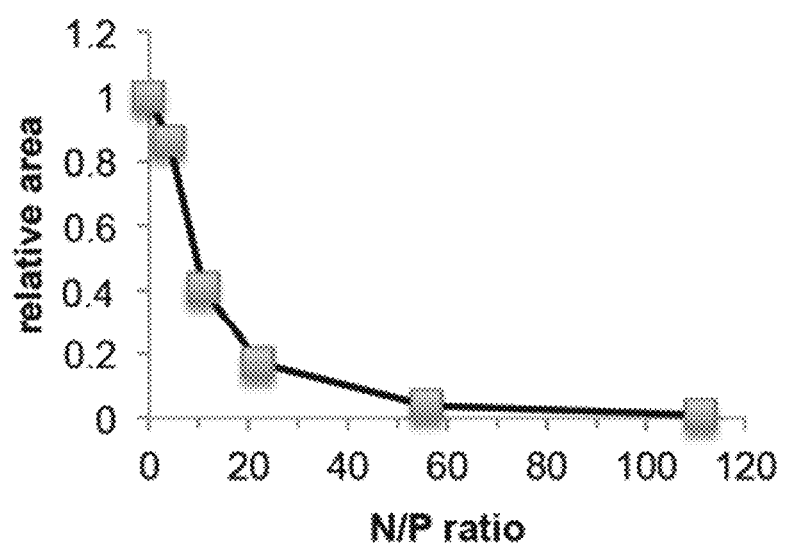
FIG. 15

COMPOSITIONS AND METHODS FOR DELIVERY OF MACROMOLECULES

CROSS-REFERENCE

This application claims the benefit of U.S. Provisional Patent Application No. 62/594,319, filed Dec. 4, 2017, which application is incorporated herein by reference in its entirety.

STATEMENT REGARDING FEDERALLY SPONSORED RESEARCH

This invention was made with government support under Grant No. EB023776 awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "BERK-380PRV_seq_list_ST25.txt" created on Nov. 30, 2017 and having a size of 7,835 KB. The contents of the text file are incorporated by reference herein in their entirety.

INTRODUCTION

Macromolecules such as proteins and nucleic acids are a fast-growing class of drugs. The ability of such macromolecules to target intracellular components is hampered by delivery barriers. One such barrier is the uptake of large molecules into endosomes and the ensuing disintegration in lysosomes.

Although various nanoparticle, protein, and peptide-based strategies have been developed for disrupting endosomes, it has been challenging to assemble them with macromolecules, due to their large size and complexity.

There is a need in the art for endosomal disrupting agents that can be assembled with macromolecules.

SUMMARY

The present disclosure provides endosomal disruptors, which are useful for facilitating delivery of a macromolecule to the cytoplasm of a cell. The present disclosure provides compositions comprising an endosomal disruptor and a macromolecule. The present disclosure provides methods of delivering a macromolecule to the cytoplasm of a cell.

BRIEF DESCRIPTION OF THE DRAWINGS

The invention is best understood from the following detailed description when read in conjunction with the accompanying figures. The patent or application file contains at least one figure executed in color. It is emphasized that, according to common practice, the various features of the figures are not to-scale. On the contrary, the dimensions of the various features are arbitrarily expanded or reduced for clarity. Included in the drawings are the following figures. It is understood that the figures, described below, are for illustration purposes only. The figures are not intended to limit the scope of the present teachings in any way.

FIG. 1A-1C. (FIG. 1A) illustrates that an exemplary endosomal disruptor (Compound 1) has pH dependent hemolytic activity; (FIG. 1B) illustrates the glutathione reduction of compound 3 and subsequent endosome disruption by the released endosomal disruptive surfactant; (FIG. 1C) illustrates the hemolytic activity of the endosomal disruptive surfactant 3A.

(FIG. 5A) illustrates yeast spheroplasts with DNA in the absence of an exemplary endosomal disruptor; and (FIG. 5B) illustrates yeast spheroplasts with DNA in combination with an exemplary endosomal disruptor.

FIG. 6A-6F provides amino acid sequences of *Streptococcs pyoes* Cas9 (FIG. 6A) and variants of *Streptococcs pyoes* Cas9 (FIG. 6B-6F).

FIG. 7 provides an amino acid sequence of *Staphylococcu aureus* Cas9.

FIG. 8A-8C provide amino acid sequences of *Francisella tularensis* Cpf1 (FIG. 8A), *Acidaminococcus* sp. BV3L6 Cpf1 (FIG. 8B), and a variant Cpf1 (FIG. 8C).

FIG. 15 illustrates the effect of N/P ratio on DNA retention.

DEFINITIONS

Figure 1B:
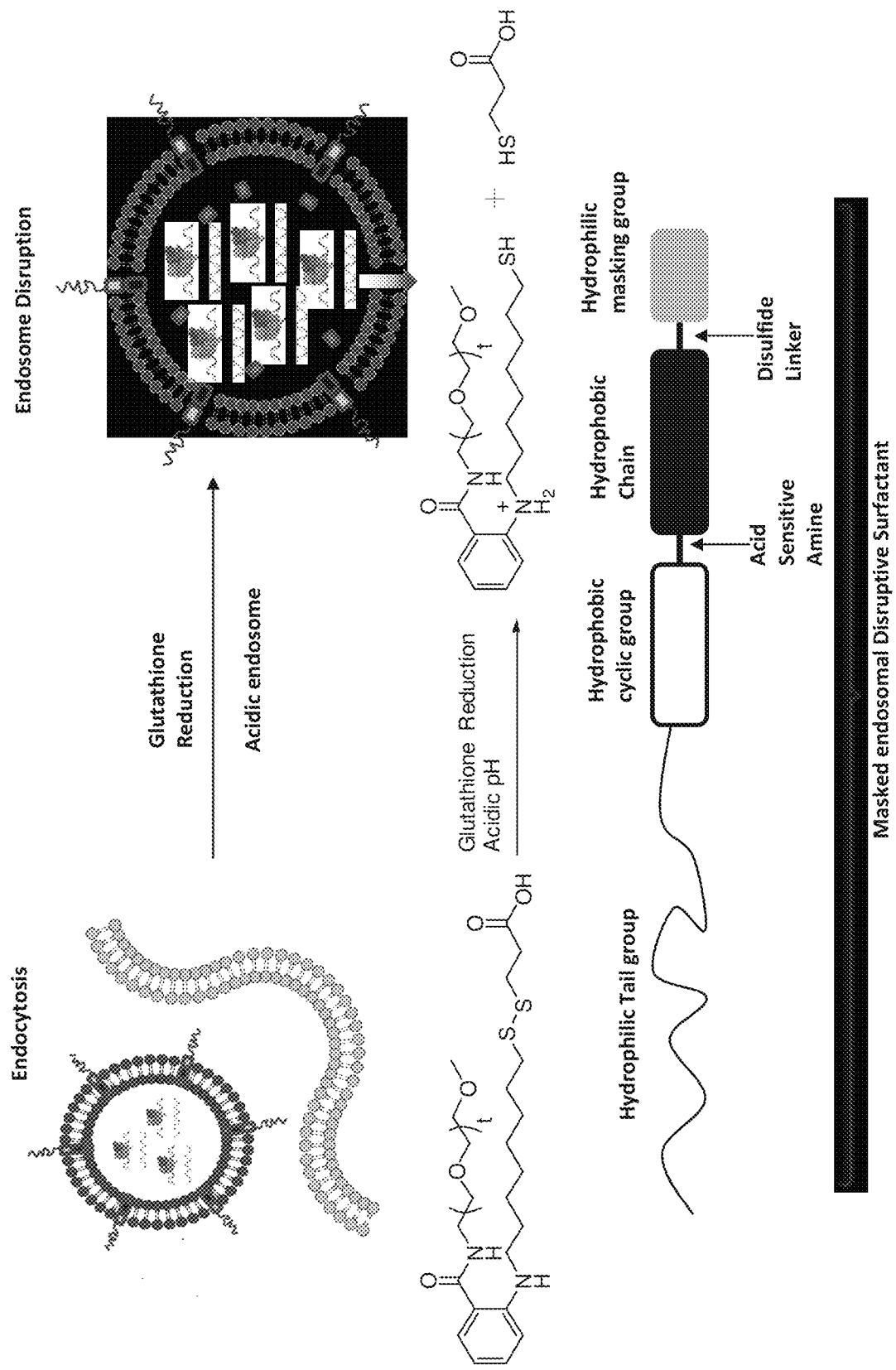

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Where compounds described herein contain one or more chiral centers and/or double-bond isomers (i.e., geometric isomers), enantiomers or diastereomers, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^{2}H$, $^{3}H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

The term "alkyl" as used herein refers to a branched or unbranched saturated hydrocarbon group (i.e., a monoradical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

"Substituted alkylene" refers to an alkylene group having from 1 to 3 hydrogens replaced with substituents as described for carbons in the definition of "substituted" below.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkaryl" or "aralkyl" refers to the groups-alkylene-aryl and-substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups-alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocylooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—.

"Acylamino" refers to the groups —NR$^{20}$C(O)alkyl, —NR$^{20}$C(O) substituted alkyl, N R$^{20}$C(O)cycloalkyl, —NR$^{20}$C(O) substituted cycloalkyl, —NR$^{20}$C(O)cycloalkenyl, —NR$^{20}$C(O) substituted cycloalkenyl, —NR$^{20}$C(O) alkenyl, —NR$^{20}$C(O) substituted alkenyl, —NR$^{20}$C(O) alkynyl, —NR$^{20}$C(O) substituted alkynyl, —NR$^{20}$C(O)aryl, —NR$^{20}$C(O) substituted aryl, —NR$^{20}$C(O)heteroaryl, —NR$^{20}$C(O) substituted heteroaryl, —NR$^{20}$C(O)heterocyclic, and —NR$^{20}$C(O) substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O) NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl—C(O)O—, substituted alkyl-C(O)O—, cycloalkyl-C(O)O—, substituted cycloalkyl-C(O)O—, aryl-C(O)O—, heteroaryl-C(O) O—, and heterocyclyl-C(O)O— wherein alkyl, substituted alkyl, cycloalkyl, substituted cycloalkyl, aryl, heteroaryl, and heterocyclyl are as defined herein.

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. Aryl is intended to include stable cyclic, heterocyclic, polycyclic, and polyheterocyclic unsaturated $C_3$-$C_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, $C_1$-$C_8$ alkoxy, $C_1$-$C_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry). If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" or "azide" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)-alkyl, —C(O)-substituted alkyl, —C(O)-alkenyl, —C(O)-substituted alkenyl, —C(O)-alkynyl, —C(O)-substituted alkynyl, —C(O)-aryl, —C(O)-substituted aryl, —C(O)-cycloalkyl, —C(O)-substituted cycloalkyl, —C(O)-cycloalkenyl, —C(O)-substituted cycloalkenyl, —C(O)-heteroaryl, —C(O)-substituted heteroaryl, —C(O)-heterocyclic, and —C(O)-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)-cycloalkenyl, —O—C(O)O-substituted cycloalkenyl, —O—C(O)-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

As used herein, "carbocycle" or "carbocyclic ring" is intended to mean any stable monocyclic, bicyclic, or tricyclic ring having the specified number of carbons, any of which may be saturated, unsaturated, or aromatic. For example, a C3-14 carbocycle is intended to mean a mono-, bi-, or tricyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane, and [2.2.2]bicyclooctane. A bridged ring occurs when a covalent bond or one or more carbon atoms link two non-adjacent carbon atoms in a ring. In one embodiment, bridge rings are one or two carbon atoms. It is noted that a bridge always converts a monocyclic ring into a bicyclic ring. When a ring is bridged, the substituents recited for the ring may also be present on the bridge. Fused (e.g., naphthyl and tetrahydronaphthyl) and spiro rings are also included.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups-alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocylooxy, thiol, thioalkoxy, substituted thioalkoxy, aryl, aryloxy, heteroaryl, heteroaryloxy, heterocyclyl, heterocylooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cylcoalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —NR$^{80}$R$^{80}$, trihalomethyl, —CN, —OCN, —SCN —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$, (subscript 0.5 means that one of the counter ions for such divalent alkali earth ions can be an ionized form of a compound of the present disclosure and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{8o}$ and M$^+$ are as previously defined, provided that in case of substituted alkene or alkyne, the substituents are not —O$^-$M$^+$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —SR$^{70}$, —S$^-$M$^+$, —NR$^{80}$R$^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

"Pharmaceutically effective amount" and "therapeutically effective amount" refer to an amount of a compound sufficient to elicit the desired therapeutic effect (e.g., treatment of a specified disorder or disease or one or more of its symptoms and/or prevention of the occurrence of the disease or disorder). In reference to polyglutamine diseases, a pharmaceutically or therapeutically effective amount includes an amount sufficient to, among other things, prevent or cause a reduction of proteinaceous deposits in the brain of a subject.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

By the term "functional groups" is meant chemical groups such as halo, hydroxyl, sulfhydryl, C1-C24 alkoxy, C2-C24 alkenyloxy, C2-C24 alkynyloxy, C5-C20 acyloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), halocarbonyl (—CO)—X where X is halo), C2-C24 alkylcarbonato (—O—(CO)—O-alkyl), C6-C20 arylcarbonato (—O—(CO)—O-aryl), carboxy (—COOH), carboxylato (—COO—), carbamoyl (—(CO)—$NH_2$), mono-substituted C1-C24 alkylcarbamoyl (—(CO)—NH(C1-C24 alkyl)), di-substituted alkylcarbamoyl (—(CO)—N(C1-C24 alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—N+≡C—), cyanato (—O—C≡N), isocyanato (—O—N+≡C—), isothiocyanato (—S—C≡N), azido (—N=N+=N—), formyl (—(CO)—H), thioformyl (—(CS)—H), amino (—$NH_2$), mono- and di-(C1-C24 alkyl)-substituted amino, mono- and di-(C5-C20 aryl)-substituted amino, C2-C24 alkylamido (—NH—(CO)-alkyl), C5-C20 arylamido (—NH—(CO)-aryl), imino (—CR=NH where R=hydrogen, C1-C24 alkyl, C5-C20 aryl, C6-C20 alkaryl, C6-C20 aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—O—), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—$SO_2$-alkyl), C5-C20 arylsulfonyl (—$SO_2$-aryl), phosphono (—P(O)(OH)$_2$), phosphonato (—P(O)(O—)$_2$), phosphinato (—P(O)(O—)), phospho (—$PO_2$), and phosphino (—$PH_2$), mono- and di-(C1-C24 alkyl)-substituted phosphino, mono- and di-(C5-C20 aryl)-substituted phosphine. In addition, the aforementioned functional groups may, if a particular group permits, be further substituted with one or more additional functional groups or with one or more hydrocarbyl moieties such as those specifically enumerated above.

By "linking" or "linker" as in "linking group," "linker moiety," etc., is meant a linking moiety that connects two groups via covalent bonds. The linker may be linear, branched, cyclic or a single atom. Examples of such linking groups include alkyl, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (—O—), epithio (—S—), epidioxy (—O—O—), epidithio (—S—S—), carbonyldioxy (—O—CO—O—), alkyldioxy (—O—(CH2)n—O—), epoxyimino (—O—NH—), epimino (—NH—), carbonyl (—CO—), etc. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, poly(ethylene glycol) unit(s) (e.g., —(CH$_2$—CH$_2$—O)—); ethers, thioethers, amines, alkyls (e.g., (C$_1$-C$_{12}$)alkyl), which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable. Any convenient orientation and/or connections of the linkers to the linked groups may be used.

As used herein, the terms "chemoselective group", "chemoselective functional group" and "chemoselective tag" are used interchangeably and refer to chemoselective reactive groups that are capable of selectively reacting with a compatible chemoselective functional group to form a covalent bond, or to one or more such chemoselective reactive group and a linking group. Hence, in some cases, the chemoselective group includes one or more chemoselective reactive groups and linking group that links one or more chemoselective groups to another group, e.g. to a hydrophilic tail, as described below. In some cases, the chemoselective reactive group is capable of selectively reacting with a compatible chemoselective functional group to form a covalent bond after activation of one or more functional groups.

Chemoselective functional groups of interest include, but are not limited to, amines and carboxylic acids or active esters thereof, amines and isocyanates, amines and isothiocyanates, amines and N-hydroxysuccinimide (NHS) esters, amines and aldehydes (e.g. glyoxals), thiols and maleimides, thiols and iodoacetamides, carboxylic acids and thiols, tetrazines and alkenes, as well as groups that can react with one another via Click chemistry, e.g., azide and alkyne groups (e.g., cyclooctyne groups), tetrazine, transcyclooctene, azides and phosphines (e.g. Staudinger ligation), dienes and dieneophiles, sulfur(VI) fluoride exchange chemistry (SuFEX), sulfonyl fluoride, hydrazido, hydrazine, aldehyde, ketone, azido, alkyne, phosphine, epoxide, and the like. Additional chemoselective groups are described by Hermanson, Bioconjugate Techniques, Third Edition, Academic Press, 2013.

As used herein, the expression "acidic pH" means a pH of 6.0 or less (e.g., less than about 6.0, less than about 5.5, less than about 5.0, etc.). The expression "acidic pH" includes pH values of about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, 4.9, 4.85, 4.80, 4.75, 4.7, 4.65, 4.6, 4.55, 4.5 or less.

As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

As used herein, the terms "terminal group" or "end group" are used interchangeably to refer to the groups located at the terminals of the endosomal disruptor e.g. as described herein. Terminal groups of interest include, but are not limited to a terminal capping group, such as H, an aryl, a substituted aryl, a heteroaryl, a substituted heteroaryl, an alkyl or a substituted alkyl. In certain cases, the terminal group may be defined as a chemoselective group (e.g. as described herein).

As used herein, the term "hydrophilic group" by itself refers to a monovalent or multivalent group which includes a hydrophilic moiety and an optional linker. In some cases, a hydrophilic group is attached to the hydrophilic masking moiety and the hydrophilic tail moiety of the subject endosomal disruptors. The hydrophilic moiety is a moiety that is well solvated in aqueous environments, e.g., under reverse phase (RP) chromatography conditions, and that imparts increased water solubility on the group to which it is attached or incorporated (e.g., the linker). In some cases, the hydrophilic moiety is referred to as a hydrophilic functional group. In some cases, the hydrophilic moiety is a heterocycle. In certain cases, the hydrophilic moiety is a heteroaryl. In some cases, the hydrophilic moiety is charged (e.g., ionic). In some cases, the hydrophilic moiety is polar and neutral (e.g., non-ionic). It is understood that certain functional groups may be present in either an ionic or a non-ionic form, dependent on the surrounding conditions, e.g., solvent, pH and the like, and that all such forms of the hydrophilic moieties described herein are meant to be included in the present disclosure. For example, the hydrophilic moiety can be a basic group which is neutral until protonated, e.g., under aqueous conditions of a suitable pH, or the hydrophilic moiety can be an acidic group which is neutral until deprotonated, e.g., under aqueous conditions of a suitable pH.

A hydrophilic moiety can increase the solubility of the group to which it is attached in a predominantly aqueous solution, as compared to a control group which lacks the hydrophilic moiety. A hydrophilic moiety is different from a hydrophobic moiety which is not well solvated in aqueous environments. In certain instances, a hydrophilic group includes at least one neutral polar functional group per 5 carbons, or at least one charged functional group per 7 carbons. In some instances, a hydrophilic group (e.g., the hydrophilic group in isolated form as a discrete molecule) has solubility in water of at least 1% by weight.

Hydrophilic groups and hydrophilic moieties of interest include, but are not limited to, Nitrogen-containing heterocycle, amide, carbamate, carboxylic acid carboxy ester, methyl ether, cyano, amine, sulfonamide, sulfonate, urea, thiourea, sulfonic acid, carboxylate, phosphonate, phosphate, sulfate, sulfinate, sulfonium, polyethylene glycols (PEG) and modified PEGs, hydroxyl, ammonium, guanidinium, pyridinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —SO$_3$M', —PO$_3$M', —NR3+, Y', (CH$_2$CH$_2$O)pR and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —(CH$_2$CH$_2$O)

yyCH$_2$CH$_2$XRyy, —(CH$_2$CH$_2$O) yyCH2CH2X—, —X(CH$_2$CH$_2$O) yyCH$_2$CH$_2$—, glycol, and polyethylene glycol, wherein yy is selected from 1 to 1000, X is selected from O, S, and NRZZ, and RZZ and RYY are independently selected from H and C1-3 alkyl. In some cases, a hydrophilic moiety is (CH$_2$)x(OCH$_2$CH$_2$)yOCH$_3$ where each x is independently an integer from 0-20, each y is independently an integer from 0 to 50.

Nitrogen-containing heterocycles of interest that find use as hydrophilic moieties include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, and substituted versions thereof.

As used herein the term "PEG" refers to a polyethylene glycol or a modified polyethylene glycol. Modified polyethylene glycol polymers include a methoxypolyethylene glycol, and polymers that are unsubstituted or substituted at one end with an alkyl, a substituted alkyl or a functional group (e.g., as described herein). Any convenient linking groups may be utilized at the terminal of a PEG to connect the group to a moiety of interest including but not limited to, alkyl, aryl, hydroxyl, amino, acyl, acyloxy, carboxyl ester and amido terminal and/or substituent groups.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

In certain embodiments, a substituent may contribute to optical isomerism and/or stereo isomerism of a compound. Salts, solvates, hydrates, and prodrug forms of a compound are also of interest. All such forms are embraced by the present disclosure. Thus, the compounds described herein include salts, solvates, hydrates, prodrug and isomer forms thereof, including the pharmaceutically acceptable salts, solvates, hydrates, prodrugs and isomers thereof. In certain embodiments, a compound may be metabolized into a pharmaceutically active derivative.

Unless otherwise specified, reference to an atom is meant to include isotopes of that atom. For example, reference to H is meant to include $^1$H, $^2$H (i.e., D) and $^3$H (i.e., T), and reference to C is meant to include $^{12}$C and all isotopes of carbon (such as $^{13}$C).

The term "sample" as used herein relates to a material or mixture of materials, typically, although not necessarily, in fluid, i.e., aqueous, form, containing one or more components of interest. Samples may be derived from a variety of sources such as from food stuffs, environmental materials, a biological sample or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). In certain embodiments of the method, the sample includes a cell. In some instances of the method, the cell is in vitro. In some instances of the method, the cell is in vivo.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "polypeptide," "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. The term "polypeptide" includes lipoproteins, glycoproteins, and the like.

A "host cell," as used herein, denotes an in vivo or in vitro eukaryotic cell, or a cell from a multicellular organism (e.g., a cell line) cultured as a unicellular entity, which eukaryotic cells can be, or have been, used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector, a guide RNA, a donor DNA template, and the like. For example, a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The terms "individual," "subject," "host," and "patient," used interchangeably herein, refer to an individual organism, e.g., a mammal, including, but not limited to, murines, simians, non-human primates, humans, mammalian farm animals, mammalian sport animals, and mammalian pets.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an endosomal disruptor" includes a plurality of such endosomal disruptors and reference to "the macromolecule" includes reference to one or more macromolecules and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions of other terms and concepts appear throughout the detailed description below.

DETAILED DESCRIPTION

The present disclosure provides endosomal disruptors, which are useful for facilitating delivery of a macromolecule to the cytoplasm of a cell. The present disclosure provides compositions comprising an endosomal disruptor and a macromolecule. The present disclosure provides methods of delivering a macromolecule to the cytoplasm of a cell.

Endosomal Disruptor

The present disclosure provides endosomal disruptors, which are useful for facilitating delivery of a macromolecule to the cytoplasm of a cell. An endosomal disruptor of the present disclosure comprises a hydrophilic masking moiety, a cleavable linker capable of cleavage with an endosome to release an endosomal disrupting surfactant, and an endosomal disrupting surfactant. In some cases, the cleavable linker which links the masking moiety to the endosomal disrupting surfactant is an acid-labile linking group. The masking moiety masks the endosomal disrupting surfactant. Upon entering the endosomal compartment, the acid-labile linking group is hydrolyzed, thereby freeing and unmasking the endosomal disrupting surfactant. In some cases, the cleavable linker which links the masking moiety to the endosomal disrupting surfactant is cleaved under reducing conditions upon entering the endosomal compartment. It is understood that any convenient cleavable linker capable of being cleaved to release the endosomal disrupting surfactant upon entering the endosomal compartment, can be utilized in the subject endosomal disruptors. The released endosomal disrupting surfactant triggers endosomal disruption, allowing release of any co-delivered macromolecule into the cytoplasm. As used herein, the terms "endosomal disruptor" and "caged surfactant" are used interchangeably.

As disclosed herein the endosomal disrupting surfactant includes a hydrophobic group, comprising a cyclic group and a hydrophobic chain; and a hydrophilic tail group. In some cases, the endosomal disrupting surfactant is configured to be able to disrupt a membrane, e.g. a cell membrane, a micro-vesicle membrane, a lysosome membrane, or a combination thereof. In some cases, the cyclic group is a fluorophore. In certain cases, the hydrophobic chain includes a linear or branched alkyl chain. In certain cases, the hydrophilic tail group is a hydrophilic chain comprising PEG. In certain instances, the hydrophilic masking moiety also includes a hydrophilic chain comprising PEG. The subject endosomal disruptor may optionally include a chemoselective tag (e.g. configured to conjugate a cell targeting agent or a macromolecule), a linked biomolecule or a linked cell delivery agent. The chemoselective tag, linked biomolecule or linked cell delivery agent may be attached to the endosomal disruptor at any convenient position. In some cases, a chemoselective tag is attached directly or indirectly to the hydrophilic tail of the endosomal disrupting surfactant. In other cases, a chemoselective tag is attached directly or indirectly to the hydrophilic masking moiety. In some embodiments, the chemoselective tag is configured to selectively reacting with a compatible chemoselective functional group of a biomolecule to form a covalent bond.

In some cases, the subject endosomal disruptor compound is of the formula (I):

(M-Z-A-T)-Y                      (I)

wherein:

M is a hydrophilic masking group;

Z is a cleavable linker capable of cleavage with an endosome to release M and produce an endosomal disrupting surfactant;

A is a masked hydrophobic group comprising:
    a cyclic group selected from an aryl, a substituted aryl, a heteroaryl, a substituted heteroaryl, a saturated carbocycle, a substituted saturated carbocycle, a heterocycle and a substituted heterocycle; and
    a hydrophobic chain;

T is a hydrophilic tail group; and

Y is an optional group selected from a terminal group, a linker, a chemoselective tag (e.g. configured to conjugate a cell targeting agent or a macromolecule), a linked biomolecule and a linked cell delivery agent;

or a pharmaceutically acceptable salt or a solvate thereof.

The phrase "masking group" or "masking moiety" as used herein refers to a moiety which prevents a particular functional group of the membrane-disruptive moiety from undergoing a specific chemical reaction, but which is removable from the molecule following delivery to the endosomal compartment. The "masking moiety" is used in the conventional chemical sense as a group which reversibly renders unreactive a functional group under certain conditions of a desired reaction. After delivery to the endosomal compartment, the masking group may be removed to deprotect or unmask the endosomal disrupting surfactant. All masking groups M should be removable (and hence, labile) under conditions which do not degrade a substantial proportion of the molecules being synthesized. It should be noted that the functionality protected by the protecting group may or may not be a part of what is referred to as the masking group. In some embodiments, the functionality protected by the masking group (M) is a cleavable linker represented by group Z, capable of cleavage within an endosome to release the masking group M and produce an endosomal disrupting surfactant. In certain embodiments, the released masking group M is an inert group. In some embodiments, the hydrophilic masking group M is configured to mask the hydrophobic group A, i.e. the hydrophobic masking group M is configured to prevent the hydrophobic group A from undergoing a chemical reaction.

The hydrophilic masking group M is linked to the hydrophobic group A via a cleavable linker Z. In some cases, the group Z is a masked aldehyde, for example, an acetal group, a thioacetal group or a dithioacetal group. In some cases, the masking group M is substituted with one or more hydrophilic groups as defined herein. In certain embodiments the hydrophilic masking group M includes a nitrogen-containing heterocycle or heteroaryl, amide, carbamate, carboxylic acid, carboxy ester, cyano, amine, ammonium, sulfonamide, sulfonate, urea, thiourea, hydroxyl, thiol, PEG, a zwitterionic group or a sulfonic acid. In some cases, the hydrophilic group includes one or more triazole groups. In some cases, the hydrophilic group includes a PEG moiety. In some cases, the group M includes a nitrogen-containing heterocycle further substituted with PEG. In certain instances, the group M includes more than 1 PEG unit, such as 2, 3, 4, 5, 6, 7, 8, 9 or 10 PEG units. In certain instances, the group M includes less than 10 PEG units, such as 9, 8, 7, 6, 5, 4, 3, 2 or 1 PEG unit. In certain cases, M includes a group composed of 4 PEG units.

In certain embodiments, the hydrophilic masking group M is linked to the hydrophobic group A via a cleavable linker Z, wherein the Z group is a disulfide. In certain embodiments, the group Z is a disulfide group and the group M is a hydrophilic group which is optionally substituted with a group selected from a terminal group, a linker, a chemoselective tag (e.g. configured to conjugate a cell targeting agent or a macromolecule), a linked biomolecule, and a linked cell delivery agent.

In some embodiments, the cleavable linker Z is configured to be cleavable at a first pH range and stable at a second pH range. In some cases, the cleavable linker Z is configured to be cleavable at an acidic pH and stable at a neutral pH. In some cases, cleavable linker Z is configured such that the ratio of the half-life of the cleavage of Z at a first pH to the half-life of the cleavage of Z at a second pH is greater than a certain value, such as 5 or more. In some cases, the first pH is 7.4, the second pH is 5.5, and the ratio is 5 or more, such as 10 or more, 20 or more, 50 or more, 100 or more, 250 or more, or 1000 or more. In some embodiments, Z is configured such that the half-life of the cleavage of Z is greater at a neutral pH than at an acidic pH. In some cases, Z is configured such that the half-life of the cleavage of Z is smaller at a first pH that is more acidic than a second pH.

In some embodiments, the hydrophilic tail group T is a polyethylene glycol (PEG) moiety. Particular examples of hydrophilic tail groups include, but are not limited to a tail group comprising a first molecule selected from polyethylene oxides, oligoethyleneglycols, phosphates (RPO$_4$H—), phosphonates (RPO$_3$H—), boric acid (RBO$_2$H$_2$), carboxylates (RCO$_2$—), sulfates (RSO$_4$—), sulfonates (RSO$_3$—), amines (RNH$_{3+}$), glycerols, sugars such as lactose or derived from hyaluronic acid, polar amino acids, that is optionally conjugated to a residue of a second molecule selected from a polycation, choline, ethanolamine, glycerol, nucleic acid, sugar, inositol, and serine. Here again the tail groups may contain various other modifications, for instance, in the case of the oligoethyleneglycols and polyethylene oxide (PEG) tail groups, such PEG chain may be terminated with a methyl group or have a distal functional group for further modification. In some cases, the PEG chain may be terminated with a group Y, wherein Y is selected from a terminal group, a linker, a chemoselective tag (e.g. configured to conjugate a cell targeting agent or a macromolecule), a member of a specific binding pair, a linked biomolecule, and a linked cell delivery agent. For example, the PEG chain may be terminated with a polycation. In certain cases, the PEG chain is terminated with a chemoselective tag e.g. as defined herein. In certain cases, the chemoselective tag is an amine or a carboxylic acid group. In certain cases, the PEG chain comprises more than 4 PEG units, such as 5, 6, 7, 8, 9 or 10 PEG units. In certain cases, the PEG chain comprises 8 PEG units.

Examples of polycations include, but are not limited to a cationic peptide, a cationic peptide derivative, linear synthetic polymer, branched synthetic polymer, polysaccharide, natural polymer, activated dendrimer and a non-activated dendrimer. In some embodiments, the polycation is a cationic peptide. In some cases, the cationic peptide is polylysine.

Examples of hydrophilic tail groups may also include, but are not limited to, PEG, substituted PEG, thiophosphate, phosphocholine, phosphoglycerol, phosphoethanolamine, phosphoserine, phosphoinositol, ethylphosphosphorylcholine, polyethyleneglycol, polyglycerol, melamine, glucosamine, trimethylamine, spermine, spermidine, and conjugated carboxylates, sulfates, boric acid, sulfonates, sulfates and carbohydrates.

In some embodiments of formula (I), the endosomal disruptor comprises a group Y, wherein Y is selected from a terminal group, a linker, a chemoselective tag (e.g. configured to conjugate a cell targeting agent or a macromolecule), a member of a specific binding pair, linked biomolecule and a linked cell delivery agent. The group Y may be attached to any convenient position of the endosomal disruptor. In some embodiments, the group Y may be a terminal group attached to either of the groups M or T.

In some embodiments of formula (I), the structure of the endosomal disruptor has the formula (II):

wherein:
R$^1$ and R$^{1'}$ are independently selected from alkyl, alkenyl, heterocycle, substituted heterocycle, substituted heterocycle, carbocycle, substituted carbocycle, polyethylene glycol (PEG), substituted PEG, alkyl-Y$^1$ and alkenyl-Y$^1$, wherein Y$^1$ is selected from the group consisting of, heterocycle, substituted heterocycle, heteroaryl, substituted heteroaryl, carbocycle, substituted carbocycle, polyethylene glycol (PEG), modified PEG, and wherein each $Y^1$ group is optionally substituted with one or more additional groups selected from alkyl, substituted alkyl, PEG and modified PEG;

or $R^1$ and $R^{1'}$ together with the carbon to which they are attached form a group selected from heterocycle and substituted heterocycle;

X is O or S;

A is a masked hydrophobic group comprising:
a cyclic group selected from an aryl, a substituted aryl, a heteroaryl, a substituted heteroaryl, a saturated carbocycle, a substituted saturated carbocycle, a heterocycle and a substituted heterocycle; and
a hydrophobic chain;

T is a hydrophilic tail selected from a polyethylene glycol (PEG), a modified PEG, a oligoethyleneglycol, a phosphate, a phosphonate, a boric acid, a carboxylate, a sulfate, a sulfonate, an amine, a glycerol, a sugar, an amino acid, a substituted amino acid; and $Y^1$ is an optional group selected from a terminal group, a linker, a chemoselective tag (e.g. configured to conjugate a cell targeting agent or a macromolecule), a member of a specific binding pair, a linked biomolecule and a linked cell delivery agent;

or a pharmaceutically acceptable salt or a solvate thereof.

In some embodiments of formulae (I) or (II), the structure of the hydrophilic tail has the structure (T1):

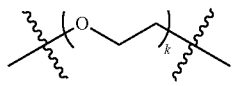

(T1)

wherein:
k is an integer from 1 to 12.

In some embodiments, the hydrophilic tail of formula (T1) can be synthesized using chemical reagents wherein the number of ethylene glycol units, i.e.

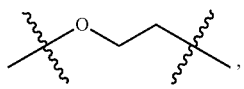 [SMILES: *CCO*]

in molecules of the chemical reagent is not a single number, but rather a distribution of numbers. As such, synthesizing an endosomal disruptor compound of formulae (I) or (II) that contains a hydrophilic tail of structure (T1) that was synthesized with such reagents can yield multiple endosomal disruptors, wherein such endosomal disruptors vary from one another by the number of polyethylene glycol units, i.e. the value of k. In such cases, the hydrophilic tails of endosomal disruptors can be described by the average mass of the hydrophobic tails. As an example, hydrophilic tails of structure (T1) with k values of 10 and 11 will have masses of approximately 440 Da and 484 Da, respectively. Thus, hydrophobic tails with average masses of 462 Da would have an average k value of approximately 10.5. Hence, the hydrophilic tails of endosomal disruptors can be described in regard the exact number of ethylene glycol units or the average mass of the hydrophilic tails.

In some embodiments of formula (I), the structure of the endosomal disruptor has the formula (III):

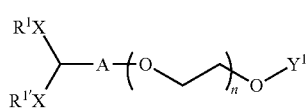

(III)

wherein:
$R^1$ and $R^{1'}$ are independently selected from alkyl, alkenyl, heterocycle, substituted heterocycle, substituted heterocycle, carbocycle, substituted carbocycle, polyethylene glycol (PEG), substituted PEG, alkyl-$Y^1$ and alkenyl-$Y^1$, wherein $Y^1$ is selected from the group consisting of, heterocycle, substituted heterocycle, heteroaryl, substituted heteroaryl, carbocycle, substituted carbocycle, polyethylene glycol (PEG), modified PEG, and wherein each $Y^1$ group is optionally substituted with one or more additional groups selected from alkyl, substituted alkyl, PEG and modified PEG;

or $R^1$ and $R^{1'}$ together with the carbon to which they are attached form a group selected from heterocycle, substituted heterocycle;

X is O or S;

A is a masked hydrophobic group comprising:
a cyclic group selected from an aryl, a substituted aryl, a heteroaryl, a substituted heteroaryl, a saturated carbocycle, a substituted saturated carbocycle, a heterocycle and a substituted heterocycle; and
a hydrophobic chain;

n is an integer such that the mass of the hydrophilic tail is up to 1000 Da, or n is an integer between 0 and 25; and $Y^1$ is selected from H, a terminal group, a linker, a chemoselective tag (e.g. configured to conjugate a cell targeting agent or a macromolecule), a member of a specific binding pair, a linked biomolecule and a linked cell delivery agent, or a pharmaceutically acceptable salt or a solvate thereof.

In certain embodiments, of any of formulae (I) to (III), A comprises an aryl cyclic group of the formula (A1):

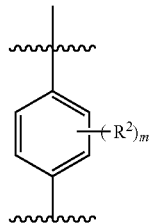

(A1)

In some cases of the formula (A1), m is 0, such that the structure has no $R^2$ substituents. In other cases of formula (A1), m is greater than 0, such as 1, 2, 3 or 4. In such cases, m is equal to the number of $R^2$ substituents. In some cases when m is greater than 0, $R^2$ is selected from the group consisting of OH, alkyl, substituted alkyl, alkenyl, substituted alkenyl, alkoxy, substituted alkoxy, —$OCF_3$, halogen, amine, substituted amine, amide, azide, heterocycle and substituted heterocycle. In certain cases, one or more of the substituents $R^2$ is an electron donating group. Substituents capable of functioning as electron donating groups or electron releasing groups are well known in the field of organic chemistry. An electron donating group donates some of its electron density into a conjugated pi system (e.g. an aromatic ring) via resonance or inductive effects, thus making the pi system more nucleophilic. Examples of electron donating groups include, but are not limited to OH, alkyl, amines, alkoxy, amides and esters.

In certain embodiments, any one or more of the carbon atoms in the phenyl ring of formula (A1) may be replaced by a nitrogen atom. For example, the core of (A1) may be a pyridine, diazine, triazine, tetrazine. In certain cases, the group A comprises a non-aromatic unsaturated 6-memebered cyclic group, wherein any one or more of the carbon atoms may be replaced by a heteroatom (e.g. O, S, N). For example, the core of A may be a pyran, oxazine, thiopyran, thiazine, dioxine, dithiin.

In some cases of any of the formulae (I) to (III), A comprises a carbocycle of the formula (A2):

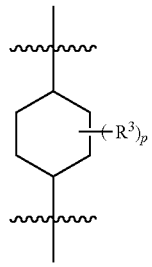

(A2)

In some cases of the formula (A2), p is 0, such that the structure has no $R^3$ substituents. In other cases of formula (A2), p is greater than 0, such as 1, 2, 3, 4, 6, 7 or 8. In some cases when p is greater than 0, $R^3$ is selected from the group consisting of OH, alkyl, substituted alkyl, alkenyl, substituted alkenyl, alkoxy, substituted alkoxy, —OCF$_3$, halogen, amine, substituted amine, amide, azide, heterocycle and substituted heterocycle. In certain cases the formula (A2) includes one or more internal double bonds (e.g. to form a cyclohexene or a diene core).

In certain embodiments, any one or more of the carbon atoms in the carbocycle of formula (A2) may be replaced by a heteroatom (e.g. O, S, N). For example, the core of (A2) may be a piperidine, piperazine, hexahydro-1,3,5-triazine, tetrahydropyran, morpholine, thiane, thiomorpholine, dioxane, dithiane, trioxane, trithiane.

In other cases of any of the formulae (I) to (III), A is an aryl or heteroaryl of the formula (A3) or (A4):

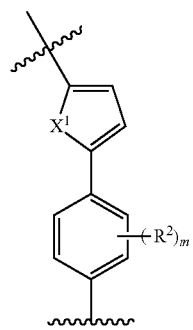

(A3)

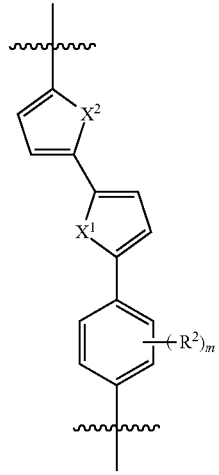

(A4)

In some cases, any of the formula (A3) or (A4), m is 0, such that the structure has no $R^2$ substituents. In other cases of formula (A3) or (A4), m is greater than 0, such as 1, 2, 3 or 4. In some cases when m is greater than 0, $R^2$ is selected from the group consisting of OH, alkyl, substituted alkyl, alkenyl, substituted alkenyl, alkoxy, substituted alkoxy, —OCF$_3$, halogen, amine, substituted amine, amide, azide, heterocycle and substituted heterocycle. In certain cases, one or more of the substituents $R^2$ is an electron donating group including, but are not limited to OH, alkyl, amines, alkoxy, amides and esters.

In certain embodiments, any one or more of the carbon atoms in the phenyl ring of formulae (A3) or (A4) may be replaced by a nitrogen atom. For example, the phenyl core of (A3) or (A4) may be a pyridine, diazine, triazine, tetrazine. In certain cases, the phenyl group of formulae (A3 or A4) may be replaced with a non-aromatic unsaturated 6-memebered cyclic group, wherein any one or more of the carbon atoms may be replaced by a heteroatom, for example to provide a, pyran, oxazine, thiopyran, thiazine, dioxine, dithiin group.

In some cases of the formula (A3) or (A4), $X^1$ and $X^2$ are each independently selected from a carbon or a heteroatom (e.g. S, O, N). In certain cases of formula (A3), $X^1$ is C. In certain cases of formula (A3), $X^1$ is S. In certain cases of the formula (A3), $X^1$ is O. In other cases of formula (A3), $X^1$ is NH. In certain cases of formula (A4), $X^1$ is C. In certain cases of formula (A4), $X^1$ is S. In certain cases of the formula (A4), $X^2$ is O. In other cases of formula (A4), $X^2$ is NH. In certain cases of formula (A4), $X^2$ is C. In certain cases of formula (A4), $X^2$ is S. In certain cases of the formula (A4), $X^2$ is O. In other cases of formula (A4), $X^2$ is NH. In some cases of the formula (A4), both $X^1$ and $X^2$ are S. In other cases of the formula (A4), both $X^1$ and $X^2$ are C. In certain other cases of the formula (A4), both $X^1$ and $X^2$ are O. In other cases of the formula (A4), both $X^1$ and $X^2$ are NH.

In certain embodiments of any of the formulae (I) to (III), A includes a linear or branched hydrophobic chain selected from alkyl, alkenylene, alkynylene, arylene, alkarylene, aralkylene, alkoxy and alkamine. In certain cases, A includes a linear or branched alkoxy group. In certain cases, the alkoxy group is a linear C1-C20 alkoxy group.

In certain embodiments of any of formulae (I) to (III), A includes a hydrophobic chain selected from (B1), (B2) or (B3):

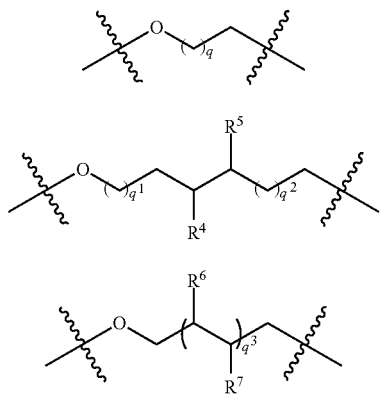

In some cases of the formula (B1), (B2) or (B3), any one of q, q¹, q² and q³ are independently an integer from 1 to 20. In certain cases, any one of q, q¹, q² and q³ are independently an integer from 1 to 15, 1 to 10 or 1 to 5. In certain cases, any one of q, q¹, q² and q³ are independently an integer less than 10, such as 9, 8, 7, 6, 5, 4, 3, 2, 1. In some cases, q is 7, 9, 11, 13, 15, 17, or 19. In some cases, q¹, q² and W are each 1. In some cases, q is 8. In certain cases, q is 9.

In some cases of the formulae (B2) or (B3), any of $R^4$, $R^5$, $R^6$ and $R^7$ are independently selected from alkyl or substituted alkyl. In certain cases, $R^4$, $R^5$, $R^6$ and $R^7$ are each independently a lower alkyl or a substituted lower alkyl, e.g., a C1-C6 lower alkyl, such as methyl, ethyl, propyl, butyl, pentyl or hexyl. In certain cases, $R^4$ and $R^5$ are the same alkyl or substituted alkyl group. In some cases, both $R^4$ and $R^5$ are methyl or ethyl groups. In certain other cases $R^6$ and $R^7$ are the same alkyl or substituted alkyl group. In some cases, both $R^6$ and $R^7$ are methyl or ethyl groups.

In some embodiments of any of formulae (I) to (III), the structure of the endosomal disruptor has the formula (IV):

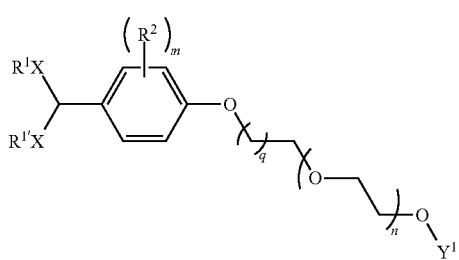

wherein:
$R^1$ and $R^{1'}$ are independently selected from alkyl, alkenyl, heterocycle, substituted heterocycle, substituted heterocycle, carbocycle, substituted carbocycle, polyethylene glycol (PEG), substituted PEG, alkyl-$Y^1$ and alkenyl-$Y^1$, wherein $Y^1$ is selected from the group consisting of heterocycle, substituted heterocycle, heteroaryl, substituted heteroaryl, carbocycle, substituted carbocycle, polyethylene glycol (PEG), modified PEG, and wherein each $Y^1$ group is optionally substituted with one or more additional groups selected from alkyl, substituted alkyl, PEG and modified PEG;

or $R^1$ and $R^{1'}$ together with the carbon to which they are attached form a group selected from heterocycle, substituted heterocycle;
each $R^2$ are independently selected from the group consisting of OH, alkyl, substituted alkyl, alkenyl, substituted alkenyl, alkoxy, substituted alkoxy, —$OCF_3$, halogen, amine, substituted amine, amide, azide, heterocycle and substituted heterocycle;
X is O or S;
m is an integer from 0 to 4;
q is an integer from 1 to 20;
n is an integer such that the mass of the hydrophilic tail is up to 1000 Da, or n is an integer between 1 and 25; and
$Y^1$ is selected from a terminal group, a linker, a chemoselective tag (e.g. configured to conjugate a cell targeting agent or a macromolecule), a member of a specific binding pair, a linked biomolecule and a linked cell delivery agent, or a pharmaceutically acceptable salt or a solvate thereof.

In some cases of the formula (IV), m is 0, such that the structure has no $R^2$ substituents. In other cases of formula (IV), m is greater than 0, such as 1, 2, 3 or 4. In some cases when m is greater than 0, $R^2$ is selected from the group consisting of OH, alkyl, substituted alkyl, alkenyl, substituted alkenyl, alkoxy, substituted alkoxy, —$OCF_3$, halogen, amine, substituted amine, amide, azide, heterocycle and substituted heterocycle. In certain cases, one or more of the substituents $R^2$ is an electron donating group including, but are not limited to OH, alkyl, amines, alkoxy, amides and esters.

In some cases of the formula (IV), q is an integer from 1 to 25, 1 to 10 or 1 to 5. In certain cases, q is 8, 10, 12, 14, or 16. In certain cases, q, is an integer less than 10, such as 9, 8, 7, 6, 5, 4, 3, 2, 1. In some cases, q is 7.

In certain cases of the formula (IV), n is an integer such that the mass of the hydrophobic group is 1000 Da or less, such as 500 Da or less, 450 Da or less, 400 Da or less, 350 Da or less, 300 Da or less, 250 Da or less, 200 Da or less, 150 Da or less, 100 Da or less, or 50 Da or less. In some instances, n is an integer such that the average mass of the hydrophobic group is approximately 350 Da. In some instances, n is an integer such that the average mass of the hydrophobic group is approximately 400 Da. In certain embodiments, n is an integer such that the average mass of the hydrophobic group is 500 Da or more, such as 550 Da or more, 600 Da or more, 650 Da or more, 700 Da or more, 750 Da or more, 800 Da or more, 850 Da or more, 900 Da or more, 950 Da or more, 1000 Da or more, or even more.

In certain cases of the formula (IV), n is an integer from 1 to 25, such as from 2 to 20, from 2 to 15, from 4 to 15, from 4 to 12, from 5 to 12, from 5 to 10, from 6 to 10, or from 7 to 9. In some cases, n is 1, 2, 3, 4, 5, 6, 7, 8, 9, or 10. In some cases, n is 8.

In certain embodiments of any of formulae (I) to (IV), Y or $Y^1$ is a terminal group (e.g. a terminal capping group). In certain embodiments, the terminal group is selected from H, an aryl, a substituted aryl, a heteroaryl, a substituted heteroaryl, an alkyl or a substituted alkyl.

In certain embodiments of any of formulae (I) to (IV), $Y^1$ is an alkyl group. In some cases, $Y^1$ is a lower alkyl or a substituted lower alkyl, e.g., a C1-C6 lower alkyl, such as methyl, ethyl, propyl, butyl, pentyl or hexyl. In certain cases, $Y^1$ is a methyl group.

In certain embodiments of any of formulae (I) to (IV), Y or $Y^1$ is a linker (e.g. as described herein). In certain other embodiments of any of formulae (I) to (IV), Y or $Y^1$ is a chemoselective tag (e.g. configured to conjugate a cell targeting agent or a macromolecule). In some embodiments, the chemoselective tag includes a functional group selected from an amino, a carboxylic acid or a derivative thereof, a thiol, a hydroxyl, a hydrazine, a hydrazide, an azide, an alkyne and a protein reactive group (e g amino-reactive, thiol-reactive, hydroxyl-reactive, imidazolyl-reactive or guanidinyl-reactive). In certain instances of any of formulae (I) to (IV), $Y^1$ is a chemoselective tag comprising a group selected from amino and carboxylic acid. In some cases, the functional group on the chemoselective tag is a terminal group.

In some embodiments of any of formulae (I) to (IV), Y or $Y^1$ is a chemoselective tag configured to conjugate to a peptide, a protein or a polycation selected from a cationic peptide, a cationic peptide derivative, a linear synthetic polymer, branched synthetic polymer, polysaccharide, natural polymer, activated dendrimer and a non-activated dendrimer. In certain instances, the polycation is a cationic peptide (e.g. polylysine).

In certain other embodiments of formula (IV), $Y^1$ is a linked biomolecule or a linked cell delivery agent. For example, $Y^1$ may be selected from a macromolecule as described herein. In other cases, $Y^1$ may be selected from the group including but not limited to, a therapeutically active small molecule, an amino acid, a sugar, a nucleotide, a peptide and a polycation.

In other embodiments of the formula (IV), $Y^1$ is a polycation selected from a cationic peptide, a cationic peptide derivative, linear synthetic polymer, branched synthetic polymer, polysaccharide, natural polymer, activated dendrimer and a non-activated dendrimer. In certain cases, the polycation is a cationic peptide. In some cases, the cationic peptide is polylysine, or a derivative thereof.

The term "cationic peptide" refers to a sequence of amino acids from about 5 to about 50 amino acids in length and preferably from about 15 to about 35 amino acids in length. A peptide is "cationic" if it possesses sufficient positively charged amino acids that have a pKa greater than 9.0. Typically, at least four of the amino acid residues of the cationic peptide can be positively charged, for example, lysine or arginine. "Positively charged" refers to the side chains of the amino acid residues which have a net positive charge at pH 7.0. Examples of naturally occurring cationic peptides include defensins, magainins, melittin, and cecropins, and analogs thereof.

In certain embodiments of the formula (IV), each X group is O so as to form an acetal masking group. In some cases, the acetal masking group is substituted with one or more hydrophilic groups (e.g. $R^1$ and $R^{1'}$). In certain embodiments the groups $R^1$ and $R^{1'}$ include nitrogen-containing heterocycle or heteroaryl, amide, carbamate, carboxylic acid, carboxy ester, cyano, amine, ammonium, sulfonamide, sulfonate, urea, thiourea, hydroxyl, thiol, PEG, a zwitterionic group or a sulfonic acid substituent. In some cases, the groups $R^1$ and $R^{1'}$ include one or more triazole groups. In some cases, the groups $R^1$ and $R^{1'}$ include a PEG moiety. In some cases, the groups $R^1$ and $R^{1'}$ include a nitrogen-containing heterocycle further substituted with PEG. In some cases, the $R^1$ and $R^{1'}$ groups can include ethyleneimine groups.

In some embodiments of any of the formulae (II) to (IV), each $R^1$ and $R^{1'}$ group are independently selected from:

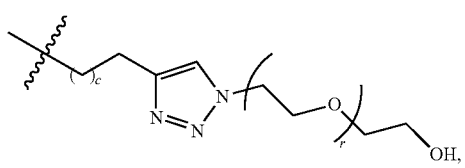

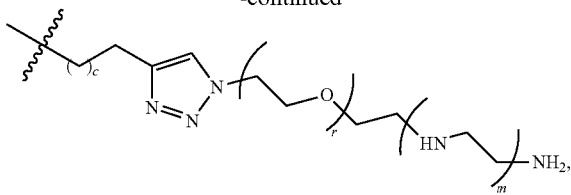

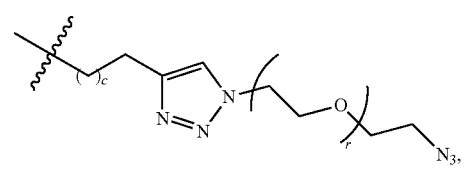

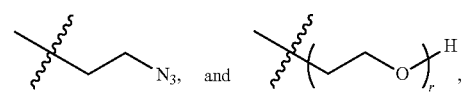

wherein r is an integer from 0 to 20, c is an integer from 1 to 25, and m is an integer from 0 to 15. In some cases, r is an integer less than 10, such as 9, 8, 7, 6, 5, 4, 3, 2, or 1. In certain instances, r is 3. In certain instances, r is 4. In some cases, c is an integer less than 10, such as such as 9, 8, 7, 6, 5, 4, 3, 2, or 1. In some cases, c is an integer from 1 to 5. In certain instances, c is 1. In some cases, m is 0. In some cases, m is an integer from 1 to 5.

In some embodiments of any of the formulae (II) to (IV), each $R^1$ and $R^{1'}$ group are independently selected from:

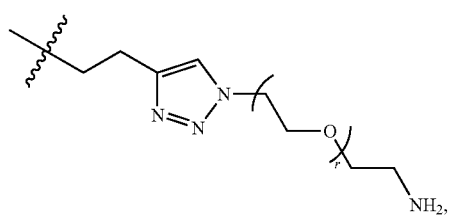

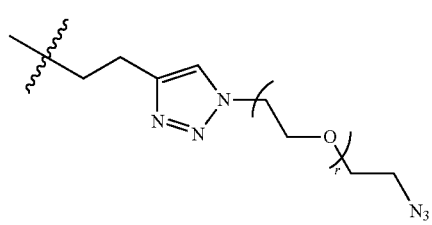

-continued

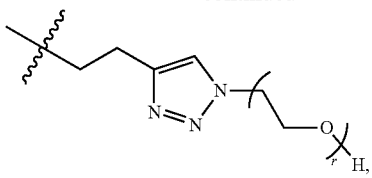

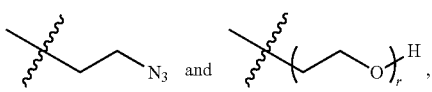

wherein r is an integer from 1 to 10. In some cases, r is an integer less than 10, such as 9, 8, 7, 6, 5, 4, 3, 2, or 1. In certain instances, r is 3. In certain instances, r is 4.

In certain cases of any of the formulae (II) to (IV), $R^1$ and $R^{1'}$ are both:

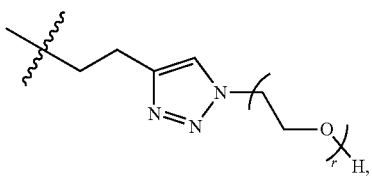

and r is an integer from 1 to 10. In some cases, r is an integer less than 10, such as 9, 8, 7, 6, 5, 4, 3, 2 or 1. In certain instances, r is 3. In certain instances, r is 4.

In certain cases of any of the formulae (II) to (IV), $R^1$ and $R^{1'}$ are both:

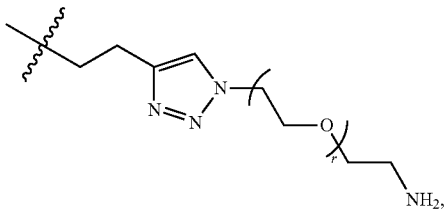

and r is an integer from 1 to 10. In some cases, r is an integer less than 10, such as 9, 8, 7, 6, 5, 4, 3, 2 or 1. In certain instances, r is 3. In certain instances, r is 4.

In some embodiments of any of formulae (I) to (IV), the structure of the endosomal disruptor has the formula (V):

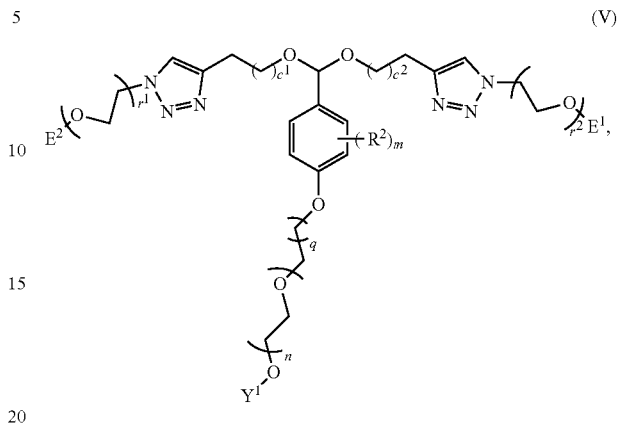

wherein:

$c^1$ is an integer from 1 to 5, $c^2$ is an integer from 1 to 5, $r^1$ is an integer from 1 to 6, $r^2$ is an integer from 1 to 6, q is an integer from 1 to 19, $E^1$ is H or —$CH_2$—$CH_2$—$NH_2$, $E^2$ is H or —$CH_2$—$CH_2$—$NH_2$, n is an integer such that the mass of the hydrophilic tail is 1000 Da or less, or n is an integer between 1 and 25, and m is an integer between 0 and 4, wherein m is the number of $R^2$ substituents on the aryl ring, wherein each $R^2$ substituent is selected from the group consisting of OH, alkyl, substituted alkyl, alkenyl, substituted alkenyl, alkoxy, substituted alkoxy, —$OCF_3$, halogen, amine, substituted amine, amide, azide, heterocycle and substituted heterocycle.

In some embodiments of formula (V), $c^1$ is 2. In some embodiments of formula (V), $c^2$ is 1. In some embodiments of formula (V), $r^1$ is an integer from 2 to 4, such as 3 or 4. In some embodiments of formula (V), $r^2$ is an integer from 2 to 4, such as 3 or 4. In some embodiments of formula (V), q is an integer from 7 to 15, such as from 9 to 15. In some embodiments of formula (V), q is 9, 11, or 15. In some embodiments of formula (V), $E^1$ is H. In some embodiments of formula (V), $E^1$ is —$CH_2$—$CH_2$—$NH_2$. In some embodiments of formula (V), $E^2$ is H. In some embodiments of formula (V), $E^2$ is —$CH_2$—$CH_2$—$NH_2$. In some embodiments of formula (V), n is an integer such that the mass of the hydrophilic group is 1000 Da or less, such as 500 Da or less, 450 Da or less, 400 Da or less, 350 Da or less, 300 Da or less, 250 Da or less, 200 Da or less, 150 Da or less, 100 Da or less, or 50 Da or less. In some embodiments of formula (V), n is an integer from 2 to 20, such as from 2 to 15, from 4 to 15, from 4 to 12, from 5 to 12, from 5 to 10, from 6 to 10, or from 7 to 9. In some embodiments of formula (V), n is 1, 2, 3, 4, 5, 6, 7, 8, 9, 10, 11, or 12. In some embodiments of formula (V), n is 8. In some embodiments of formula (V), m is zero.

In some embodiments, the endosomal disruptor is described by the structure of compound (1), (2), or (3):
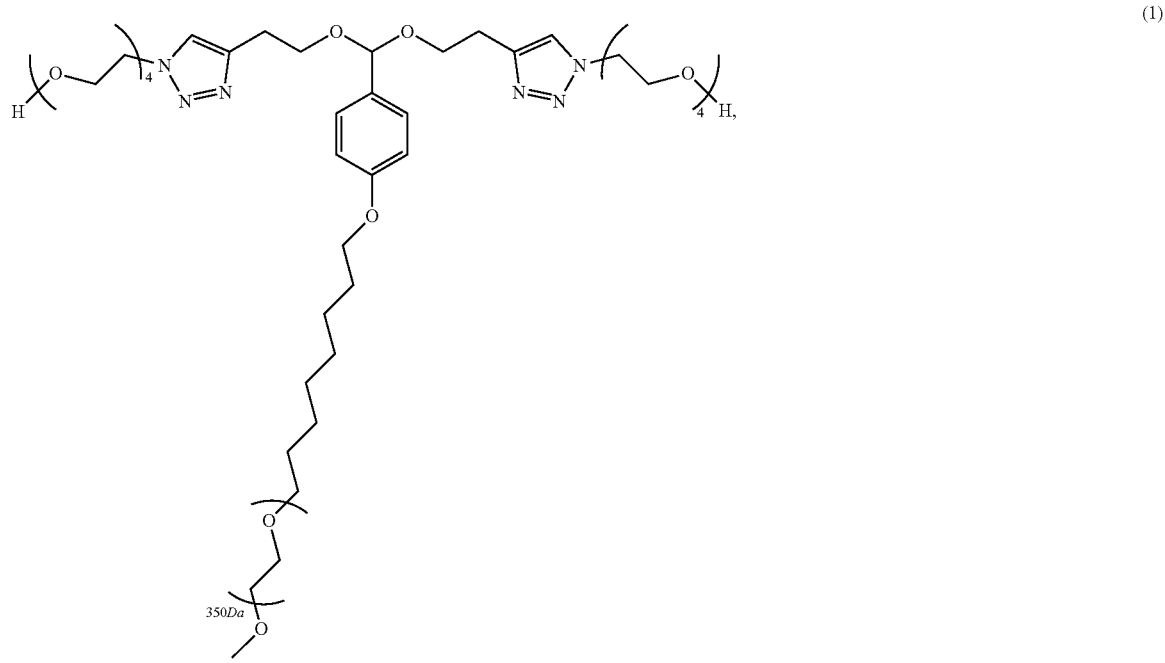
(1)
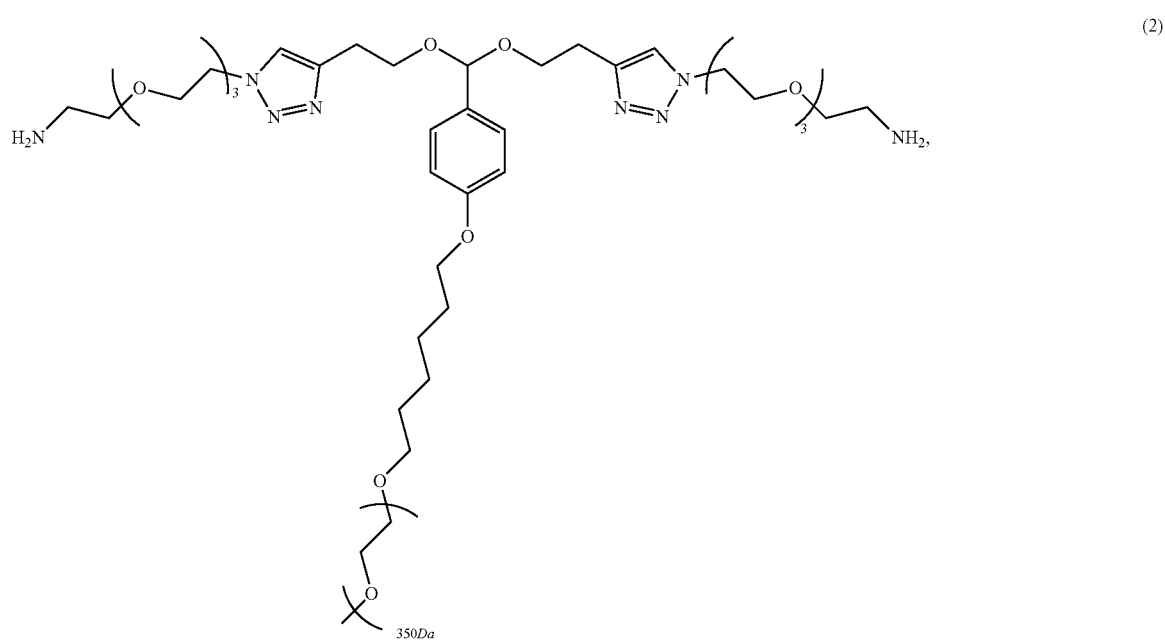
(2)

-continued

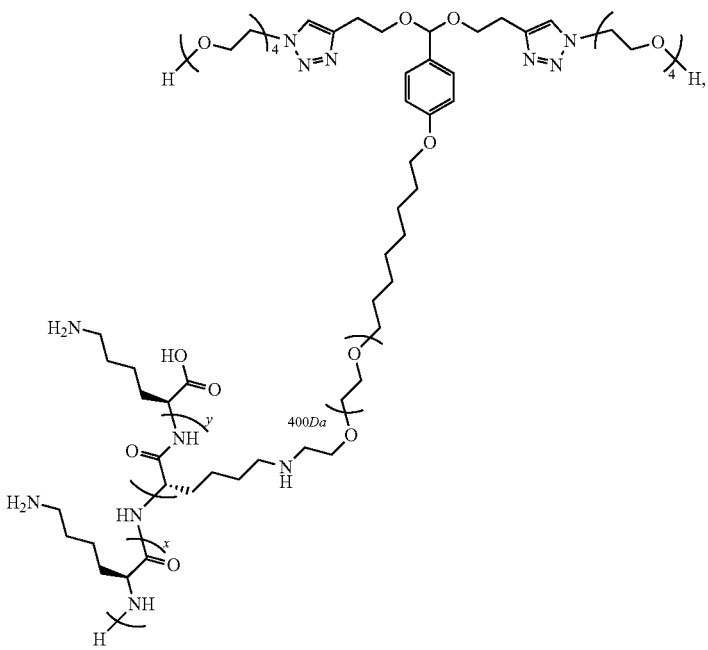

(3)

wherein x and y combined equal an integer from 25 to 30.

In some cases, the subject endosomal disruptor is of the formula (V)

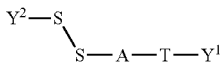

(V)

wherein:

S—S represents a disulfide linker;

$Y^Z$ is a hydrophilic group optionally substituted with a group selected from a terminal group, a linker, a chemoselective tag (e.g. configured to conjugate a cell targeting agent or a macromolecule), a member of a specific binding pair, a linked biomolecule and a linked cell delivery agent;

A is a masked hydrophobic group comprising:

a cyclic group selected from an aryl, a substituted aryl, a heteroaryl, a substituted heteroaryl, a saturated carbocycle, a substituted saturated carbocycle, a heterocycle and a substituted heterocycle; and a hydrophobic chain;

T is a hydrophilic tail selected from a polyethylene glycol (PEG), a modified PEG, a oligoethyleneglycol, a phosphate, a phosphonate, a boric acid, a carboxylate, a sulfate, a sulfonate, an amine, an amide, a glycerol, a sugar, an amino acid, a substituted amino acid; and $Y^1$ is an optional group selected from a terminal group, a linker, a chemoselective tag (e.g. configured to conjugate a cell targeting agent or a macromolecule), a member of a specific binding pair, a linked biomolecule and a linked cell delivery agent; or a pharmaceutically acceptable salt or a solvate thereof.

In some embodiments of formula (V), the endosomal disruptor has the formula (VI):

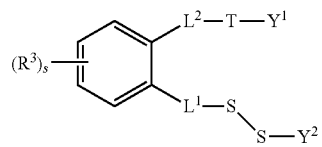

(VI)

wherein:

$L^1$ and $L^2$ are each independently selected from, a covalent bond, an amide group, an ester group, a ketone group and a hydrophobic chain, wherein at least one of $L^1$ or $L^2$ is a hydrophobic chain;

S—S represents a disulfide linker;

$Y^Z$ is selected from a hydrophilic group optionally substituted with a group selected from a terminal group, a linker, a chemoselective tag (e.g. configured to conjugate a cell targeting agent or a macromolecule), a member of a specific binding pair, a linked biomolecule and a linked cell delivery agent;

each $R^3$ are independently selected from the group consisting of OH, alkyl, substituted alkyl, alkenyl, substituted alkenyl, alkoxy, substituted alkoxy, —OCF$_3$, halogen, amine, substituted amine, amide, azide, heterocycle and substituted heterocycle;

T is a hydrophilic tail selected from a polyethylene glycol (PEG), a modified PEG, a oligoethyleneglycol, a phosphate, a phosphonate, a boric acid, a carboxylate, a sulfate, a sulfonate, an amine, an amide, a glycerol, a sugar, an amino acid, a substituted amino acid;

$Y^1$ is an optional group selected from a terminal group, a linker, a chemoselective tag (e.g. configured to conjugate a cell targeting agent or a macromolecule), a member of a specific binding pair, a member of a specific binding pair, a linked biomolecule and a linked cell delivery agent; and s is an integer from 0 to 4,
or a pharmaceutically acceptable salt or a solvate thereof.

In some embodiments of formula (VI), the endosomal disruptor has the formula (VII):

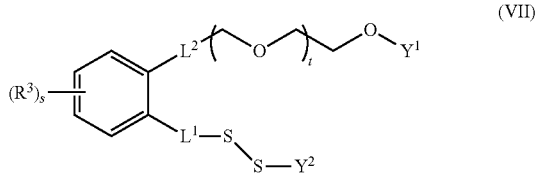

(VII)

wherein:
L¹ and L² are each independently selected from, a covalent bond, an amide group, an ester group, a ketone group, an amine group, an alkoxy group, and a hydrophobic chain, wherein at least one
of L¹ or L² is a hydrophobic chain;
S—S represents a disulfide linker;
$Y^Z$ is selected from a hydrophilic group optionally substituted with a group selected from a terminal group, a linker, a chemoselective tag (e.g. configured to conjugate a cell targeting agent or a macromolecule), a a member of a specific binding pair, linked biomolecule and a linked cell delivery agent;
each R³ are independently selected from the group consisting of OH, alkyl, substituted alkyl, alkenyl, substituted alkenyl, alkoxy, substituted alkoxy, —OCF₃, halogen, amine, substituted amine, amide, azide, heterocycle and substituted heterocycle;
Y¹ is selected from H, a terminal group, a linker, a chemoselective tag (e.g. configured to conjugate a cell targeting agent or a macromolecule), a member of a specific binding pair, a linked biomolecule and a linked cell delivery agent;
s is an integer from 0 to 4; and
t is an integer up to 2000 Da,
or a pharmaceutically acceptable salt or a solvate thereof.

In certain embodiments, of the formulae (VI) or (VII), at least one of L¹ or L² is a linear or branched hydrophobic chain selected from amide, ester, ketone, alkyl, alkenylene, alkynylene, arylene, alkarylene, aralkylene, alkoxy and alkamine. In certain cases, L¹ is a linear or branched alkyl or alkamine group, wherein the alkyl or alkamine includes a C2-C10 alkyl chain. In certain cases, the L¹ is a linear alkamine group including a C8 alkyl chain.

In certain embodiments of formula (VII), the endosomal disruptor has the formula (VIII):

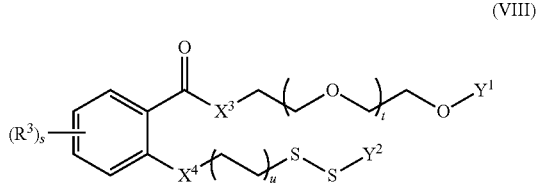

(VIII)

wherein:
X³ and X⁴ are each independently selected from CH₂, NH and O;
each R³ are independently selected from the group consisting of OH, alkyl, substituted alkyl, alkenyl, substituted alkenyl, alkoxy, substituted alkoxy, —OCF₃, halogen, amine, substituted amine, amide, azide, heterocycle and substituted heterocycle;
Y¹ is selected from H, a terminal group, a linker, a chemoselective tag (e.g. configured to conjugate a cell targeting agent or a macromolecule), a member of a specific binding pair, a linked biomolecule and a linked cell delivery agent;
Y² is selected from a hydrophilic group optionally substituted with a group selected from a terminal group, a linker, a chemoselective tag (e.g. configured to conjugate a cell targeting agent or a macromolecule), a member of a specific binding pair, a linked biomolecule and a linked cell delivery agent;
s is an integer from 0 to 4;
t is an integer such that the mass of the group described by t is up to 2000 Da, or t is an integer from 0 to 1 to 50; and
u is an integer from 1 to 10,
or a pharmaceutically acceptable salt or a solvate thereof.

In certain embodiments of formula (VIII), the group X³ is NH. In other cases, the group X³ is CH₂. In other cases, the group X³ is an oxygen atom.

In certain embodiments of formula (VIII), the group X⁴ is NH. In other cases, the group X⁴ is CH₂. In other cases, the group X⁴ is an oxygen atom. In certain embodiments, both X³ and X⁴ are NH. In certain embodiments both X³ and X⁴ are CH₂. In other cases, both X³ and X⁴ are oxygen atoms.

In certain embodiments of any of formulae (V) to (VIII), Y¹ is selected from a terminal group, a linker, a chemoselective tag, a linked biomolecule or a linked cell delivery agent (e.g. as described herein. In certain cases, Y¹ is a terminal group selected from H, an aryl, a substituted aryl, a heteroaryl, a substituted heteroaryl, an alkyl or a substituted alkyl. In certain cases, Y¹ is an alkyl group. In some cases, Y¹ is a lower alkyl or a substituted lower alkyl, e.g., a C1-C6 lower alkyl, such as methyl, ethyl, propyl, butyl, pentyl or hexyl. In certain cases, Y¹ is a methyl group.

In certain embodiments of any of formulae (V) to (VIII), Y² is a hydrophilic group as defined herein. In certain instances, the hydrophilic group includes a nitrogen-containing heterocycle or heteroaryl, amide, carbamate, carboxylic acid, carboxy ester, cyano, amine, ammonium, sulfonamide, sulfonate, urea, thiourea, hydroxyl, thiol, PEG, modified PEG, a zwitterionic group or a sulfonic acid. In certain cases, the hydrophilic group includes a carboxylic acid group.

In certain embodiments of any of formulae (V) to (VIII), Y² is a hydrophilic group (e.g. as defined herein) substituted with a group selected from a terminal group, a linker, a chemoselective tag (e.g. configured to conjugate a cell targeting agent or a macromolecule), a member of a specific binding pair, a linked biomolecule and a linked cell delivery agent. In certain cases, Y² is a group including a carboxylic acid or an amine group. In certain cases, Y² includes a terminal carboxylic acid or amine group. In some cases, Y² is:

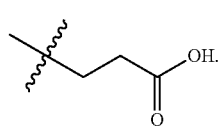 [SMILES: *CCC(=O)O]

In some embodiments, the endosomal disruptor is described by the structure of compound (3):

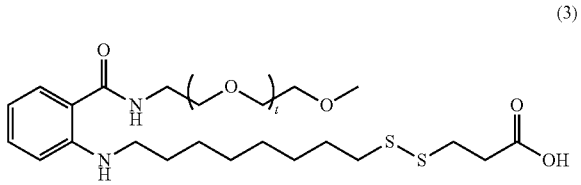

(3)

wherein t is an integer such that the group described by t has a mass of approximately 1000 Da, or t is an integer from 20 to 25.

In certain embodiments, the endosomal disruptor is described by the structure of compound 1, 2 or 3 or by the formulae (I) to (VIII). It is understood that any of the subject structures or formulae may be present in a salt form. In some cases, the salt form of the compound is a pharmaceutically acceptable salt.

Aspects of the present disclosure include endosomal disruptors (e.g., as described herein), salts thereof (e.g., pharmaceutically acceptable salts), and/or solvate, hydrate forms thereof. Any of the subject endosomal disruptors may also be used in combination with their unmasked hydrophobic endosomal disruptor equivalents. For example, in the case of compounds 1 or 2, the unmasked equivalent is represented by the corresponding aldehyde (e.g. as obtained after hydrolysis of the acetal linkage). In addition, it is understood that, in any compound described herein having one or more chiral centers, if an absolute stereochemistry is not expressly indicated, then each center may independently be of R-configuration or S-configuration or a mixture thereof. It will be appreciated that all permutations of salts, solvates, hydrates, prodrugs and stereoisomers are meant to be encompassed by the present disclosure.

The term "solvate" as used herein refers to a complex or aggregate formed by one or more molecules of a solute, e.g. a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

In some embodiments, the subject compounds are provided by oral dosing and absorbed into the bloodstream. In some embodiments, the oral bioavailability of the subject compounds is 30% or more. Modifications may be made to the subject compounds or their formulations using any convenient methods to increase absorption across the gut lumen or their bioavailability.

As outlined above, the subject endosomal disruptors are useful for facilitating delivery of a macromolecule to the cytoplasm of a cell. The presence of the masked cleavable linker on the endosomal disrupting surfactant (e.g. the masked acetal moiety in compounds 1 and 2 or the masked disulfide of compound 3) prevent the subject endosomal disruptors from disrupting the membrane, as the hydrophilic masking groups prevent the hydrophobic domain from inserting into the cell membranes. However, upon entering the endosomal compartment, the cleavable linker (e.g. the acetal or disulfide) is cleaved (e.g. by hydrolysis or reduction), thereby freeing and unmasking the endosomal disruptive surfactant. The unmasked endosomal disruptive surfactant triggers endosomal disruption, allowing release of any co-delivered macromolecule into the cytoplasm.

In certain cases, the cleavable linker of the subject endosomal disruptors hydrolyzes at acidic pH (e.g. the acidic conditions within the endosomal compartment). As described above, the expression "acidic pH" means a pH of 6.0 or less (e.g., less than about 6.0, less than about 5.5, less than about 5.0, etc.). The expression "acidic pH" includes pH values of about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, 4.9, 4.85, 4.80, 4.75, 4.7, 4.65, 4.6, 4.55, 4.5 or less. In certain cases, the cleavable linker is cleaved rapidly at a pH of about 5.0, but slowly at a pH of about 7.4. Accordingly, any convenient cleavable linker which hydrolyzes under acidic conditions to release an endosomal disruptive surfactant (e.g. as described herein) may find use in the present invention. In certain instances, the cleavable linker is an aldehyde masking group (e.g. an acetal group).

In certain instances, the cleavable linker of the subject endosomal disruptors is cleaved under reducing conditions. In certain embodiments the subject endosomal disruptor is cleaved by a reducing agent at acidic pH (e.g. the acidic conditions within the endosomal compartment). In certain cases, the cleavable linker is cleaved rapidly by glutathione reduction at the acidic pH of the endosomal compartment. Accordingly, any convenient cleavable linker that is capable of cleavage under reducing conditions may find use in an endosomal disruptor of the present disclosure. In certain instances, the cleavable linker is a disulfide. However, it will be understood that any convenient cleavable linker that is capable of cleavage within the endosomal compartment can be utilized in the subject endosomal disruptors.

In some cases, the cleavable linker of the subject endosomal disruptors cleaves within a timescale of 1 to 20 minutes at acidic pH. In some cases, the cleavable linker cleaves in less than 20 minutes, such as 15 minutes or less, 10 minutes or less, 5 minutes or less, 3 minutes or less. In certain embodiments, the cleavable linker is cleaved in a timescale from 10 to 15 minutes or less, such as 5 to 10 minutes or less. In some cases, the cleavable linker of the subject endosomal disruptors has a half-life of 2.5 minutes or less at a pH of about 5.

By contrast, at neutral pH, the cleavable linkers of the subject endosomal disruptors may be stable for several hours. As described above, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In some cases, the subject unmasked endosomal disruptive surfactant compounds are metabolically stable (e.g., remain substantially intact in vivo during the half-life of the compound). In certain embodiments, the compounds have a half-life (e.g., an in vivo half-life) of 5 minutes or more, such as 10 minutes or more, 12 minutes or more, 15 minutes or more, 20 minutes or more, 30 minutes or more, 60 minutes or more, 2 hours or more, 6 hours or more, 12 hours or more, 24 hours or more, or even more. In some embodiments, the cleavable linker of the subject endosomal disruptors has a half-life of greater than 4 hours at a pH of about 7.4.

In some cases, the half-life of the cleavage of the cleavable linker of the endosomal disruptors at acidic pH is between 1 and 20 minutes. In some cases, the half-life of the cleavage of the cleavable linker of the endosomal disruptors at acidic pH is 20 minutes or less, such as 15 minutes or less, 10 minutes or less, 5 minutes or less, 3 minutes or less. In certain embodiments, the half-life of the cleavage of the cleavable linker of the endosomal disruptors at acidic pH is between 10 and 15 minutes, inclusive, or between 5 and 10 minutes, inclusive. In some cases, the half-life of the cleavage of the cleavable linker of the endosomal disruptors at a pH of about 5 is 2.5 minutes or less.

In some cases, the half-life of the cleavage of the cleavable linker of the endosomal disruptors at neutral pH is 20 minutes or more, such as 30 minutes or more, 45 minutes or more, 60 minutes or more 120 minutes or more, 240 minutes or more, or 480 minutes or more.

Accordingly, pH-dependent selective disruption of endosomal membrane compartments may be achieved with the subject endosomal disruptors.

In some cases, an endosomal disruptor of the present disclosure has a mass of less than 2000 Daltons (Da), e.g., less than 2000 Da, or less than 1500 Da.

An endosomal disruptor of the present disclosure provides for increased efficiency of delivery of a macromolecule to the cytoplasm of a eukaryotic cell and/or to a subcellular compartment, other than an endosome, of a eukaryotic cell.

For example, where a composition of the present disclosure comprises: a) an endosomal disruptor; b) a gene-editing enzyme, or a nucleic acid comprising a nucleotide sequence encoding a gene-editing enzyme; and c) a guide RNA, the endosomal disruptor provides for increased gene editing efficiency, compared to the gene editing efficiency provided for by a control composition not including the endosomal disruptor. The increased gene editing efficiency reflects the increased degree of release from an endosome of the gene-editing composition (a gene-editing enzyme, or a nucleic acid comprising a nucleotide sequence encoding a gene-editing enzyme; and guide RNA).

In some cases, an endosomal disruptor provides for increased endosomal escape, and therefore increased delivery of a macromolecule(s) (e.g., a gene-editing enzyme, or a nucleic acid comprising a nucleotide sequence encoding a gene-editing enzyme; a guide RNA; a donor DNA template) to the nucleus of a cell. For example, an endosomal disruptor, when formulated with a macromolecule(s) (e.g., a gene-editing enzyme, or a nucleic acid comprising a nucleotide sequence encoding a gene-editing enzyme; a guide RNA; a donor DNA template) provides for at least 20%, at least 25%, at least at least 50%, at least 2-fold, at least 2.5-fold, at least 5-fold, at least 10-fold, or more than 10-fold, increased delivery of the macromolecule(s) to the nucleus of a cell, compared the delivery of the macromolecule(s) to the nucleus in the absence of the endosomal disruptor.

As noted above, in some cases, an endosomal disruptor of the present disclosure includes a Y moiety, where the Y moiety is an optional group selected from a terminal group, a linker, a chemoselective tag (e.g. configured to conjugate a cell targeting agent or a macromolecule), a linked biomolecule, a member of a specific binding pair, and a linked cell delivery agent. In some cases, Y a member of a specific binding pair. Suitable specific binding pairs include, e.g., biotin-streptavidin; antibody-antigen; and the like. In some cases, Y is biotin. In some cases, Y is streptavidin. In some cases, Y is a cell targeting moiety. In some cases, Y is a biomolecule, where the biomolecule is a polypeptide. In some cases, Y is a biomolecule, where the biomolecule is a nucleic acid. In some cases, Y is a moiety that provides for linkage of the endosomal disruptor to a biomolecule such as a polypeptide. In some cases, Y is a moiety that provides for linkage of the endosomal disruptor to a biomolecule such as a nucleic acid. Suitable polypeptides and nucleic acids are described below.

Compositions Comprising an Endosomal Disruptor and a Macromolecule

The present disclosure provides compositions comprising: a) an endosomal disruptor of the present disclosure; and b) a macromolecule. In some cases, the macromolecule is non-covalently associated with the endosomal disruptor.

The present disclosure provides compositions comprising: a) an endosomal disruptor of the present disclosure; and b) a macromolecule. In some cases, the macromolecule is covalently linked to the endosomal disruptor. In some cases, the macromolecule is covalently linked to the endosomal disruptor via a linker. macromolecule is covalently linked to the endosomal disruptor via a cleavable linker.

Suitable macromolecules include polypeptides and polynucleotides.

In some cases, a composition of the present disclosure comprises: a) an endosomal disruptor of the present disclosure; and b) one or components selected from: i) a CRISPR/Cas effector polypeptide, or a nucleic acid comprising a nucleotide sequence encoding a CRISPR/Cas effector polypeptide; ii) a guide RNA that binds to a CRISPR/Cas effector polypeptide, or a nucleic acid comprising a nucleotide sequence encoding a guide RNA that binds to a CRISPR/Cas effector polypeptide; and iii) a donor nucleic acid. In some cases, the one or more components are non-covalently associated with the endosomal disruptor. In some cases, one or more components selected from: i) a CRISPR/Cas effector polypeptide, or a nucleic acid comprising a nucleotide sequence encoding a CRISPR/Cas effector polypeptide; ii) a guide RNA that binds to a CRISPR/Cas effector polypeptide, or a nucleic acid comprising a nucleotide sequence encoding a guide RNA that binds to a CRISPR/Cas effector polypeptide; and iii) a donor nucleic acid are covalently linked to the endosomal disruptor. For example, in some cases, a CRISPR/Cas effector polypeptide is covalently linked to the endosomal disruptor. As another example, in some cases, a guide RNA is covalently linked to the endosomal disruptor. As another example, in some cases, both a CRISPR/Cas effector polypeptide and a guide RNA are covalently linked to the endosomal disruptor. Covalent linkage can be direct or via a linker, e.g., a cleavable linker.

Polypeptides

Suitable polypeptides include, e.g., an enzyme, a hormone, a polypeptide chemotherapeutic agent, an immunotherapeutic agent, a gene editing polypeptide, a transcriptional modulator, a translational modulator, a post-translational modulator, a modulator of protein expression, a modulator of protein function, an antibody, a receptor, a ligand, a cytokine, a chemokine, and the like. As used herein, the term "polypeptide" includes polypeptides with any co-translational or post-translational modification such as, for example, glycoproteins, lipoproteins (e.g., high density lipoprotein (HDL), low density lipoprotein (LDL), etc.), glycolipoproteins, etc. In some cases, the macromolecule is an enzyme. Any enzyme suitable for delivery into a cell may be used with the subject methods and compositions. Enzymes of interest may include, for example, enzymes that are present and/or in the cytoplasm or nucleus of a cell.

DNA Modifying Enzymes

In some cases, the polypeptide is a DNA modifying enzyme, e.g., a gene-editing enzyme. In some cases, the polypeptide is a nuclease. In some cases, the nuclease is a site-specific endonuclease. A site-specific endonuclease provides for site-specific knock-down of gene function, e.g., where the endonuclease knocks out an allele associated with a disease. For example, where a dominant allele encodes a defective copy of a gene that, when wild-type, is a neural structural protein and/or provides for normal neural function, a site-specific endonuclease can be targeted to the defective allele and knock out the defective allele. In some cases, a site-specific endonuclease is an RNA-guided endonuclease.

Site-specific endonucleases that are suitable for use include, e.g., zinc finger nucleases (ZFNs); meganucleases; and transcription activator-like effector nucleases (TALENs), where such site-specific endonucleases are non-naturally occurring and are modified to target a specific gene. Such site-specific nucleases can be engineered to cut specific locations within a genome, and non-homologous end joining can then repair the break while inserting or deleting several nucleotides. Such site-specific endonucleases (also referred to as "INDELs") then throw the protein out of frame and effectively knock out the gene. See, e.g., U.S. Patent Publication No. 2011/0301073. Suitable site-specific endonucleases include engineered meganuclease re-engineered homing endonucleases. Suitable endonucleases include an I-TevI nuclease. Suitable meganucleases include I-SceI (see, e.g., Bellaiche et al. (1999) Genetics 152:1037); and I-CreI (see, e.g., Heath et al. (1997) Nature Structural Biology 4:468).

Gene-Editing Enzymes

In certain embodiments, the polypeptide includes a gene editing polypeptide, e.g., a gene-editing enzyme (also referred to as a "CRISPR/Cas effector polypeptide"). In some instances, the gene-editing enzyme is an RNA-guided endonuclease. An RNA-guided endonuclease is also referred to herein as a "genome editing nuclease." Examples of RNA-guided endonucleases are CRISPR/Cas endonucleases (e.g., class 2 CRISPR/Cas endonucleases such as a type II, type V, or type VI CRISPR/Cas endonucleases). A suitable genome editing nuclease is a CRISPR/Cas endonuclease (e.g., a class 2 CRISPR/Cas endonuclease such as a type II, type V, or type VI CRISPR/Cas endonuclease). In some cases, a suitable RNA-guided endonuclease is a class 2 CRISPR/Cas endonuclease. In some cases, a suitable RNA-guided endonuclease is a class 2 type II CRISPR/Cas endonuclease (e.g., a Cas9 protein). In some cases, a genome targeting composition includes a class 2 type V CRISPR/Cas endonuclease (e.g., a Cpf1 protein, a C2c1 protein, or a C2c3 protein). In some cases, a suitable RNA-guided endonuclease is a class 2 type VI CRISPR/Cas endonuclease (e.g., a C2c2 protein; also referred to as a "Cas13a" protein). Also suitable for use is a CasX protein. Also suitable for use is a CasY protein. CasX and CasY polypeptides are described in Burstein et al. (2017) Nature 542:237.

RNA-mediated adaptive immune systems in bacteria and archaea rely on Clustered Regularly Interspaced Short Palindromic Repeat (CRISPR) genomic loci and CRISPR-associated (Cas) proteins that function together to provide protection from invading viruses and plasmids. In class 2 CRISPR systems, the functions of the effector complex (e.g., the cleavage of target DNA) are carried out by a single endonuclease (e.g., see Zetsche et al., Cell. 2015 Oct. 22; 163(3):759-71; Makarova et al., Nat Rev Microbiol. 2015 November; 13(11):722-36; Shmakov et al., Mol Cell. 2015 Nov 5; 60(3):385-97); and Shmakov et al. (2017) *Nature Reviews Microbiology* 15:169. As such, the term "class 2 CRISPR/Cas protein" is used herein to encompass the endonuclease (the target nucleic acid cleaving protein) from class 2 CRISPR systems. Thus, the term "class 2 CRISPR/Cas endonuclease" as used herein encompasses type II CRISPR/Cas proteins (e.g., Cas9); type V-A CRISPR/Cas proteins (e.g., Cpf1 (also referred to a "Cas12a")); type V-B CRISPR/Cas proteins (e.g., C2c1 (also referred to as "Cas12b")); type V-C CRISPR/Cas proteins (e.g., C2c3 (also referred to as "Cas12c")); type V-U1 CRISPR/Cas proteins (e.g., C2c4); type V-U2 CRISPR/Cas proteins (e.g., C2c8); type V-U5 CRISPR/Cas proteins (e.g., C2c5); type V-U4 CRISPR/Cas proteins (e.g., C2c9); type V-U3 CRISPR/Cas proteins (e.g., C2c10); type VI-A CRISPR/Cas proteins (e.g., C2c2 (also known as "Cas13a")); type VI-B CRISPR/Cas proteins (e.g., Cas13b (also known as C2c4)); and type VI-C CRISPR/Cas proteins (e.g., Cas13c (also known as C2c7)). To date, class 2 CRISPR/Cas proteins encompass type II, type V, and type VI CRISPR/Cas proteins, but the term is also meant to encompass any class 2 CRISPR/Cas protein suitable for binding to a corresponding guide RNA and forming an RNP complex.

In some cases, the genome-editing endonuclease is a Type II CRISPR/Cas endonuclease. In some cases, the genome-editing endonuclease is a Cas9 polypeptide. The Cas9 protein is guided to a target site (e.g., stabilized at a target site) within a target nucleic acid sequence (e.g., a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA.

In natural Type II CRISPR/Cas systems, Cas9 functions as an RNA-guided endonuclease that uses a dual-guide RNA having a crRNA and trans-activating crRNA (tracrRNA) for target recognition and cleavage by a mechanism involving two nuclease active sites in Cas9 that together generate double-stranded DNA breaks (DSBs), or can individually generate single-stranded DNA breaks (SSBs). The Type II CRISPR endonuclease Cas9 and engineered dual-guide RNA (dgRNA) or single-guide RNA (sgRNA) form a ribonucleoprotein (RNP) complex that can be targeted to a desired DNA sequence. Guided by a dual-RNA complex or a chimeric single-guide RNA, Cas9 generates site-specific DSBs or SSBs within double-stranded DNA (dsDNA) target nucleic acids, which are repaired either by non-homologous end joining (NHEJ) or homology-directed recombination (HDR).

A type II CRISPR/Cas endonuclease is a type of class 2 CRISPR/Cas endonuclease. In some cases, the type II CRISPR/Cas endonuclease is a Cas9 protein. A Cas9 protein forms a complex with a Cas9 guide RNA. The guide RNA provides target specificity to a Cas9-guide RNA complex by having a nucleotide sequence (a guide sequence) that is complementary to a sequence (the target site) of a target nucleic acid (as described elsewhere herein). The Cas9 protein of the complex provides the site-specific activity. In other words, the Cas9 protein is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA.

A Cas9 protein can bind and/or modify (e.g., cleave, nick, methylate, demethylate, etc.) a target nucleic acid and/or a polypeptide associated with target nucleic acid (e.g., methylation or acetylation of a histone tail)(e.g., when the Cas9 protein includes a fusion partner with an activity). In some cases, the Cas9 protein is a naturally-occurring protein (e.g., naturally occurs in bacterial and/or archaeal cells). In other cases, the Cas9 protein is not a naturally-occurring polypeptide (e.g., the Cas9 protein is a variant Cas9 protein, a chimeric protein, and the like).

Examples of suitable Cas9 proteins include, but are not limited to, those set forth in SEQ ID NOs: 5-816. Naturally occurring Cas9 proteins bind a Cas9 guide RNA, are thereby directed to a specific sequence within a target nucleic acid (a target site), and cleave the target nucleic acid (e.g., cleave dsDNA to generate a double strand break, cleave ssDNA, cleave ssRNA, etc.). A chimeric Cas9 protein is a fusion protein comprising a Cas9 polypeptide that is fused to a heterologous protein (referred to as a fusion partner), where the heterologous protein provides an activity (e.g., one that is not provided by the Cas9 protein). The fusion partner can provide an activity, e.g., enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc.). In some cases, a portion of the Cas9 protein (e.g., the RuvC domain and/or the HNH domain) exhibits reduced nuclease activity relative to the corresponding portion of a wild type Cas9 protein (e.g., in some cases the Cas9 protein is a nickase). In some cases, the Cas9 protein is enzymatically inactive, or has reduced enzymatic activity relative to a wild-type Cas9 protein (e.g., relative to *Streptococcs pyoes* Cas9).

Assays to determine whether given protein interacts with a Cas9 guide RNA can be any convenient binding assay that tests for binding between a protein and a nucleic acid. Suitable binding assays (e.g., gel shift assays) are known to those of ordinary skill in the art (e.g., assays that include adding a Cas9 guide RNA and a protein to a target nucleic acid).

Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) are known to those of ordinary skill in the art and can include adding a Cas9 guide RNA and a protein to a target nucleic acid.

Many Cas9 orthologs from a wide variety of species have been identified and in some cases the proteins share limited amino acid sequence identity. Identified Cas9 orthologs have similar domain architecture with a central HNH endonuclease domain and a split RuvC/RNaseH domain (e.g., RuvCI, RuvCII, and RuvCIII) (e.g., see Table 1). For example, a Cas9 protein can have 3 different regions (sometimes referred to as RuvC-I, RuvC-II, and RucC-III), that are not contiguous with respect to the primary amino acid sequence of the Cas9 protein, but fold together to form a RuvC domain once the protein is produced and folds. Thus, Cas9 proteins can be said to share at least 4 key motifs with a conserved architecture. Motifs 1, 2, and 4 are RuvC like motifs while motif 3 is an HNH-motif. The motifs set forth in Table 1 may not represent the entire RuvC-like and/or HNH domains as accepted in the art, but Table 1 does present motifs that can be used to help determine whether a given protein is a Cas9 protein.

TABLE 1

Table 1 lists 4 motifs that are present in Cas9 sequences from various species. The amino acids listed in Table 1 are from the Cas9 from *S. pyogenes* (SEQ ID NO: 5).

| Motif # | Motif | Amino acids (residue #s) | Highly conserved |
|---|---|---|---|
| 1 | RuvC-like I | IGLDIGTNSVGWAVI (7-21) (SEQ ID NO: 1) | D10, G12, G17 |
| 2 | RuvC-like II | IVIEMARE (759-766) (SEQ ID NO: 2) | E762 |
| 3 | HNH-motif | DVDHIVPQSFLKDDSIDNKVLTRSDKN (837-863) (SEQ ID NO: 3) | H840, N854, N863 |
| 4 | RuvC-like III | HHAHDAYL (982-989) (SEQ ID NO: 4) | H982, H983, A984, D986, A987 |

In some cases, a suitable Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 as set forth in SEQ ID NOs: 1-4, respectively (e.g., see Table 1), or to the corresponding portions in any of the amino acid sequences set forth in SEQ ID NOs: 5-816.

In other words, in some cases, a suitable Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816.

In some cases, a suitable Cas9 protein comprises an amino acid sequence having 4 motifs, each of motifs 1-4 having 60% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 70% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 75% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 80% or more amino acid sequence identity to motifs 1-4 of the Cas9 amino acid sequence set forth as SEQ ID NO: 5

(the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 85% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 90% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 95% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 99% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 100% amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. Any Cas9 protein as defined above can be used as a Cas9 polypeptide, as part of a chimeric Cas9 polypeptide (e.g., a Cas9 fusion protein).

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable Cas9 protein comprises an amino acid sequence having 60% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 70% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 75% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 80% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 85% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 90% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 95% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 99% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. Any Cas9 protein as defined above can be used as a Cas9 polypeptide, as part of a chimeric Cas9 polypeptide (e.g., a Cas9 fusion protein).

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to the Cas9 amino acid sequence set forth in SEQ ID NO: 5, or to any of the amino acid sequences set forth as SEQ ID NOs: 6-816.

In some cases, a suitable Cas9 protein comprises an amino acid sequence having 60% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 70% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 75% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 80% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 85% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 90% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 95% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 99% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 100% amino acid sequence identity to the Cas9 amino acid sequence set forth in SEQ ID NO: 5, or to any of the amino acid sequences set forth as SEQ ID NOs: 6-816. Any Cas9 protein as defined above can be used as a Cas9 polypeptide, as part of a chimeric Cas9 polypeptide (e.g., a Cas9 fusion protein).

In some cases, a Cas9 protein comprises 4 motifs (as listed in Table 1), at least one with (or each with) amino acid sequences having 75% or more, 80% or more, 85% or more, 90% or more, 95% or more, 99% or more or 100% amino acid sequence identity to each of the 4 motifs listed in Table 1 (SEQ ID NOs:1-4), or to the corresponding portions in any of the amino acid sequences set forth as SEQ ID NOs: 6-816.

Examples of various Cas9 proteins (and Cas9 domain structure) and Cas9 guide RNAs (as well as information regarding requirements related to protospacer adjacent motif (PAM) sequences present in targeted nucleic acids) can be found in the art, for example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al., Cell. 2013 Feb. 28; 152(5): 1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al., Nucleic Acids Res. 2013 November 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et al., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; Shmakov et al., Nat Rev Microbiol. 2017 March; 15(3):169-182; and U.S. patents and patent applications: U.S. Pat. Nos. 8,906,616; 8,895, 308; 8,889,418; 8,889,356; 8,871,445; 8,865,406; 8,795, 965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

Variant Cas9 Proteins—Nickases and dCas9

In some cases, a Cas9 protein is a variant Cas9 protein. A variant Cas9 protein has an amino acid sequence that is different by at least one amino acid (e.g., has a deletion, insertion, substitution, fusion) when compared to the amino acid sequence of a corresponding wild type Cas9 protein. In some instances, the variant Cas9 protein has an amino acid change (e.g., deletion, insertion, or substitution) that reduces the nuclease activity of the Cas9 protein. For example, in some instances, the variant Cas9 protein has 50% or less, 40% or less, 30% or less, 20% or less, 10% or less, 5% or less, or 1% or less of the nuclease activity of the corresponding wild-type Cas9 protein. In some cases, the variant Cas9 protein has no substantial nuclease activity. When a Cas9 protein is a variant Cas9 protein that has no substantial nuclease activity, it can be referred to as a nuclease defective Cas9 protein or "dCas9" for "dead" Cas9. A protein (e.g., a class 2 CRISPR/Cas protein, e.g., a Cas9 protein) that cleaves one strand but not the other of a double stranded target nucleic acid is referred to herein as a "nickase" (e.g., a "nickase Cas9").

In some cases, a variant Cas9 protein can cleave the complementary strand (sometimes referred to in the art as the target strand) of a target nucleic acid but has reduced ability to cleave the non-complementary strand (sometimes referred to in the art as the non-target strand) of a target nucleic acid. For example, the variant Cas9 protein can have a mutation (amino acid substitution) that reduces the function of the RuvC domain. Thus, the Cas9 protein can be a nickase that cleaves the complementary strand, but does not cleave the non-complementary strand. As a non-limiting example, in some embodiments, a variant Cas9 protein has a mutation at an amino acid position corresponding to residue D10 (e.g., D10A, aspartate to alanine) of SEQ ID NO: 5 (or the corresponding position of any of the proteins set forth in SEQ ID NOs: 6-261 and 264-816) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 protein cleaves a double stranded target nucleic acid) (see, for example, Jinek et al., Science. 2012 Aug. 17; 337(6096):816-21). See, e.g., SEQ ID NO: 262.

In some cases, a variant Cas9 protein can cleave the non-complementary strand of a target nucleic acid but has reduced ability to cleave the complementary strand of the target nucleic acid. For example, the variant Cas9 protein can have a mutation (amino acid substitution) that reduces the function of the HNH domain. Thus, the Cas9 protein can be a nickase that cleaves the non-complementary strand, but does not cleave the complementary strand. As a non-limiting example, in some embodiments, the variant Cas9 protein has a mutation at an amino acid position corresponding to residue H840 (e.g., an H840A mutation, histidine to alanine) of SEQ ID NO: 5 (or the corresponding position of any of the proteins set forth as SEQ ID NOs: 6-261 and 264-816) and can therefore cleave the non-complementary strand of the target nucleic acid but has reduced ability to cleave (e.g., does not cleave) the complementary strand of the target nucleic acid. Such a Cas9 protein has a reduced ability to cleave a target nucleic acid (e.g., a single stranded target nucleic acid) but retains the ability to bind a target nucleic acid (e.g., a single stranded target nucleic acid). See, e.g., SEQ ID NO: 263.

In some cases, a variant Cas9 protein has a reduced ability to cleave both the complementary and the non-complementary strands of a double stranded target nucleic acid. As a non-limiting example, in some cases, the variant Cas9 protein harbors mutations at amino acid positions corresponding to residues D10 and H840 (e.g., D10A and H840A) of SEQ ID NO: 5 (or the corresponding residues of any of the proteins set forth as SEQ ID NOs: 6-261 and 264-816) such that the polypeptide has a reduced ability to cleave (e.g., does not cleave) both the complementary and the non-complementary strands of a target nucleic acid. Such a Cas9 protein has a reduced ability to cleave a target nucleic acid (e.g., a single stranded or double stranded target nucleic acid) but retains the ability to bind a target nucleic acid. A Cas9 protein that cannot cleave target nucleic acid (e.g., due to one or more mutations, e.g., in the catalytic domains of the RuvC and HNH domains) is referred to as a "dead" Cas9 or simply "dCas9." See, e.g., SEQ ID NO: 264.

Other residues can be mutated to achieve the above effects (i.e. inactivate one or the other nuclease portions). As non-limiting examples, residues D10, G12, G17, E762, H840, N854, N863, H982, H983, A984, D986, and/or A987 of SEQ ID NO: 5 (or the corresponding mutations of any of the proteins set forth as SEQ ID NOs: 6-816) can be altered (i.e., substituted). Also, mutations other than alanine substitutions are suitable.

In some embodiments, a variant Cas9 protein that has reduced catalytic activity (e.g., when a Cas9 protein has a D10, G12, G17, E762, H840, N854, N863, H982, H983, A984, D986, and/or a A987 mutation of SEQ ID NO: 5 or the corresponding mutations of any of the proteins set forth as SEQ ID NOs: 6-816, e.g., D10A, Gl2A, Gl7A, E762A, H840A, N854A, N863A, H982A, H983A, A984A, and/or D986A), the variant Cas9 protein can still bind to target nucleic acid in a site-specific manner (because it is still guided to a target nucleic acid sequence by a Cas9 guide RNA) as long as it retains the ability to interact with the Cas9 guide RNA.

In addition to the above, a variant Cas9 protein can have the same parameters for sequence identity as described above for Cas9 proteins. Thus, in some cases, a suitable variant Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 4 motifs, each of motifs 1-4 having 60% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 70% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 75% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 80% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 85% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 90% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 95% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 99% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 100% amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable variant Cas9 protein comprises an amino acid sequence having 60% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 70% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 75% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 80% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 85% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 90% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 95% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 99% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 60% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 70% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 75% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 80% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 85% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 90% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 95% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 99% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 100% amino acid sequence identity to the Cas9 amino acid sequence set forth in SEQ ID NO: 5, or to any of the amino acid sequences set forth as SEQ ID NOs: 6-816.

In some cases, a Cas9 polypeptide comprises an amino acid sequence having at least 50%, at least 60%, at least 70%, at least 80%, at least 90%, at least 95%, at least 98%, at least 99%, or more than 99%, amino acid sequence identity to the *Streptococcs pyoes* Cas9 depicted in FIG. 6A. In some cases, a Cas9 polypeptide comprises the amino acid sequence depicted in one of FIG. 6A-6F.

In some cases, the Cas9 polypeptide used in a composition or method of the present disclosure is a *Staphylococcu aureus* Cas9 (saCas9) polypeptide. In some cases, the saCas9 polypeptide comprises an amino acid sequence having at least 85%, at least 90%, at least 95%, at least 98%, at least 99%, or 100%, amino acid sequence identity to the saCas9 amino acid sequence depicted in FIG. 7.

In some cases, the Cas9 polypeptide used in a composition or method of the present disclosure is a *Campylobacter jejuni* Cas9 (CjCas9) polypeptide. CjCas9 recognizes the 5'-NNNVRYM-3' as the protospacer-adjacent motif (PAM). The amino acid sequence of CjCas9 is set forth in SEQ ID NO:50. In some cases, a Cas9 polypeptide suitable for use in a composition or method of the present disclosure comprises an amino acid sequence having at least 50%, at least 60%, at least 70%, at least 80%, at least 90%, at least 95%, at least 98%, at least 99%, or more than 99%, amino acid sequence identity to the CjCas9 amino acid sequence set forth in SEQ ID NO:50.

In some cases, a suitable Cas9 polypeptide is a high-fidelity (HF) Cas9 polypeptide. Kleinstiver et al. (2016) *Nature* 529:490. For example, amino acids N497, R661, Q695, and Q926 of the amino acid sequence depicted in FIG. 6A are substituted, e.g., with alanine. For example, an HF Cas9 polypeptide can comprise an amino acid sequence having at least 90%, at least 95%, at least 98%, at least 99%, or 100%, amino acid sequence identity to the amino acid sequence depicted in FIG. 6A, where amino acids N497, R661, Q695, and Q926 are substituted, e.g., with alanine.

In some cases, a suitable Cas9 polypeptide exhibits altered PAM specificity. See, e.g., Kleinstiver et al. (2015) *Nature* 523:481.

In some cases, the genome-editing endonuclease is a type V CRISPR/Cas endonuclease. In some cases a type V CRISPR/Cas endonuclease is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence depicted in FIG. 8A, FIG. 8B, or FIG. 8C.

In some cases, a genome targeting composition of the present disclosure includes a type V or type VI CRISPR/Cas endonuclease (i.e., the genome editing endonuclease is a type V or type VI CRISPR/Cas endonuclease) (e.g., Cpf1, C2c1, C2c2, C2c3). Type V and type VI CRISPR/Cas endonucleases are a type of class 2 CRISPR/Cas endonuclease. Examples of type V CRISPR/Cas endonucleases include but are not limited to: Cpf1, C2c1, and C2c3. An example of a type VI CRISPR/Cas endonuclease is C2c2. In some cases, a subject genome targeting composition includes a type V CRISPR/Cas endonuclease (e.g., Cpf1, C2c1, C2c3). In some cases, a Type V CRISPR/Cas endonuclease is a Cpf1 protein. In some cases, a subject genome targeting composition includes a type VI CRISPR/Cas endonuclease (e.g., Cas13a).

Like type II CRISPR/Cas endonucleases, type V and VI CRISPR/Cas endonucleases form a complex with a corresponding guide RNA. The guide RNA provides target specificity to an endonuclease-guide RNA RNP complex by having a nucleotide sequence (a guide sequence) that is complementary to a sequence (the target site) of a target nucleic acid (as described elsewhere herein). The endonuclease of the complex provides the site-specific activity. In other words, the endonuclease is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the protein-binding segment of the guide RNA.

Examples and guidance related to type V and type VI CRISPR/Cas proteins (e.g., Cpf1, C2c1, C2c2, and C2c3 guide RNAs) can be found in the art, for example, see Zetsche et al., Cell. 2015 Oct. 22; 163(3):759-71; Makarova et al., Nat Rev Microbiol. 2015 November; 13(11):722-36; Shmakov et al., Mol Cell. 2015 Nov. 5; 60(3):385-97; and Shmakov et al. (2017) Nature Reviews Microbiology 15:169.

In some cases, the Type V or type VI CRISPR/Cas endonuclease (e.g., Cpf1, C2c1, C2c2, C2c3) is enzymatically active, e.g., the Type V or type VI CRISPR/Cas polypeptide, when bound to a guide RNA, cleaves a target nucleic acid. In some cases, the Type V or type VI CRISPR/Cas endonuclease (e.g., Cpf1, C2c1, C2c2, C2c3) exhibits reduced enzymatic activity relative to a corresponding wild-type a Type V or type VI CRISPR/Cas endonuclease (e.g., Cpf1, C2c1, C2c2, C2c3), and retains DNA binding activity.

In some cases, a type V CRISPR/Cas endonuclease is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the Cpf1 amino acid sequence set forth in any of SEQ ID NOs:818-822.

In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the Cpf1 amino acid sequence set forth in any of SEQ ID NOs: 818-822. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the Cpf1 amino acid sequence set forth in any of SEQ ID NOs: 818-822. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the Cpf1 amino acid sequence set forth in any of SEQ ID NOs: 818-822. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the Cpf1 amino acid sequence set forth in any of SEQ ID NOs: 818-822.

In some cases, the Cpf1 protein exhibits reduced enzymatic activity relative to a wild-type Cpf1 protein (e.g., relative to a Cpf1 protein comprising the amino acid sequence set forth in any of SEQ ID NOs: 818-822), and retains DNA binding activity. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822; and comprises an amino acid substitution (e.g., a D→substitution) at an amino acid residue corresponding to amino acid 917 of the Cpf1 amino acid sequence set forth in SEQ ID NO: 818. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822; and comprises an amino acid substitution (e.g., an E→A substitution) at an amino acid residue corresponding to amino acid 1006 of the Cpf1 amino acid sequence set forth in SEQ ID NO: 818. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822; and comprises an amino acid substitution (e.g., a D→A substitution) at an amino acid residue corresponding to amino acid 1255 of the Cpf1 amino acid sequence set forth in SEQ ID NO: 818.

In some cases, a suitable Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822.

In some cases, a type V CRISPR/Cas endonuclease is a C2c1 protein (examples include those set forth as SEQ ID NOs: 823-830). In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c1 amino acid sequence set forth in any of SEQ ID NOs: 823-830. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c1 amino acid sequence set forth in any of SEQ ID NOs: 823-830.

In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c1 amino acid sequences set forth in any of SEQ ID NOs: 823-830). In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c1 amino acid sequence set forth in any of SEQ ID NOs: 823-830. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c1 amino acid sequence set forth in any of SEQ ID NOs: 823-830. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c1 amino acid sequence set forth in any of SEQ ID NOs: 823-830.

In some cases, the C2c1 protein exhibits reduced enzymatic activity relative to a wild-type C2c1 protein (e.g., relative to a C2c1 protein comprising the amino acid sequence set forth in any of SEQ ID NOs: 823-830), and retains DNA binding activity. In some cases, a suitable C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c1 amino acid sequence set forth in any of SEQ ID NOs: 823-830.

In some cases, a type V CRISPR/Cas endonuclease is a C2c3 protein (examples include those set forth as SEQ ID NOs: 831-834). In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c3 amino acid sequence set forth in any of SEQ ID NOs: 831-834. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c3 amino acid sequence set forth in any of SEQ ID NOs: 831-834.

In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c3 amino acid sequence set forth in any of SEQ ID NOs: 831-834. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c3 amino acid sequence set forth in any of SEQ ID NOs: 831-834. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c3 amino acid sequence set forth in any of SEQ ID NOs: 831-834. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c3 amino acid sequence set forth in any of SEQ ID NOs: 831-834.

In some cases, the C2c3 protein exhibits reduced enzymatic activity relative to a wild-type C2c3 protein (e.g., relative to a C2c3 protein comprising the amino acid sequence set forth in any of SEQ ID NOs: 831-834), and retains DNA binding activity. In some cases, a suitable C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c3 amino acid sequence set forth in any of SEQ ID NOs: 831-834.

In some cases a type VI CRISPR/Cas endonuclease is a C2c2 protein (examples include those set forth as SEQ ID NOs: 835-846). In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c2 amino acid sequence set forth in any of SEQ ID NOs: 835-846. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c2 amino acid sequence set forth in any of SEQ ID NOs: 835-846.

In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c2 amino acid sequence set forth in any of SEQ ID NOs: 835-846. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c2 amino acid sequence set forth in any of SEQ ID NOs: 835-846. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c2 amino acid sequence set forth in any of SEQ ID NOs: 835-846. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c2 amino acid sequence set forth in any of SEQ ID NOs: 835-846.

In some cases, the C2c2 protein exhibits reduced enzymatic activity relative to a wild-type C2c2 protein (e.g., relative to a C2c2 protein comprising the amino acid sequence set forth in any of SEQ ID NOs: 835-846), and retains DNA binding activity. In some cases, a suitable C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c2 amino acid sequence set forth in any of SEQ ID NOs: 835-846.

Examples and guidance related to type V or type VI CRISPR/Cas endonucleases (including domain structure) and guide RNAs (as well as information regarding requirements related to protospacer adjacent motif (PAM) sequences present in targeted nucleic acids) can be found in the art, for example, see Zetsche et al., Cell. 2015 Oct. 22; 163(3):759-71; Makarova et al., *Nat Rev Microbiol.* 2015 November; 13(11):722-36; Shmakov et al., *Mol Cell.* 2015 Nov. 5; 60(3):385-97; and Shmakov et al., Nat Rev Microbiol. 2017 March; 15(3):169-182; and U.S. patents and patent applications: 9,580,701; 20170073695, 20170058272, 20160362668, 20160362667, 20160298078, 20160289637, 20160215300, 20160208243, and 20160208241, each of which is hereby incorporated by reference in its entirety.

In some cases, a genome editing nuclease is a fusion protein that is fused to a heterologous polypeptide (also referred to as a "fusion partner"). In some cases, a genome editing nuclease is fused to an amino acid sequence (a fusion partner) that provides for subcellular localization, i.e., the fusion partner is a subcellular localization sequence (e.g., one or more nuclear localization signals (NLSs) for targeting to the nucleus, two or more NLSs, three or more NLSs, etc.).

In some cases, a gene-editing enzyme suitable for inclusion in a composition of the present disclosure is biotinylated, i.e., includes one or more biotin moieties.

Signaling Molecules

In some cases, the polypeptide is a signaling molecule. Signaling molecules include, for example, any agent that interacts with a cell, e.g., through cell surface receptors, to produce an effect on the surface of or within the cell. In some instances, a signaling molecule is a biomolecule secreted by a cell into an extracellular space. A signaling molecule may be, for example, a ligand or a receptor. Signaling molecules of interest include, for example, hormones, growth factors, cytokines, immunomodulators, neuropeptides, and the like.

In some cases, the polypeptide is a polypeptide hormone. Any suitable peptide hormone or amino acid-based hormone may be used in the subject methods and compositions. Hormones or macromolecules having metabolic actions resembling those of hormones for use in the subject methods and compositions may include, for example, prolactin, adrenocorticotropic hormone, growth hormone, antidiuretic hormone, atrial-natriuretic peptide, glucagon, insulin, somatostatin, cholecystokinin, gastrin, leptin, angiotensin II, fibroblast growth factors, parathyroid hormone-related protein, melanocortins, orexin, OXTR, epinephrine, norepinephrine, thyroxine, melatonin, oxytocin, and isoforms thereof. In some instances, the macromolecule includes a precursor of a hormone peptide or polypeptide. In some cases, the macromolecule is a hormone receptor.

In some instances, the polypeptide is a growth factor. Growth factors for use in the subject methods and compositions include, but are not limited to, bone morphogenetic proteins, angiopoietin, autocrine motility factor, ciliary neurotrophic factor family (e.g., CNTF, LIF, IL-6), colony-stimulating factors, epidermal growth factor, ephrins, erythropoietin, foetal bovine somatotrophin, GDNF family of ligands, growth differentiation factor-9, hepatocyte growth factor, hepatoma-derived growth factor, insulin-like growth factors, interleukins, migration-stimulating factor, neuregulins, neurotrophins, placental growth factor, platelet-derived growth factor, renalase, T-cell growth factor, transforming growth factors, tumor necrosis factor-alpha, thrombopoietin, VEGF, EGF, NGF, PDGF, somatotropin, and the like. In some cases, the polypeptide is an immunomodulator. An immunomodulator is an agent that alters, suppresses, or stimulates the body's immune system. Suitable immunomodulators include, e.g., a cytokine, chemokine, a stem cell growth factor, a lymphotoxin, a hematopoietic factor, a colony stimulating factor (CSF), an interferon (IFN), erythropoietin, thrombopoietin, and the like. Suitable lymphotoxins include, e.g., tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferon-α, interferon-β, interferon-γ, or interferon-A.

In some cases, the polypeptide is a neuropeptide. Neuropeptides for use in the subject methods and compositions may include, but are not limited to, substance P, opioid peptides, endorphins, enkephalins, dynorphins, neurokinin A, neuropeptide K, neuropeptide γ, galanin, somatostatin, cholecystokinin, VIP, neurotensin, glucagon-like peptide-1, TRH, etc.

Factors Modulating Gene Expression

In some cases, the polypeptide is a transcriptional modulator. A transcriptional modulator may be any agent that regulates the transcription of a gene such as a transcription factor. As used herein, the term "transcription factor" refers to any polypeptide that may act by itself or in combination with at least one other polypeptide to regulate gene expression levels by modulating transcription. The term is not limited to polypeptides that directly bind DNA sequences. The transcription factor will in some cases increase expression levels. However, in some cases it may be desirable to suppress expression of a particular pathway. The transcription factor may be a transcription factor identified by sequence analysis or a naturally-occurring reading frame sequence that has not been previously characterized as a transcription factor. The polypeptide may also be an artificially generated or chemically or enzymatically modified polypeptide. Chemical or enzymatic alteration of expressed nucleic acids and polypeptides can be performed by standard methods. For example, sequence can be modified by addition of phosphate groups, methyl groups, lipids, sugars, peptides, organic or inorganic compounds, by the inclusion of modified nucleotides or amino acids, or the like. Further the transcription factor may be derived from a collection of transcripts, such as a cDNA library, and the sequence of the transcript may be unknown.

In some cases, the polypeptide is a translational modulator. A translational modulator may be any agent that regulates the translation of a gene such as a translation factor. As used herein, the term "translation factor" refers to any polypeptide that may act by itself or in combination with at least one other polypeptide to regulate gene expression levels by modulating translation. The translation factor may increase or suppress expression of a particular pathway. The translation factor may be a translation factor identified by sequence analysis or a naturally-occurring reading frame sequence that has not been previously characterized as a translation factor. The polypeptide may also be an artificially generated or chemically or enzymatically modified polypeptide. Chemical or enzymatic alteration of expressed nucleic acids and polypeptides can be performed by standard methods. For example, sequence can be modified by addition of phosphate groups, methyl groups, lipids, sugars, peptides, organic or inorganic compounds, by the inclusion of modified nucleotides or amino acids, or the like.

In some cases, the polypeptide is a post-translational modulator. In some instances, the post-translation modulator is an enzyme capable of performing post-translation modifications. As used herein, post-translational modifications refer to enzymatic modifications of polypeptides during or after protein synthesis. Post-translational modifications include, for example, phosphorylation, glycosylation, lipidation, carbonylation, bond cleavage, bond formation (i.e. disulfide bond formation), protein folding, protein splicing, etc. Post-translational modulators of interest include, for example, kinases, phosphatases, chaperones, etc.

In some cases, the polypeptide has enzymatic activity that modifies a polypeptide (e.g., a histone) associated with a nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Antibodies

In some cases, the polypeptide is an antibody. The terms "antibodies" and "immunoglobulin" include antibodies or immunoglobulins of any isotype, fragments of antibodies that retain specific binding to antigen (e.g., to a target ligand-binding polypeptide), including, but not limited to, Fab, Fv, scFv, and Fd fragments, chimeric antibodies, humanized antibodies, single-chain antibodies (scAb), single domain antibodies (sdAb), single domain heavy chain antibodies, a single domain light chain antibodies, nanobodies, bi-specific antibodies, multi-specific antibodies, and fusion proteins comprising an antigen-binding (also referred to herein as antigen binding) portion of an antibody and a non-antibody protein. Also encompassed by the term are Fab', Fv, F(ab')$_2$, and or other antibody fragments that retain specific binding to antigen, and monoclonal antibodies.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al. (1995) *Protein Eng.* 8(10): 1057-1062); domain antibodies (dAb; Holt et al. (2003) *Trends Biotechnol.* 21:484); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen. Antibody fragments include, e.g., scFv, sdAb, dAb, Fab, Fab', Fab'$_2$, F(ab')$_2$, Fd, Fv, Feb, and SMIP. Examples of sdAb are a camelid VHH and a cartilaginous fish VNAR.

"Fv" is the minimum antibody fragment that contains a complete antigen-recognition and-binding site. This region consists of a dimer of one heavy- and one light-chain variable domain in tight, non-covalent association. It is in this configuration that the three complementarity determining regions (CDRs) of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies, vol. 113, Rosenburg and Moore eds., Springer-Verlag, New York*, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

Chemotherapeutic Agents

In some cases, the polypeptide is a chemotherapeutic agent. A chemotherapeutic agent may be a naturally occurring or synthetic polypeptide to kill cancer cells at a primary tumor site or at distant sites to where cancer has metastasized. A chemotherapeutic agent for use in the subject methods and compositions may be any chemotherapeutic polypeptide or peptide known in the art. Suitable chemotherapeutic agents include, but are not limited to, antibodies (e.g., anti-vascular endothelial growth factor (VEGF) antibody, HER2 antibody), antimicrobial peptides, LHRH agonists (e.g., buserelin, gonadorelin, goserelin, histrelin, leuprolide, nafarelin, triptorelin), antagonists (abarelix, cetrorelix, degarelix, ganirelix, etc.), and any other suitable agents known in the art.

Nucleic Acids

In some cases, a composition of the present disclosure comprises: a) an endosomal disruptor of the present disclosure; and b) one or more nucleic acids. Suitable polynucleotides include, e.g., naturally or non-naturally occurring DNA (including cDNA, genomic DNA, nuclear DNA, mitochondrial DNA), RNA (including mRNA, rRNA, tRNA), oligonucleotides, a triple-helix forming molecule, small interfering RNA (siRNA) or microRNAs (miRNA) used to modulate gene expression, antisense oligonucleotides used to modulate gene expression, aptamers, ribozymes, a gene or gene fragment, a regulatory sequence, including analogs, derivatives, and combinations thereof. Suitable RNA molecules include, e.g., a guide RNA, mRNA, siRNA, RNAi, shRNA, miRNA, RNA ribozyme, and an RNA aptamer. In some cases, the polynucleotide included in a composition of the present disclosure is a recombinant expression vector, e.g., a recombinant vector comprising a heterologous nucleotide sequence encoding a gene product (a polypeptide or a polynucleotide) of interest.

In some cases, a composition of the present disclosure comprises: a) an endosomal disruptor of the present disclosure; b) an mRNA comprising a nucleotide sequence encoding a genome-editing enzyme; and c) a guide RNA. In some cases, a composition of the present disclosure comprises: a) an endosomal disruptor of the present disclosure; b) a recombinant expression vector comprising a nucleotide sequence encoding genome-editing enzyme; and c) a guide RNA. In some cases, a composition of the present disclosure comprises: a) an endosomal disruptor of the present disclosure; b) an mRNA comprising a nucleotide sequence encoding genome-editing enzyme; c) a guide RNA; and d) a donor DNA template. In some cases, a composition of the present disclosure comprises: a) an endosomal disruptor of the present disclosure; b) a recombinant expression vector comprising a nucleotide sequence encoding genome-editing enzyme; c) a guide RNA; and d) a donor DNA template.

Guide RNAs

In some cases, a suitable nucleic acid is a guide RNA. A nucleic acid that binds to a class 2 CRISPR/Cas endonuclease (e.g., a Cas9 protein; a type V or type VI CRISPR/Cas protein; a Cpf1 protein; etc.) and targets the complex to a specific location within a target nucleic acid is referred to herein as a "guide RNA" or "CRISPR/Cas guide nucleic acid" or "CRISPR/Cas guide RNA." A guide RNA provides target specificity to the complex (the RNP complex) by including a targeting segment, which includes a guide sequence (also referred to herein as a targeting sequence), which is a nucleotide sequence that is complementary to a sequence of a target nucleic acid. It is to be understood that in some cases, a hybrid DNA/RNA can be made such that a CRISPR/Cas guide RNA includes DNA bases in addition to RNA bases, but the term "CRISPR/Cas guide RNA" is still used to encompass such a molecule herein.

A CRISPR/Cas guide RNA can be said to include two segments, a targeting segment and a protein-binding segment. The targeting segment of a CRISPR/Cas guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a Class 2 CRISPR/Cas effector protein. The protein-binding segment of a subject CRISPR/Cas guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the CRISPR/Cas guide RNA (the guide sequence of the CRISPR/Cas guide RNA) and the target nucleic acid.

In some cases, a guide RNA includes two separate nucleic acid molecules: an "activator" and a "targeter" and is referred to herein as a "dual guide RNA", a "double-molecule guide RNA", a "two-molecule guide RNA", or a "dgRNA." In some cases, the guide RNA is one molecule (e.g., for some class 2 CRISPR/Cas proteins, the corresponding guide RNA is a single molecule; and in some cases, an activator and targeter are covalently linked to one another, e.g., via intervening nucleotides), and the guide RNA is referred to as a "single guide RNA", a "single-molecule guide RNA," a "one-molecule guide RNA", or simply "sgRNA."

In some cases, a composition of the present disclosure comprises: a) an endosomal disruptor; and b) an RNA-guided endonuclease. In some cases, a composition of the present disclosure comprises: a) an endosomal disruptor; b) an RNA-guided endonuclease; and c) an RNA-guided endonuclease. In some cases, e.g., where a target nucleic acid comprises a deleterious mutation in a defective allele (e.g., a deleterious mutation in a retinal cell target nucleic acid), the RNA-guided endonuclease/guide RNA complex, together with a donor nucleic acid comprising a nucleotide sequence that corrects the deleterious mutation (e.g., a donor nucleic acid comprising a nucleotide sequence that encodes a functional copy of the protein encoded by the defective allele), can be used to correct the deleterious mutation, e.g., via homology-directed repair (HDR).

In some cases, a composition of the present disclosure comprises, in addition to an endosomal disruptor: i) an RNA-guided endonuclease; and ii) one guide RNA. In some cases, the guide RNA is a single-molecule (or "single guide") guide RNA (an "sgRNA"). In some cases, the guide RNA is a dual-molecule (or "dual-guide") guide RNA ("dgRNA").

In some cases, a composition of the present disclosure comprises, in addition to an endosomal disruptor: i) a Cpf1 polypeptide; and ii) a guide RNA precursor; in these cases, the precursor can be cleaved by the Cpf1 polypeptide to generate 2 or more guide RNAs.

A CRISPR/Cas guide RNA and a Class 2 CRISPR/Cas effector protein, e.g., a fusion Class 2 CRISPR/Cas effector protein, form a complex (e.g., bind via non-covalent interactions). The CRISPR/Cas guide RNA provides target specificity to the complex by including a targeting segment, which includes a guide sequence (a nucleotide sequence that is complementary to a sequence of a target nucleic acid). The Class 2 CRISPR/Cas effector protein of the complex provides the site-specific activity (e.g., cleavage activity provided by the Class 2 CRISPR/Cas effector protein and/or an activity provided by the fusion partner in the case of a chimeric Class 2 CRISPR/Cas effector protein). In other words, the Class 2 CRISPR/Cas effector protein is guided to a target nucleic acid sequence (e.g. a target sequence) by virtue of its association with the CRISPR/Cas guide RNA.

The "guide sequence" also referred to as the "targeting sequence" of a CRISPR/Cas guide RNA can be modified so that the CRISPR/Cas guide RNA can target a Class 2 CRISPR/Cas effector protein (e.g., a naturally occurring Class 2 CRISPR/Cas effector protein, a fusion Class 2 CRISPR/Cas effector protein (chimeric effector), and the like) to any desired sequence of any desired target nucleic acid, with the exception (e.g., as described herein) that the PAM sequence can be taken into account. Thus, for example, a CRISPR/Cas guide RNA can have a guide sequence with complementarity to (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

A suitable CRISPR/Cas guide RNA includes a guide sequence (i.e., a targeting sequence), which is a nucleotide sequence that is complementary to a sequence (a target site) in a target nucleic acid. In other words, the guide sequence of a CRISPR/Cas guide RNA can interact with a target nucleic acid (e.g., double stranded DNA (dsDNA), single stranded DNA (ssDNA), single stranded RNA (ssRNA), or double stranded RNA (dsRNA)) in a sequence-specific manner via hybridization (i.e., base pairing). The guide sequence of a CRISPR/Cas guide RNA can be modified (e.g., by genetic engineering)/designed to hybridize to any desired target sequence (e.g., while taking the PAM into account, e.g., when targeting a dsDNA target) within a target nucleic acid (e.g., a eukaryotic target nucleic acid such as genomic DNA).

In some embodiments, the percent complementarity between the guide sequence and the target site of the target nucleic acid is 60% or more (e.g., 65% or more, 70% or more, 75% or more, 80% or more, 85% or more, 90% or more, 95% or more, 97% or more, 98% or more, 99% or more, or 100%). In some cases, the percent complementarity between the guide sequence and the target site of the target nucleic acid is 80% or more (e.g., 85% or more, 90% or more, 95% or more, 97% or more, 98% or more, 99% or more, or 100%). In some cases, the percent complementarity between the guide sequence and the target site of the target nucleic acid is 90% or more (e.g., 95% or more, 97% or more, 98% or more, 99% or more, or 100%). In some cases, the percent complementarity between the guide sequence and the target site of the target nucleic acid is 100%.

In some cases, the percent complementarity between the guide sequence and the target site of the target nucleic acid is 100% over the seven contiguous 3'-most nucleotides of the target site of the target nucleic acid.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 100% over 17 or more (e.g., 18 or more, 19 or more, 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 100% over 19 or more (e.g., 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 90% or more (e.g., 95% or more, 97% or more, 98% or more, 99% or more, or 100%) over 17-25 contiguous nucleotides. In some cases, the percent complementarity between the guide sequence and the target site of the target nucleic acid is 100% over 17-25 contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 90% or more (e.g., 95% or more, 97% or more, 98% or more, 99% or more, or 100%) over 19-25 contiguous nucleotides. In some cases, the percent complementarity between the guide sequence and the target site of the target nucleic acid is 100% over 19-25 contiguous nucleotides.

In some cases, the guide sequence has a length in a range of from 17-30 nucleotides (nt) (e.g., from 17-25, 17-22, 17-20, 19-30, 19-25, 19-22, 19-20, 20-30, 20-25, or 20-22 nt). In some cases, the guide sequence has a length in a range of from 17-25 nucleotides (nt) (e.g., from 17-22, 17-20, 19-25, 19-22, 19-20, 20-25, or 20-22 nt). In some cases, the guide sequence has a length of 17 or more nt (e.g., 18 or more, 19 or more, 20 or more, 21 or more, or 22 or more nt; 19 nt, 20 nt, 21 nt, 22 nt, 23 nt, 24 nt, 25 nt, etc.). In some cases, the guide sequence has a length of 19 or more nt (e.g., 20 or more, 21 or more, or 22 or more nt; 19 nt, 20 nt, 21 nt, 22 nt, 23 nt, 24 nt, 25 nt, etc.). In some cases, the guide sequence has a length of 17 nt. In some cases, the guide sequence has a length of 18 nt. In some cases, the guide sequence has a length of 19 nt. In some cases, the guide sequence has a length of 20 nt. In some cases, the guide sequence has a length of 21 nt. In some cases, the guide sequence has a length of 22 nt. In some cases, the guide sequence has a length of 23 nt.

In some cases, a CRISPR/Cas guide RNA has a length of 30 nucleotides (nt) or more (e.g., 35 nt or more, 40 nt or more, 45 nt or more, 50 nt or more, 55 nt or more, or 60 nt or more). In some cases, a CRISPR/Cas guide RNA has a length of 40 nucleotides (nt) or more (e.g., 45 nt or more, 50 nt or more, 55 nt or more, or 60 nt or more). In cases, a CRISPR/Cas guide RNA has a length of from 30 nucleotides (nt) to 100 nt (e.g., 30-90, 30-80, 30-75, 30-70, 30-65, 40-100, 40-90, 40-80, 40-75, 40-70, or 40-65 nt). In some cases, a CRISPR/Cas guide RNA has a length of from 40 nucleotides (nt) to 100 nt (e.g., 40-90, 40-80, 40-75, 40-70, or 40-65 nt).

The protein-binding segment of a CRISPR/Cas guide RNA interacts with a Class 2 CRISPR/Cas effector protein. The CRISPR/Cas guide RNA guides the bound Class 2 CRISPR/Cas effector protein to a specific nucleotide sequence within target nucleic acid via the above-mentioned guide sequence. The protein-binding segment of a CRISPR/Cas guide RNA comprises two stretches of nucleotides that are complementary to one another and hybridize to form a double stranded RNA duplex (dsRNA duplex). Thus, the protein-binding segment includes a dsRNA duplex.

In some cases, the dsRNA duplex region includes a range of from 5-25 base pairs (bp) (e.g., from 5-22, 5-20, 5-18, 5-15, 5-12, 5-10, 5-8, 8-25, 8-22, 8-18, 8-15, 8-12, 12-25, 12-22, 12-18, 12-15, 13-25, 13-22, 13-18, 13-15, 14-25, 14-22, 14-18, 14-15, 15-25, 15-22, 15-18, 17-25, 17-22, or 17-18 bp, e.g., 5 bp, 6 bp, 7 bp, 8 bp, 9 bp, 10 bp, etc.). In some cases, the dsRNA duplex region includes a range of from 6-15 base pairs (bp) (e.g., from 6-12, 6-10, or 6-8 bp, e.g., 6 bp, 7 bp, 8 bp, 9 bp, 10 bp, etc.). In some cases, the duplex region includes 5 or more bp (e.g., 6 or more, 7 or more, or 8 or more bp). In some cases, the duplex region includes 6 or more bp (e.g., 7 or more, or 8 or more bp). In some cases, not all nucleotides of the duplex region are paired, and therefore the duplex forming region can include a bulge. The term "bulge" herein is used to mean a stretch of nucleotides (which can be one nucleotide or multiple nucleotides) that do not contribute to a double stranded duplex, but which are surround 5' and 3' by nucleotides that do contribute, and as such a bulge is considered part of the duplex region. In some cases, the dsRNA includes 1 or more bulges (e.g., 2 or more, 3 or more, 4 or more bulges). In some cases, the dsRNA duplex includes 2 or more bulges (e.g., 3 or more, 4 or more bulges). In some cases, the dsRNA duplex includes 1-5 bulges (e.g., 1-4, 1-3, 2-5, 2-4, or 2-3 bulges).

Thus, in some cases, the stretches of nucleotides that hybridize to one another to form the dsRNA duplex have 70%-100% complementarity (e.g., 75%-100%, 80%-10%, 85%-100%, 90%-100%, 95%-100% complementarity) with one another. In some cases, the stretches of nucleotides that hybridize to one another to form the dsRNA duplex have 70%-100% complementarity (e.g., 75%-100%, 80%-10%, 85%-100%, 90%-100%, 95%-100% complementarity) with one another. In some cases, the stretches of nucleotides that hybridize to one another to form the dsRNA duplex have 85%-100% complementarity (e.g., 90%-100%, 95%-100% complementarity) with one another. In some cases, the stretches of nucleotides that hybridize to one another to form the dsRNA duplex have 70%-95% complementarity (e.g., 75%-95%, 80%-95%, 85%-95%, 90%-95% complementarity) with one another.

In other words, in some cases, the dsRNA duplex includes two stretches of nucleotides that have 70%-100% complementarity (e.g., 75%-100%, 80%-10%, 85%-100%, 90%-100%, 95%-100% complementarity) with one another. In some cases, the dsRNA duplex includes two stretches of nucleotides that have 85%-100% complementarity (e.g., 90%-100%, 95%-100% complementarity) with one another. In some cases, the dsRNA duplex includes two stretches of nucleotides that have 70%-95% complementarity (e.g., 75%-95%, 80%-95%, 85%-95%, 90%-95% complementarity) with one another.

The duplex region of a CRISPR/Cas guide RNA can include one or more (1, 2, 3, 4, 5, etc.) mutations relative to a naturally occurring duplex region. For example, in some cases a base pair can be maintained while the nucleotides contributing to the base pair from each segment can be different. In some cases, the duplex region of a subject CRISPR/Cas guide RNA includes more paired bases, less paired bases, a smaller bulge, a larger bulge, fewer bulges, more bulges, or any convenient combination thereof, as compared to a naturally occurring duplex region (of a naturally occurring CRISPR/Cas guide RNA).

Examples of various Cas9 guide RNAs can be found in the art, and in some cases variations similar to those introduced into these guide RNAs can also be introduced into CRISPR/Cas guide RNAs of the present disclosure (e.g., mutations to the dsRNA duplex region, extension of the 5' or 3' end for added stability for to provide for interaction with another protein, and the like). For example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et. al, Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

A CRISPR/Cas guide RNA comprises both the guide sequence and two stretches ("duplex-forming segments") of nucleotides that hybridize to form the dsRNA duplex of the protein-binding segment. The particular sequence of a given CRISPR/Cas guide RNA can be characteristic of the species in which the crRNA is found. Suitable protein binding regions (repeat sequences) of CRISPR/Cas guide RNAs include, but are not limited to, those provided herein.

Donor DNA

In some cases, a composition of the present disclosure comprises, in addition to an endosomal disruptor, a donor DNA. In some cases, a composition of the present disclosure comprises: a) an endosomal disruptor; b) an RNA-guided endonuclease; c) a guide RNA; and d) a donor DNA. The term "donor DNA" is used herein to refer to a DNA comprising a nucleotide sequence ("donor sequence") to be inserted (via homologous recombination) into a target site of a target DNA (e.g., the genomic DNA of a target cell). In some cases, the donor sequence is inserted at or near a cleavage site induced by a site-specific genome editing protein (e.g., a programmable genome editing protein such as a CRISPR/Cas protein). The donor DNA will contain sufficient homology (% identity) to a genomic sequence at the target site, e.g. 70% or more (such as 80% or more, 85% or more, 90% or more, 95% or more, or 98% or more) percent nucleotide sequence identity with the nucleotide sequence of the target site (e.g., nucleotide sequence identity with sequences flanking the cleavage site, e.g. within about 50 bases or less of the cleavage site, e.g. within about 30 bases, within about 15 bases, within about 10 bases, within about 5 bases, or immediately flanking the cleavage site) to support homologous recombination between the donor DNA and the target DNA (e.g., genomic DNA) to which it bears homology. In some cases, the donor DNA is a single-stranded donor DNA. In some cases, the donor DNA is a double-stranded donor DNA.

In some cases, the donor DNA is 25 or more nucleotides (nt) (base pairs if the donor DNA is double stranded) (e.g., 50 or more, 100 or more, 200 or more, 500 or more, 1000 or more, or 2500 or more nt) in length. In some cases, the donor DNA has 25 or more nucleotides (nt) (base pairs if the donor DNA is double stranded) (e.g., 50 or more, 100 or more, 200 or more, 500 or more, 1000 or more, or 2500 or more nt) of sequence homology between the donor DNA and a target sequence (e.g., a target genomic sequence). In some cases the donor DNA is 25 nt to 5 kb long (base pair if it is double stranded) (e.g. 25 nt to 3 kb, 25 nt to 2 kb, 25 nt to 1 kb, 25 nt to 800 nt, 25 nt to 600 nt, 25 nt to 500 nt, 25 nt to 400 nt, 50 nt to 5 kb, 50 nt to 3 kb, 50 nt to 2 kb, 50 nt to 1 kb, 50 nt to 800 nt, 50 nt to 600 nt, 50 nt to 500 nt, 50 nt to 400 nt, 100 nt to 5 kb, 100 nt to 3 kb, 100 nt to 2 kb, 100 nt to 1 kb, 100 nt to 800 nt, 100 nt to 600 nt, 100 nt to 500 nt, 100 nt to 400 nt, 200 nt to 5 kb, 200 nt to 3 kb, 200 nt to 2 kb, 200 nt to 1 kb, 200 nt to 800 nt, 200 nt to 600 nt, 200 nt to 500 nt, or 200 nt to 400 nt long).

The donor sequence is typically not identical to the genomic sequence that it replaces. Instead, the donor sequence may contain at least one or more single base changes, insertions, deletions, inversions or rearrangements with respect to the genomic sequence, so long as sufficient homology is present to support homologous recombination. In some cases, the donor sequence comprises a non-homologous sequence flanked by two regions of homology, such that homologous recombination between the target DNA region and the two flanking sequences results in insertion of the non-homologous sequence at the target region. Donor DNAs may also include a vector backbone containing sequences that are not homologous to the target DNA region of interest and that are not intended for insertion into the DNA region of interest. Generally, the homologous region(s) of a donor sequence can have at least 50% (e.g., at least 60%, 70%, 80%, 90%, 95%, 98%, 99%, or 99.5%) nucleotide sequence identity to a genomic sequence with which recombination is desired.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein).

The donor sequence may be provided to the cell as single-stranded (ss) or double-stranded (ds) DNA. It may be introduced into a cell in linear or circular form. If introduced in linear form, the ends of the donor sequence may be protected (e.g., from exonucleolytic degradation) by methods known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and 0-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a recombinant vector comprising additional sequences such as, for example, replication origins, promoters and genes encoding antibiotic resistance.

Lipids

In some cases, a composition of the present disclosure comprises: a) an endosomal disruptor of the present disclosure; b) a macromolecule to be delivered to a cell; and c) a lipid, a lipid, a lipidoid, a liposome, a lipid nanoparticle, a core-shell nanoparticle, or a lipoplex.

For example, in some cases, a composition of the present disclosure comprises: a) an endosomal disruptor; b) a gene-editing enzyme, or a nucleic acid comprising a nucleotide sequence encoding a gene-editing enzyme; c) a guide RNA; and d) a lipid, a lipid, a lipidoid, a liposome, a lipid nanoparticle, or a lipoplex.

A composition of the present disclosure can include one or more of a liposome, a lipoplex, and a lipid nanoparticle. As one example, a composition of the present disclosure comprises: a) an endosomal disruptor of the present disclosure; b) a macromolecule (e.g., a gene-editing enzyme, or a nucleic acid comprising a nucleotide sequence encoding a gene-editing enzyme; a guide RNA); and c) a liposome. Liposomes are artificially-prepared vesicles which may primarily be composed of a lipid bilayer. Liposomes can be of various sizes. Suitable liposomes include, e.g.: a multilamellar vesicle (MLV) which may be hundreds of nanometers in diameter and may contain a series of concentric bilayers separated by narrow aqueous compartments; a small unicellular vesicle (SUV) which may be smaller than 50 nm in diameter; and a large unilamellar vesicle (LUV) which may be between 50 and 500 nm in diameter.

In some cases, a composition of the present disclosure comprises one or more cationic lipids. Cationic lipids that are suitable for inclusion in a composition of the present disclosure can be any of a number of lipid species which carry a net positive charge at physiological pH. Such lipids include, but are not limited to, N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxy-prop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3β-oxy)-3'-oxapentoxy)-3-dimethy-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-Dilinoleylcarbamyl-3-dimethylaminopropane (DLincarbDAP), 1,2-Dilinoleoylcarbamyl-3-dimethylaminopropane (DLinCDAP), and mixtures thereof. A number of these lipids and related analogs have been described in U.S. Patent Publication Nos. 20060083780 and 20060240554; U.S. Pat. Nos. 5,208,036; 5,264,618; 5,279,833; 5,283,185; 5,753,613; and 5,785,992; and PCT Publication No. WO 96/10390, the disclosures of which are each herein incorporated by reference in their entirety for all purposes. Additionally, a number of commercial preparations of cationic lipids are available and can be used. These include, e.g., LIPOFECTIN™ (commercially available cationic liposomes comprising DOTMA and DOPE, from GIBCO/BRL, Grand Island, N.Y., USA); LIPOFECTAMINE™ (commercially available cationic liposomes comprising DOSPA and DOPE, from GIBCO/BRL); and TRANSFECTAM™ (commercially available cationic liposomes comprising DOGS from Promega Corp., Madison, Wis., USA).

In some cases, a composition of the present disclosure comprises one or non-cationic lipids. Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids can be acyl groups derived from fatty acids having $C_{10}$-$C_{24}$ carbon chains, e.g., lauroyl, myristoyl, palmitoyl, stearoyl, or oleoyl. Additional examples of suitable non-cationic lipids include sterols such as cholesterol and derivatives thereof such as cholestanol, cholestanone, cholestenone, coprostanol, cholesteryl-2'-hydroxyethyl ether, cholesteryl-4'-hydroxybutyl ether, and mixtures thereof.

As an example, in some cases, a composition of the present disclosure comprises: a) an endosomal disruptor; b) a gene-editing enzyme, or a nucleic acid comprising a nucleotide sequence encoding a gene-editing enzyme; c) a guide RNA; and d) a liposome (e.g., a cationic liposome). As another example, in some cases, a composition of the present disclosure comprises: a) an endosomal disruptor; b) a gene-editing enzyme, or a nucleic acid comprising a nucleotide sequence encoding a gene-editing enzyme; c) a guide RNA; d) a donor DNA template; and e) a liposome (e.g., a cationic liposome).

In some cases, a composition of the present disclosure comprises a lipid nanoparticle. For example, a lipid nanoparticle can comprise a macromolecule to be delivered to a cell. For example, in some cases, a composition of the present disclosure comprises: a) an endosomal disruptor; and b) a lipid nanoparticle comprising: i) a gene-editing enzyme, or a nucleic acid comprising a nucleotide sequence encoding a gene-editing enzyme; and ii) a guide RNA. As another example, in some cases, a composition of the present disclosure comprises: a) an endosomal disruptor; and b) a lipid nanoparticle comprising: i) a gene-editing enzyme, or a nucleic acid comprising a nucleotide sequence encoding a gene-editing enzyme; ii) a guide RNA; and iii) a donor template DNA.

A lipid nanoparticle can comprise a polymeric material. Suitable polymeric materials include, e.g., polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material may be biodegradable and/or biocompatible. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), and trimethylene carbonate, polyvinylpyrrolidone. The lipid nanoparticle may be coated or associated with a co-polymer such as, but not limited to, a block co-polymer, and (poly(ethylene glycol))-(poly(propylene oxide))-(poly(ethylene glycol)) triblock copolymer.

The lipid nanoparticle can be a solid lipid nanoparticle (SLN). A solid lipid nanoparticle (SLN) may be spherical with an average diameter between 10 nm to 1000 nm (e.g., from 1 nm to 100 nm, from 100 nm to 250 nm, from 250 nm to 500 nm, from 500 nm to 750 nm, or from 750 nm to 1000 nm). SLN can possess a solid lipid core matrix that can solubilize lipophilic molecules; and may be stabilized with surfactants and/or emulsifiers. In some cases, the lipid nanoparticle is a self-assembly lipid-polymer nanoparticle.

Pharmaceutical Compositions

In some cases, a composition of the present disclosure comprises, in addition to an endosomal disruptor and a macromolecule(s), a pharmaceutically acceptable excipient.

A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc.

A composition of the present disclosure can include, e.g., pharmaceutical grades of mannitol, lactose, starch, magnesium stearate, sodium saccharin, talcum, cellulose, glucose, sucrose, magnesium, carbonate, and the like. A composition of the present disclosure may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

A composition of the present disclosure can be provided in the form of a solution, suspension, tablet, pill, capsule, powder, gel, cream, lotion, ointment, aerosol or the like. It is recognized that oral administration can require protection of the compositions from digestion. This is typically accomplished either by association of the composition with an agent that renders it resistant to acidic and enzymatic hydrolysis or by packaging the composition in an appropriately resistant carrier. Means of protecting from digestion are well known in the art.

Delivery Methods

The present disclosure provides a method of delivering a macromolecule (also referred to herein as a "cargo") to the cytoplasm of a cell (e.g., a eukaryotic cell), the method comprising contacting the cell with a composition of the present disclosure, where the composition comprises: i) an endosomal disruptor of the present disclosure; and ii a macromolecule. In some cases, the cell is in vitro. In other instances, the cell is in vivo. Once released from the endosome into the cytoplasm, a macromolecule can enter another subcellular compartment (e.g., the nucleus; a mitochondrion; etc.), can be inserted into the plasma membrane, can be inserted into the membrane of a subcellular compartment, or can be secreted from the cell. In some cases, once released from the endosome into the cytoplasm, a macromolecule enters the nucleus.

A macromolecule present in a composition of the present disclosure is released from the endosome into the cytoplasm, e.g., where the pH of the endosome is less than 7.0, e.g., where the pH of the endosome is from about 5.0 to about 6.9, from about 4.0 to about 5.0, from about 3.0 to about 4.0, from about 2.0 to about 3.0, or less than 2.0.

Target Cells

Target cells for use in the subject methods may include cells obtained from an in vitro source (e.g., a suspension of cells from laboratory cells grown in culture) or from an in vivo source (e.g., a vertebrate, an invertebrate, a mammalian subject, a human subject, etc.). In some embodiments, a target cell is obtained from an in vitro source. In vitro sources include, but are not limited to, environmental samples that contain eukaryotic (e.g., mammalian, fungal, etc.) cells, eukaryotic cell cultures (e.g., cultures of established cell lines, cultures of known or purchased cell lines, cultures of immortalized cell lines, cultures of primary cells, cultures of laboratory yeast, etc.), tissue cultures, and the like.

In some embodiments, the target cell is obtained from an in vivo source which can include samples obtained from tissues (e.g., cell suspension from a tissue biopsy, cell suspension from a tissue sample, bone marrow etc.) and/or body fluids (e.g., whole blood, fractionated blood, plasma, serum, saliva, lymphatic fluid, interstitial fluid, etc.). In vivo sources include living multi-cellular organisms. In some instances, the target cell is obtained from a patient diagnosed as having a disease or condition. In some instances, the target cell may be obtained from a subject suspected of having a disease or condition. In some instances, the target cell is obtained from a normal subject. In some cases, the target cell is present in an organ (e.g., an ex vivo organ).

In some cases, the target cell(s) is in vivo, e.g., present in an individual. Suitable individuals include, but are not limited to, humans; non-human mammals; mammals (e.g., felines such as cats; canines such as dogs; equines such as horses; ungulates; bovines such as cows; ovines such as sheep; caprines such as goats; and the like); insects; arthropods; arachnids; birds; amphibians; reptiles; invertebrates; vertebrates; fungi; plants; and the like.

Where the target cell(s) is in vivo in an individual, a method of the present disclosure can comprise administering to the individual a composition of the present disclosure. Any of a variety of routes of administration can be used, including, e.g., intravenous, intramuscular, subcutaneous, intratumoral, peritumoral, intracranial, etc. A composition of the present disclosure can be administered locally or systemically.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-36 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. An endosomal disruptor of the formula (I):
M-H-L-T (I), wherein:
M is a hydrophilic masking group;
H is selected from an aryl, a substituted aryl, a heteroaryl, a substituted heteroaryl, a saturated carbocycle, a substituted saturated carbocycle, a heterocycle and a substituted heterocycle;
L is a covalent bond or a linker; and
T is a hydrophilic tail group,
or a pharmaceutically acceptable salt or a solvate thereof.

Aspect 2. The endosomal disruptor of aspect 1, wherein M is an acetal group a thioacetal group or a dithioacetal group.

Aspect 3. The endosomal disruptor of aspect 1, wherein T is a polyethylene glycol (PEG) moiety.

Aspect 4. The endosomal disruptor of aspect 1, of the formula (II)

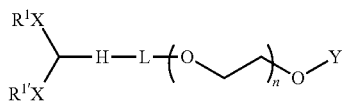

(II)

wherein:
$R^1$ and $R^{1'}$ are independently alkyl, substituted alkyl (e.g. substituted with heteroaryl, heterocycle, azide etc.), polyethylene glycol (PEG), substituted PEG, carbocycle, substituted carbocycle, heterocycle, substituted heterocycle;
or $R^1$ and $R^{1'}$ together with the carbon to which they are attached form a group selected from heterocycle, substituted heterocycle;
X is O or S;
H is selected from an aryl, a substituted aryl, a heteroaryl, a substituted heteroaryl, a saturated carbocycle, a substituted saturated carbocycle, a heterocycle and a substituted heterocycle;
L is a covalent bond or a linker;
n is an integer up to 500 Da; and
Y is selected from H, alkyl, substituted alkyl, an amino acid, a substituted amino acid, a polycation, or a pharmaceutically acceptable salt or a solvate thereof.

Aspect 5. The endosomal disruptor of any one of aspects 1 to 4, wherein H is selected from:

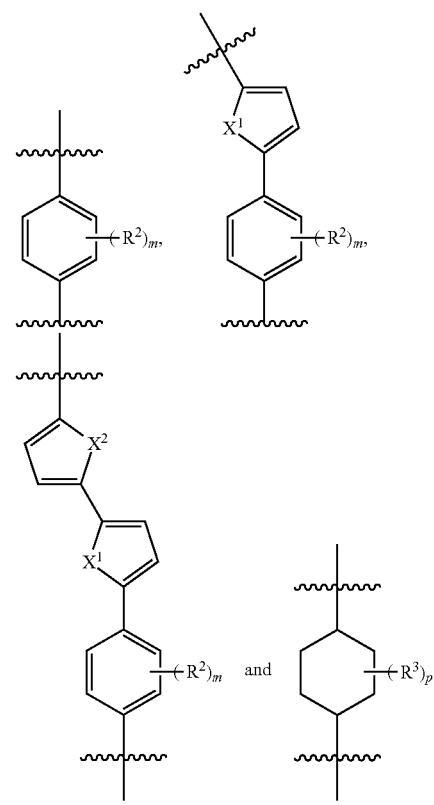

wherein:
$R^2$ and $R^3$ are each independently selected from the group consisting of OH, alkyl, substituted alkyl, alkenyl, substituted alkenyl, alkoxy, substituted alkoxy, —$OCF_3$, halogen, amine, substituted amine, amide, azide, heterocycle and substituted heterocycle;
$X^1$ and $X^2$ are each independently selected from a carbon atom or a heteroatom (e.g. S, O, N);
m is an integer from 0 to 4; and
p is an integer from 0 to 8.

Aspect 6. The endosomal disruptor of any one of aspects 1 to 5, wherein L is selected from:

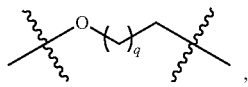
,

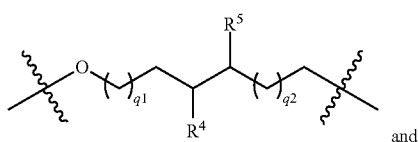
and

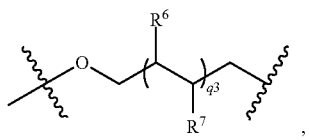
, wherein:
R⁴, R⁵, R⁶ and R⁷ are each independently selected from alkyl or substituted alkyl; and
q, q¹, q² and q³ are each independently an integer from 1 to 20.

Aspect 7. The endosomal disruptor of any one of aspects 1 to 6 of the formula (III):

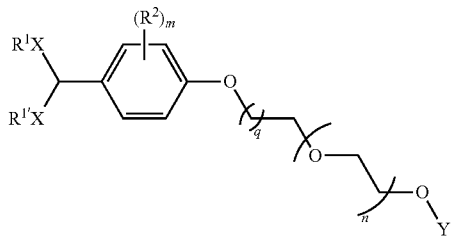
(III)

wherein:
R¹ and R¹' are independently alkyl, substituted alkyl (e.g. substituted with heteroaryl, heterocycle, azide etc.), polyethylene glycol (PEG), substituted PEG, carbocycle, substituted carbocycle, heterocycle, substituted heterocycle;
or R¹ and R¹' together with the carbon to which they are attached form a group selected from heterocycle, substituted heterocycle;
each R² are independently selected from the group consisting of OH, alkyl, substituted alkyl, alkenyl, substituted alkenyl, alkoxy, substituted alkoxy, —OCF₃, halogen, amine, substituted amine, amide, azide, heterocycle and substituted heterocycle;
X is O or S;
m is an integer from 0 to 4;
q is an integer from 1 to 20;
n is an integer up to 500 Da; and
Y is selected from H, alkyl, substituted alkyl, an amino acid, a substituted amino acid, a polycation, or a pharmaceutically acceptable salt or a solvate thereof.

Aspect 8. The endosomal disruptor of any one of aspects 1 to 7, wherein Y is a polycation selected from a cationic peptide, a cationic peptide derivative, linear synthetic polymer, branched synthetic polymer, polysaccharide, natural polymer, activated dendrimer and a non-activated dendrimer.

Aspect 9. The endosomal disruptor of aspect 8, wherein the polycation is a cationic peptide (e.g. polylysine).

Aspect 10. The endosomal disruptor of any one of aspects 1 to 9, wherein each X group is O.

Aspect 11. The endosomal disruptor of any one of aspects 1 to 10, wherein $R^1$ and $R^{1'}$ are independently selected from:

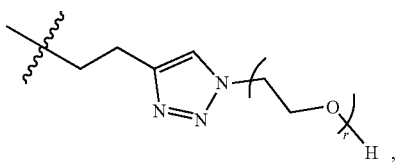
,

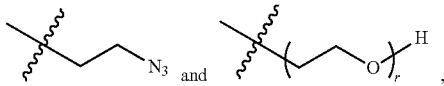
, wherein:
r is an integer from 1 to 10.

Aspect 12. The endosomal disruptor of aspect 11 wherein $R^1$ and $R^{1'}$ are both:

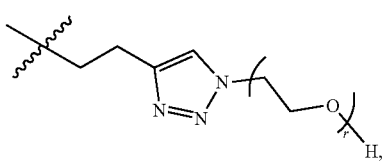

and r is 4.

Aspect 13. The endosomal disruptor of any one of aspects 1 to 12 selected from the following structures:
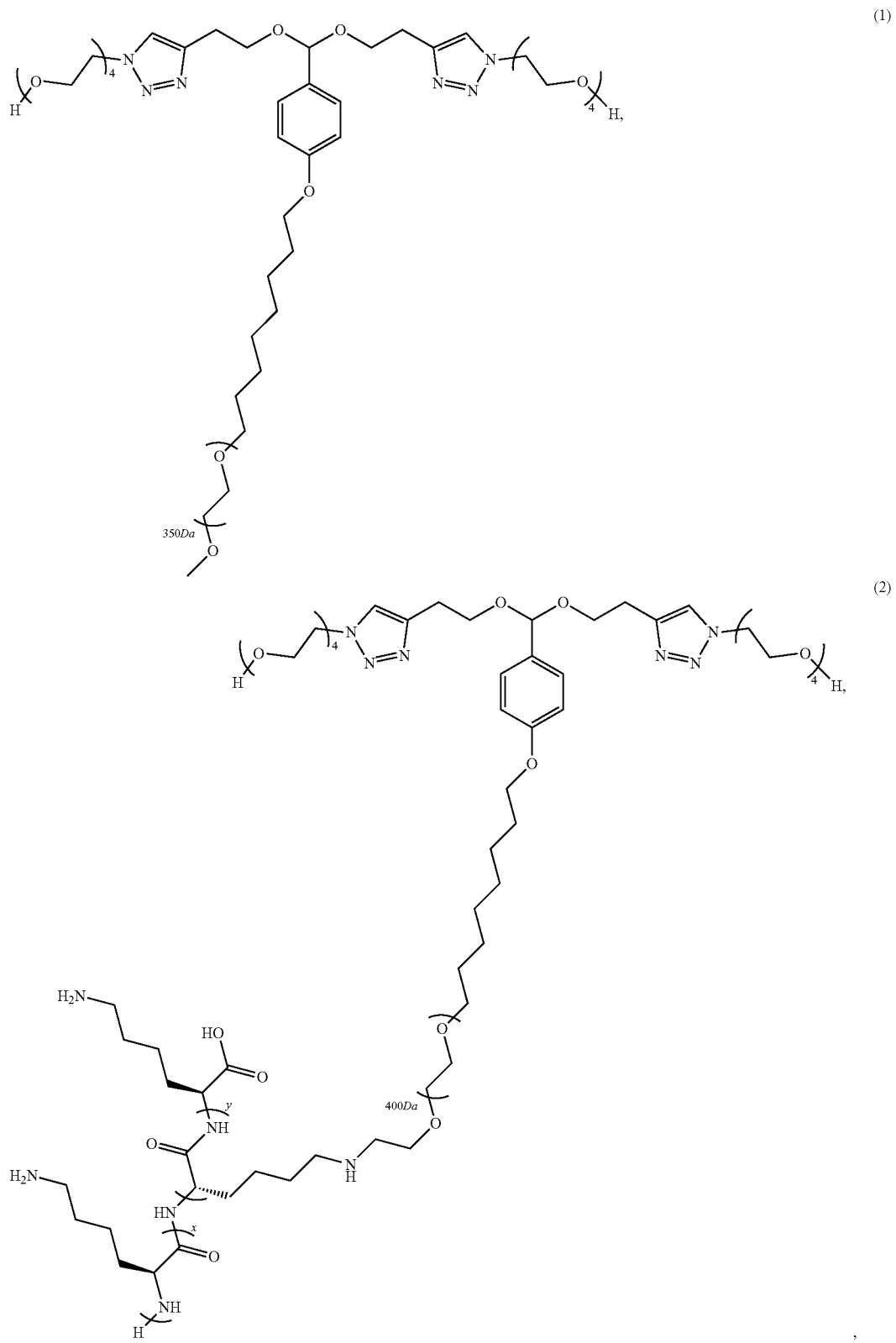
wherein x and y combined equal an integer from 25 to 30.

Aspect 14. An endosomal disruptor of the formula (I):

(M-Z-A-T)-Y    (I)

wherein:
M is a hydrophilic masking group;
Z is a cleavable linker capable of cleavage with an endosome to release M and produce an endosomal disrupting surfactant;
A is a masked hydrophobic group comprising:
  a cyclic group selected from an aryl, a substituted aryl, a heteroaryl, a substituted heteroaryl, a saturated carbocycle, a substituted saturated carbocycle, a heterocycle and a substituted heterocycle; and
  a hydrophobic chain;
T is a hydrophilic tail group: and
Y is an optional group selected from a terminal group, a linker, a chemoselective tag (e.g. configured to conjugate a cell targeting agent or a macromolecule), a member of a specific binding pair, a linked biomolecule and a linked cell delivery agent;
or a pharmaceutically acceptable salt or a solvate thereof.

Aspect 15. The endosomal disruptor of aspect 14, wherein M is an inert hydrophilic masking group.

Aspect 16. The endosomal disruptor of aspect 14, of the formula (II):

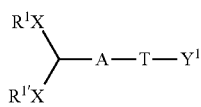

wherein:
$R^1$ and $R^{1'}$ are independently selected from alkyl, alkenyl, heterocycle, substituted heterocycle, substituted heterocycle, carbocycle, substituted carbocycle, polyethylene glycol (PEG), substituted PEG, alkyl-$Y^1$ and alkenyl-$Y^1$, wherein $Y^1$ is selected from the group consisting of, heterocycle, substituted heterocycle, heteroaryl, substituted heteroaryl, carbocycle, substituted carbocycle, polyethylene glycol (PEG), modified PEG, and wherein each $Y^1$ group is optionally substituted with one or more additional groups selected from alkyl, substituted alkyl, PEG and modified PEG;
or $R^1$ and $R^{1'}$ together with the carbon to which they are attached form a group selected from heterocycle and substituted heterocycle;
X is O or S;
A is a masked hydrophobic group comprising:
  a cyclic group selected from an aryl, a substituted aryl, a heteroaryl, a substituted heteroaryl, a saturated carbocycle, a substituted saturated carbocycle, a heterocycle and a substituted heterocycle; and
  a hydrophobic chain;
T is a hydrophilic tail selected from a polyethylene glycol (PEG), a modified PEG, a oligoethyleneglycol, a phosphate, a phosphonate, a boric acid, a carboxylate, a sulfate, a sulfonate, an amine, a glycerol, a sugar, an amino acid, a substituted amino acid; and
$Y^1$ is an optional group selected from a terminal group, a linker, a chemoselective tag (e.g. configured to conjugate a cell targeting agent or a macromolecule), a member of a specific binding pair, a linked biomolecule and a linked cell delivery agent;
or a pharmaceutically acceptable salt or a solvate thereof.

Aspect 17. The endosomal disruptor of aspect 16, of the formula (III)

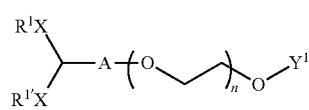

wherein:
$R^1$ and $R^{1'}$ are independently selected from alkyl, alkenyl, heterocycle, substituted heterocycle, substituted heterocycle, carbocycle, substituted carbocycle, polyethylene glycol (PEG), substituted PEG, alkyl-$Y^1$ and alkenyl-$Y^1$, wherein $Y^1$ is selected from the group consisting of, heterocycle, substituted heterocycle, heteroaryl, substituted heteroaryl, carbocycle, substituted carbocycle, polyethylene glycol (PEG), modified PEG, and wherein each $Y^1$ group is optionally substituted with one or more additional groups selected from alkyl, substituted alkyl, PEG and modified PEG;
or $R^1$ and $R^{1'}$ together with the carbon to which they are attached form a group selected from heterocycle and substituted heterocycle;
X is O or S;
A is a masked hydrophobic group comprising:
  a cyclic group selected from an aryl, a substituted aryl, a heteroaryl, a substituted heteroaryl, a saturated carbocycle, a substituted saturated carbocycle, a heterocycle and a substituted heterocycle; and
  a hydrophobic chain;
n is an integer up to 500 Da; and
$Y^1$ is selected from a terminal group, a linker, a chemoselective tag (e.g. configured to conjugate a cell targeting agent or a macromolecule), a member of a specific binding pair, a linked biomolecule and a linked cell delivery agent;
or a pharmaceutically acceptable salt or a solvate thereof.

Aspect 18. The endosomal disruptor of any one of aspects 14 to 17, wherein A comprises a cyclic group selected from:

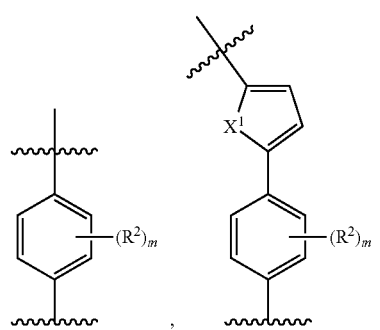

-continued

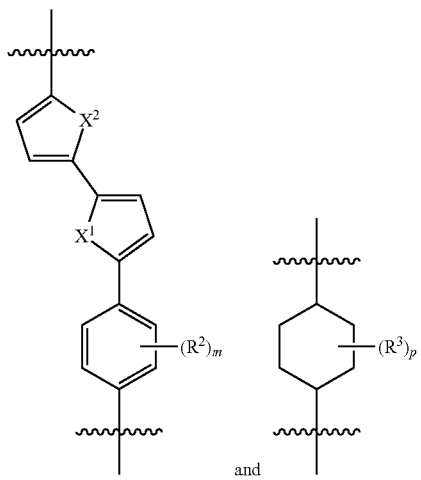

and wherein:

R² and R³ are each independently selected from the group consisting of OH, alkyl, substituted alkyl, alkenyl, substituted alkenyl, alkoxy, substituted alkoxy, —OCF₃, halogen, amine, substituted amine, amide, azide, heterocycle and substituted heterocycle; X¹ and X² are each independently selected from a carbon atom or a heteroatom (e.g. S, O, N);

m is an integer from 0 to 4; and p is an integer from 0 to 8.

Aspect 19. The endosomal disruptor of any one of aspects 14 to 18, wherein A comprises a linear or branched hydrophobic chain selected from, alkyl, alkenylene, alkynylene, arylene, alkarylene, aralkylene, alkoxy and alkamine.

Aspect 20. The endosomal disruptor of any one of aspects 14 to 19, wherein A comprises a hydrophobic chain selected from:

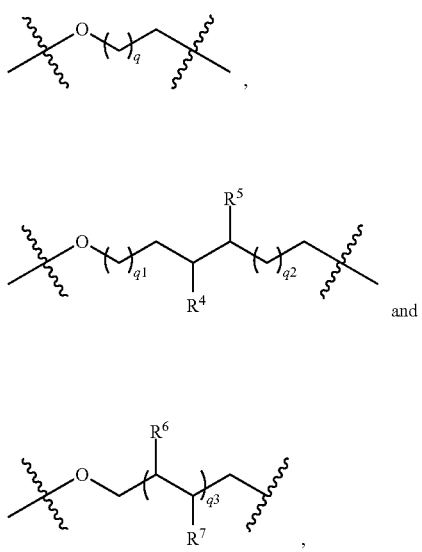

wherein: R⁴, R⁵, R⁶ and R⁷ are each independently selected from alkyl or substituted alkyl; and q, q¹, q² and q³ are each independently an integer from 1 to 20.

Aspect 21. The endosomal disruptor of any one of aspects 14 to 20 of the formula (IV):

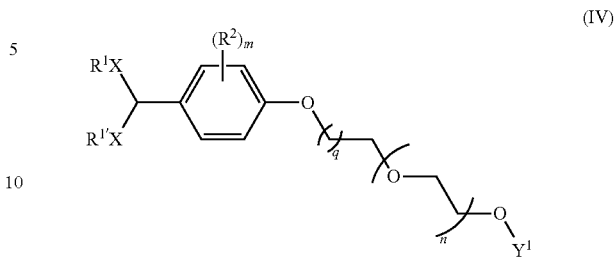

(IV)

wherein:

R¹ and R¹' are independently selected from alkyl, alkenyl, heterocycle, substituted heterocycle, substituted heterocycle, carbocycle, substituted carbocycle, polyethylene glycol (PEG), substituted PEG, alkyl-Y¹ and alkenyl-Y¹, wherein Y¹ is selected from the group consisting of, heterocycle, substituted heterocycle, heteroaryl, substituted heteroaryl, carbocycle, substituted carbocycle, polyethylene glycol (PEG), modified PEG, and wherein each Y¹ group is optionally substituted with one or more additional groups selected from alkyl, substituted alkyl, PEG and modified PEG;

or R¹ and R¹' together with the carbon to which they are attached form a group selected from heterocycle and substituted heterocycle;

each R² are independently selected from the group consisting of OH, alkyl, substituted alkyl, alkenyl, substituted alkenyl, alkoxy, substituted alkoxy, —OCF₃, halogen, amine, substituted amine, amide, azide, heterocycle and substituted heterocycle;

X is O or S;

m is an integer from 0 to 4;

q is an integer from 1 to 20;

n is an integer up to 500 Da; and

Y¹ is selected from a terminal group, a linker, a chemoselective tag (e.g. configured to conjugate a cell targeting agent or a macromolecule), a linked biomolecule, a member of a specific binding pair, and a linked cell delivery agent; or a pharmaceutically acceptable salt or a solvate thereof.

Aspect 23. The endosomal disruptor of any one of aspects 14 to 22, wherein Y or Y¹ is a chemoselective tag comprising a group selected from amine and carboxylic acid.

Aspect 24. The endosomal disruptor of any one of aspects 14 to 23, wherein Y or

Y¹ comprises a chemoselective tag configured to conjugate to a peptide, a protein or a polycation selected from a cationic peptide, a cationic peptide derivative, linear synthetic polymer, branched synthetic polymer, polysaccharide, natural polymer, activated dendrimer and a non-activated dendrimer.

Aspect 25. The endosomal disruptor of aspect 24, wherein the polycation is a cationic peptide (e.g. polylysine).

Aspect 26. The endosomal disruptor of any one of aspects 14 to 25, wherein each X group is O.

Aspect 27. The endosomal disruptor of any one of aspects 14 to 26, wherein $R^1$ and $R^{1'}$ are both:
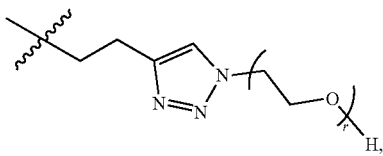
and r is an integer from 1 to 10.
Aspect 28. The endosomal disruptor of any one of aspects 14 to 26, wherein $R^1$ and $R^{1'}$ are both:
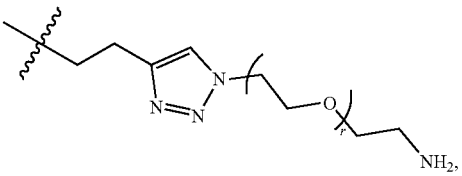
and r is an integer from 1 to 10.
Aspect 29. The endosomal disruptor of any one of aspects 14 to 28, having one of the following structures:
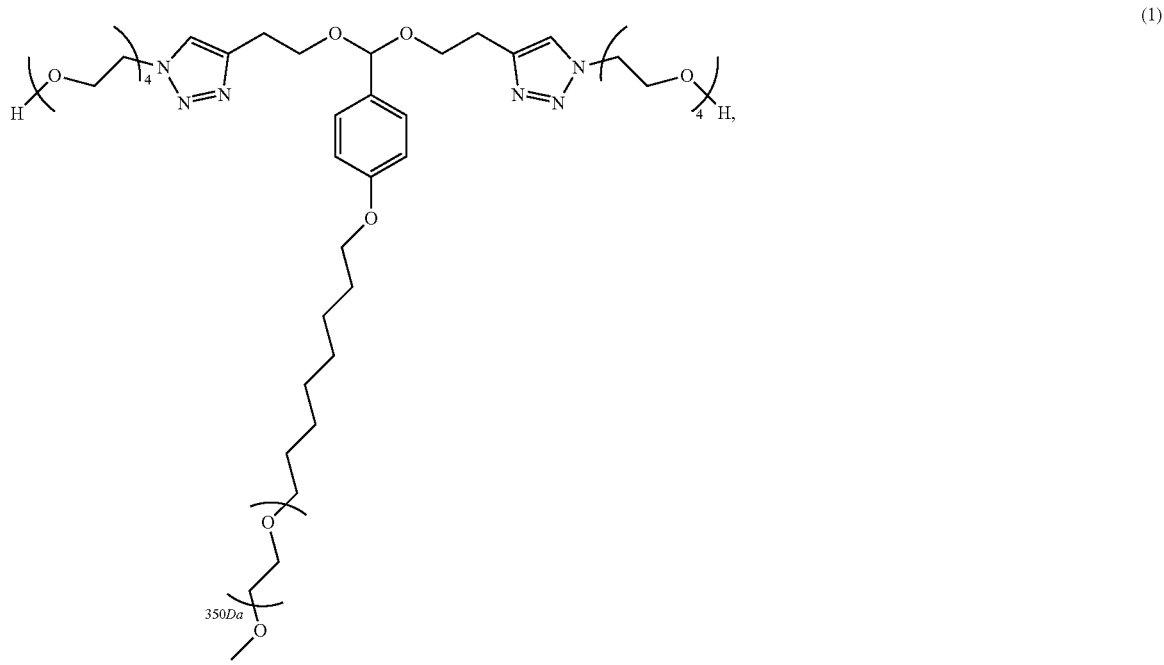
(1)
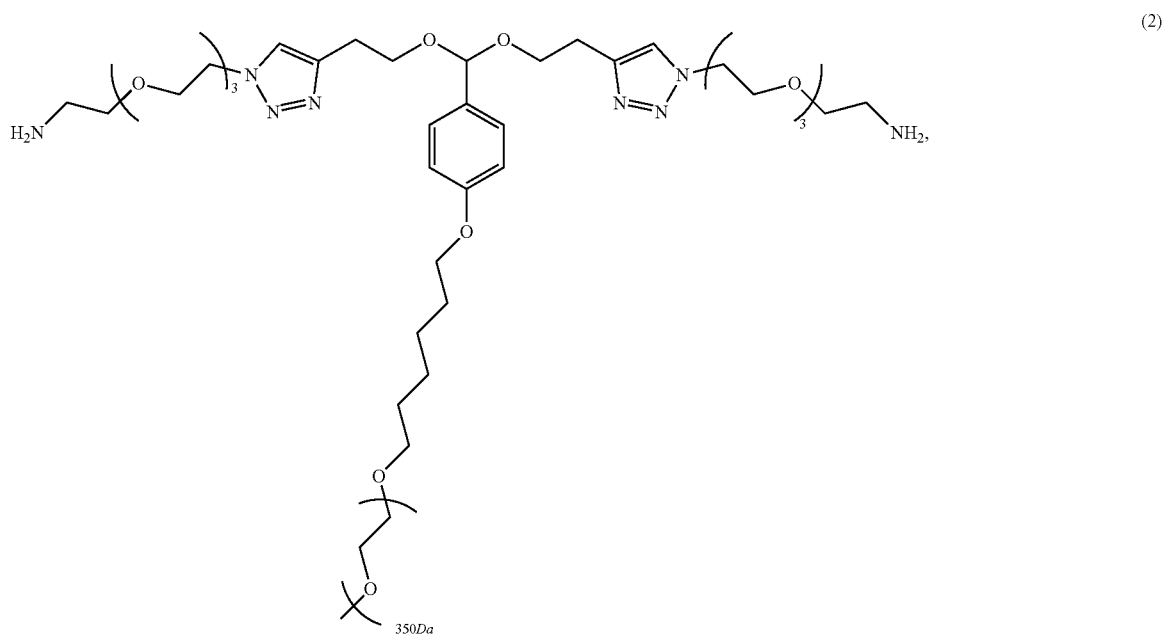
(2)

-continued (3)

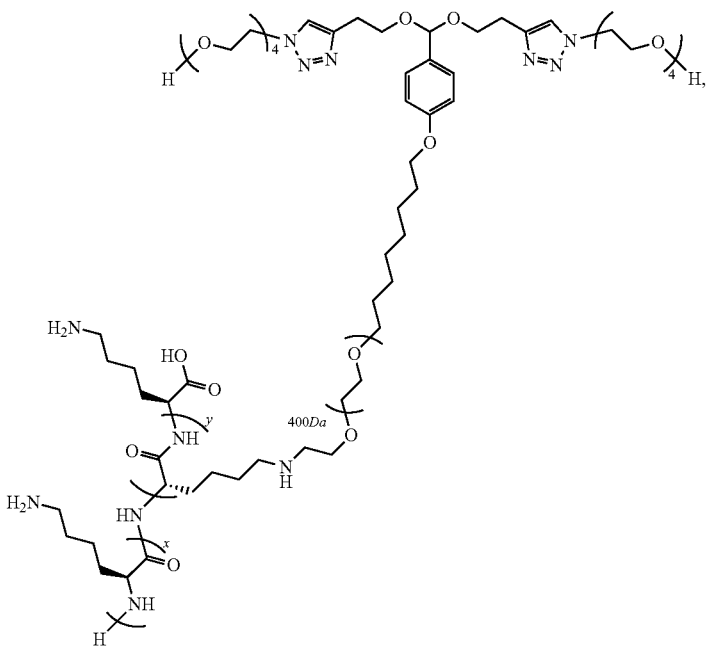

wherein x and y combined equal an integer from 25 to 30.

Aspect 30. The endosomal disruptor of aspect 14, of the formula (V):

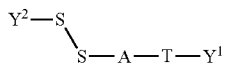

(V)

wherein:

S—S represents a disulfide linker;

$Y^2$ is a hydrophilic group optionally substituted with a group selected from a terminal group, a linker, a chemoselective tag (e.g. configured to conjugate a cell targeting agent or a macromolecule), a linked biomolecule and a linked cell delivery agent;

A is a masked hydrophobic group comprising:

a cyclic group selected from an aryl, a substituted aryl, a heteroaryl, a substituted heteroaryl, a saturated carbocycle, a substituted saturated carbocycle, a heterocycle and a substituted heterocycle; and a hydrophobic chain;

T is a hydrophilic tail selected from a polyethylene glycol (PEG), a modified PEG, a oligoethyleneglycol, a phosphate, a phosphonate, a boric acid, a carboxylate, a sulfate, a sulfonate, an amine, an amide, a glycerol, a sugar, an amino acid, a substituted amino acid; and $Y^1$ is an optional group selected from a terminal group, a linker, a member of a specific binding pair, a chemoselective tag (e.g. configured to conjugate a cell targeting agent or a macromolecule), a linked biomolecule and a linked cell delivery agent; or a pharmaceutically acceptable salt or a solvate thereof.

Aspect 31. The endosomal disruptor of aspect 30, of the formula (VI):

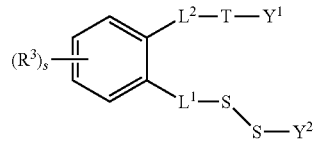

(VI)

wherein:

$L^1$ and $L^2$ are each independently selected from, a covalent bond, an amide group, an ester group, a ketone group and a hydrophobic chain, wherein at least one of $L^1$ or $L^2$ is a hydrophobic chain;

S—S represents a disulfide linker;

$Y^2$ is selected from a hydrophilic group optionally substituted with a group selected from a terminal group, a linker, a chemoselective tag (e.g. configured to conjugate a cell targeting agent or a macromolecule), a linked biomolecule and a linked cell delivery agent;

each $R^3$ are independently selected from the group consisting of OH, alkyl, substituted alkyl, alkenyl, substituted alkenyl, alkoxy, substituted alkoxy, —$OCF_3$, halogen, amine, substituted amine, amide, azide, heterocycle and substituted heterocycle;

T is a hydrophilic tail selected from a polyethylene glycol (PEG), a modified PEG, a oligoethyleneglycol, a phosphate, a phosphonate, a boric acid, a carboxylate, a sulfate, a sulfonate, an amine, an amide, a glycerol, a sugar, an amino acid, a substituted amino acid;

$Y^1$ is an optional group selected from a terminal group, a linker, a chemoselective tag (e.g. configured to conjugate a cell targeting agent or a macromolecule), a member of a specific binding pair, a linked biomolecule and a linked cell delivery agent; and s is an integer from 0 to 4,
or a pharmaceutically acceptable salt or a solvate thereof.

Aspect 32. The endosomal disruptor of aspect 31, of the formula (VII):

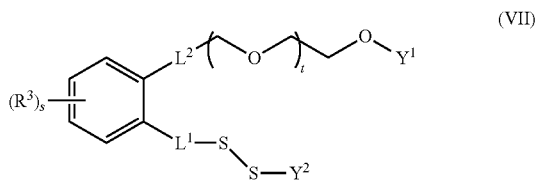

wherein:
L$^1$ and L$^2$ are each independently selected from, a covalent bond, an amide group, an ester group, a ketone group, an amine group, an alkoxy group, and a hydrophobic chain, wherein at least one of L$^1$ or L$^2$ is a hydrophobic chain;
S—S represents a disulfide linker;
Y$^2$ is selected from a hydrophilic group optionally substituted with a group selected from a terminal group, a linker, a chemoselective tag (e.g. configured to conjugate a cell targeting agent or a macromolecule), a linked biomolecule and a linked cell delivery agent;
each R$^3$ are independently selected from the group consisting of OH, alkyl, substituted alkyl, alkenyl, substituted alkenyl, alkoxy, substituted alkoxy, —OCF$_3$, halogen, amine, substituted amine, amide, azide, heterocycle and substituted heterocycle;
Y$^1$ is selected from a terminal group, a linker, a chemoselective tag (e.g. configured to conjugate a cell targeting agent or a macromolecule), a member of a specific binding pair, a linked biomolecule and a linked cell delivery agent;
s is an integer from 0 to 4; and
t is an integer up to 2000 Da,
or a pharmaceutically acceptable salt or a solvate thereof.

Aspect 33. The endosomal disruptor of any one of aspects 31-32, wherein at least one of L$^1$ or L$^2$ is a linear or branched hydrophobic chain selected from amide, ester, ketone, alkyl, alkenylene, alkynylene, arylene, alkarylene, aralkylene, alkoxy and alkamine.

Aspect 34. The endosomal disruptor of any one of aspects 31-33, wherein L$^1$ is an alkyl or an alkamine, wherein the alkyl or alkamine contains a C$_2$-C$_{10}$ alkyl chain.

Aspect 35. The endosomal disruptor of aspect 31, of the formula (VIII):

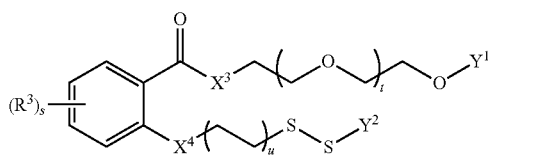

wherein:
X$^3$ and X$^4$ are each independently selected from CH$_2$, NH and O; each R$^3$ are independently selected from the group consisting of OH, alkyl, substituted alkyl, alkenyl, substituted alkenyl, alkoxy, substituted alkoxy, —OCF$_3$, halogen, amine, substituted amine, amide, azide, heterocycle and substituted heterocycle;
Y$^1$ is selected from a terminal group, a linker, a chemoselective tag (e.g. configured to conjugate a cell targeting agent or a macromolecule), a linked biomolecule and a linked cell delivery agent;

Y$^2$ is selected from a hydrophilic group optionally substituted with a group selected from a terminal group, a linker, a chemoselective tag (e.g. configured to conjugate a cell targeting agent or a macromolecule), a member of a specific binding pair, a linked biomolecule and a linked cell delivery agent;
s is an integer from 0 to 4;
t is an integer such that the mass of the group described by t is up to 2000 Da, or t is an integer between 1 and 50; and
u is an integer from 1 to 10,
or a pharmaceutically acceptable salt or a solvate thereof.

Aspect 36. The endosomal disruptor of aspect 35, wherein X3 is NH.

Aspect 37. The endosomal disruptor of aspect 35 or 36, wherein X$^4$ is NH.

Aspect 38. The endosomal disruptor of any one of aspects 30-37, wherein Y$^2$ is:

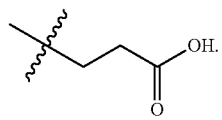 [SMILES: *CCC(=O)O]

Aspect 39. The endosomal disruptor according to any one of aspects 19-38 of the formula:

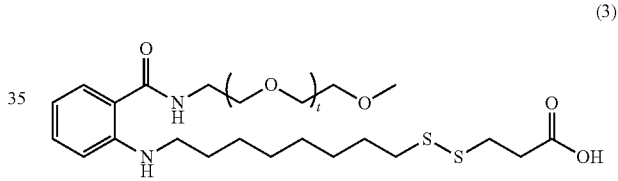

wherein, t is an integer such that the mass of the group described by t is approximately 1000 Da, or t is an integer from 1 to 25.

Aspect 40. A pharmaceutical composition, comprising: a) an endosomal disruptor of any one of aspects 1-39; and b) a pharmaceutically acceptable excipient.

Aspect 41. A pharmaceutical composition, comprising: a) an endosomal disruptor of any one of aspects 1-39; b) one or more macromolecules; and c) a pharmaceutically acceptable excipient.

Aspect 42. A composition comprising: a) an endosomal disruptor of any one of aspects 1-39; and b) one or more macromolecules.

Aspect 43. The composition of aspect 42, wherein the one or more macromolecules is a nucleic acid.

Aspect 44. The composition of aspect 43, wherein the nucleic acid is DNA.

Aspect 45. The composition of aspect 43, wherein the nucleic acid is RNA.

Aspect 46. The composition of aspect 43, wherein the nucleic acid is selected from a DNA, an mRNA, an siRNA, an miRNA, and a guide RNA.

Aspect 47. The composition of aspect 42, wherein the one or more macromolecules is a polypeptide.

Aspect 48. The composition of aspect 47, wherein the polypeptide is an enzyme, a transcription regulator, a translation regulator, a cytokine, a hormone, or an antibody.

Aspect 49. The composition of aspect 47, wherein the polypeptide is a genome-editing enzyme.

Aspect 50. The composition of aspect 49, wherein the genome-editing enzyme is an enzymatically active type II CRISPR/Cas polypeptide, a zinc finger nuclease, a TALEN, or an enzymatically inactive type II CRISPR/Cas polypeptide.

Aspect 51. The composition of aspect 49, wherein the genome-editing enzyme is an RNA-guided endonuclease selected from a type II CRISPR/Cas polypeptide, a type V CRISPR/Cas polypeptide, and a type VI CRISPR/Cas polypeptide.

Aspect 52. The composition of aspect 42, wherein the one or more macromolecules comprise: i) an RNA-guided endonuclease; and ii) a guide RNA.

Aspect 53. The composition of aspect 51, wherein the guide RNA is a single-molecule guide RNA.

Aspect 54. The composition of aspect 42, wherein the one or more macromolecules comprise: i) an RNA-guided endonuclease; ii) a guide RNA; and iii) a donor DNA.

Aspect 55. A method of delivering a macromolecule to the cytoplasm of a eukaryotic cell, the method comprising contacting the cell with a composition of any one of aspects 42-54.

Aspect 56. The method of aspect 55, wherein the eukaryotic cell is in vitro.

Aspect 57. The method of aspect 55, wherein the eukaryotic cell is in vivo in a human or non-human organism.

Aspect 58. The method of aspect 57, comprising administering the composition to the organism.

Aspect 59. The method of any one of aspects 55-5857, wherein the eukaryotic cell is selected from the group consisting of: a plant cell, a fungal cell, a single cell eukaryotic organism, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 60. The method of aspect 58, wherein the organism is a human

Aspect 61. The method of aspect 58, wherein the organism is a non-human organism.

Aspect 62. The method of aspect 58, wherein the non-human organism is selected from the group consisting of a plant, a fungus, a non-human mammal, an insect, a reptile, a bird, a fish, a parasite, an arthropod, an invertebrate, and a vertebrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Introduction

Strategies for generating endosomal disruptors have been developed based upon reversibly caging the hydrophobic groups of triton-X like surfactants, e.g. triton X-100, with polyethylene glycol (PEG) chains. Such endosomal disruptors can also be referred to as caged surfactants. In some such endosomal disruptors, the hydrophobic region of the triton-X like surfactant can be "masked" by two hydrophilic PEG chains that have been conjugated to the triton-X like surfactant via acetal linkages. Such endosomal disruptors can be configured to not disrupt a membrane, e.g. a cell membrane, at physiological pH, e.g. a pH of 7.4, but can be efficient membrane disruptive agents at a more acidic pH of 6.0 and below. In addition, such endosomal disruptors can be readily incorporated into delivery vehicles due to their small size and mass, e.g. a mass of approximately 1000 Da or less.

In addition, the end of the two masking hydrophilic PEG chains can include various functional groups, e.g. a hydroxyl group or an amino group. Endosomal disruptors with amino groups at the end of each of the two PEG chains were found to complex plasmid DNA and increase its transfection into cells. The subject endosomal disruptors can be useful for drug delivery or molecular imaging. It was hypothesized that surfactants based on triton-X could be converted into pH sensitive membrane disruptive agents, and consequently selectively disrupt endosomes. Triton-X like surfactants are membrane disruptive agents, which only weigh 500, and are much smaller than peptide and polymer based endosomal disruptive agents. Inaddition, Triton-X like surfactants are composed of alkyl group and PEG chains, and are not antigenic, and can be repeatedly administered to subjects. Triton X like surfactants have the potential to be incorporated into efficient small molecule endosomal disruptive agents, and their relatively small size can make incorporating them into delivery vehicles less challenging than larger polymeric endosomal disruptive agents. However, triton-X itself can disrupts cell membranes even at pH 7.4. To convert Triton-X into a pH sensitive membrane disruptive agent, PEG chains were conjugated to its hydrophobic domain, via pH sensitive acetal linkage, generating exemplary caged surfactants.

The design of the caged surfactants is shown in FIG. 1A. The caged surfactants are composed of a Triton X like surfactant, which have a hydrophobic domain composed of a benzaldehyde-alkyl group and a hydrophilic portion composed of 8 PEG units. In addition, the caged surfactants have another two short PEG chains conjugated to the benzaldehyde-octyl group via an acid degradable acetal linkage. The caged surfactants are not membrane disruptive at pH 7.4 because the PEG chains prevent the hydrophobic domain from inserting into cell membranes. However, at pH 5.0, the acetal linkage of the caged surfactant hydrolyzes and exposes the hydrophobic domain allowing it to disrupt endosomes. The caged surfactants provide a general strategy for developing small molecule pH sensitive membrane disruptive agents, and because of their small size can be easily conjugated to therapeutics such as proteins and siRNA. In addition, the small size of the caged surfactants makes incorporating them into delivery vehicles synthetically accessible. A second generation caged surfactant was synthesized, which could assemble with nucleic acid drugs, by terminating its PEG chains with primary amines. The 2nd generation caged surfactant was able to complex DNA and deliver it efficiently into cells, and thus serves as a platform for new delivery vehicles.

The exemplary caged surfactants are composed of Triton X like surfactants that have their hydrophobic domains masked by a 2 short PEG chains. The molecular architecture and hydrophobic/hydrophilic balance of the caged surfactants provide for their endosome disrupting function. The sandwich structure of the hydrophobic chain ensures that at pH 7.4, it cannot penetrate the cell membrane. The caged surfactants also can be configured to hydrolyze rapidly at pH 5.0, but be stable at pH 7.4 to enable formulation with biomolecules. A methoxy-benzaldeyde acetal was initially selected as the linkage for the caged surfactants because of its rapid hydrolysis at pH 5.0 (t½<5 minutes) and relative stability at pH 7.4 (t½>4 hours). However, other cleavable groups could be utilized. The hydrolysis kinetics ensures that the caged surfactants cause minimal toxicity to cell membranes, but disrupt endosome before significant degradation of the contents have occurred. The hydrophobic domain of the caged surfactants contains a benzene ring and a hydrocarbon chain if e.g., 8, 10, 12 or 16 carbons, e.g., connected via an oxo —O— group, where these lengths were initially chosen because of their similarity to Triton-X, which has a 8 carbons. For Triton-X increasing the length of the hydrophobic chain can increase the membrane disruptive activity. Alkyl chains were investigated that were longer than 8. However, there can in some cases be a limit to the length of the hydrophobic domain chain, if the internal hydrophobic domain is too large then even at pH 7.4 it will cause membrane disruption, because the hydrophobic domain will be able to bend on itself and still penetrate the membrane, similar to bola-amphiphiles. Thus, the first generation caged surfactant were designed to assess, (1) can a triton-X like surfactant be made pH sensitive by reversible masking of their hydrophobic groups, and (2) what is the hydrophobic/hydrophilic balance in the caged surfactants that can obtain a desirable membrane disruptive efficiency along with pH sensitivity.

Example 1

General Synthetic Procedure

Scheme 1

A)

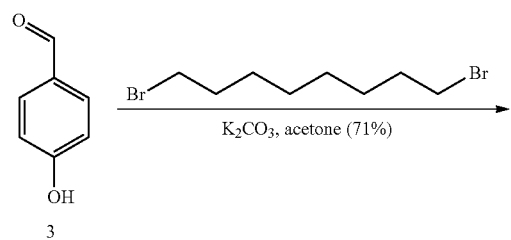

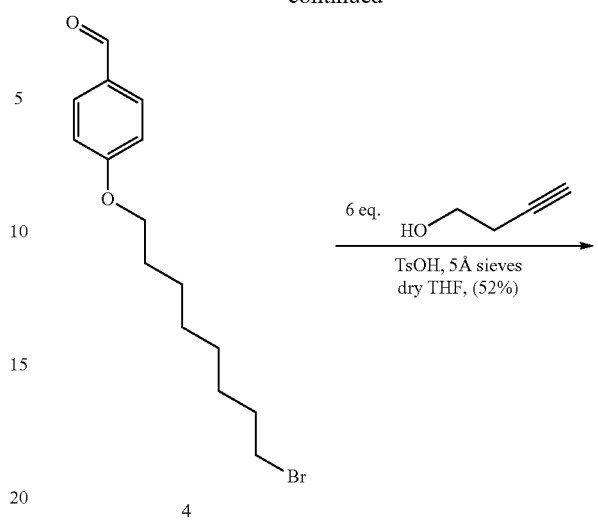

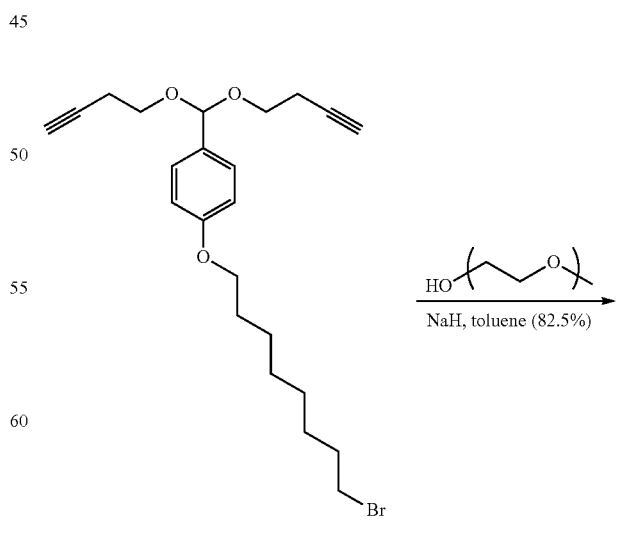

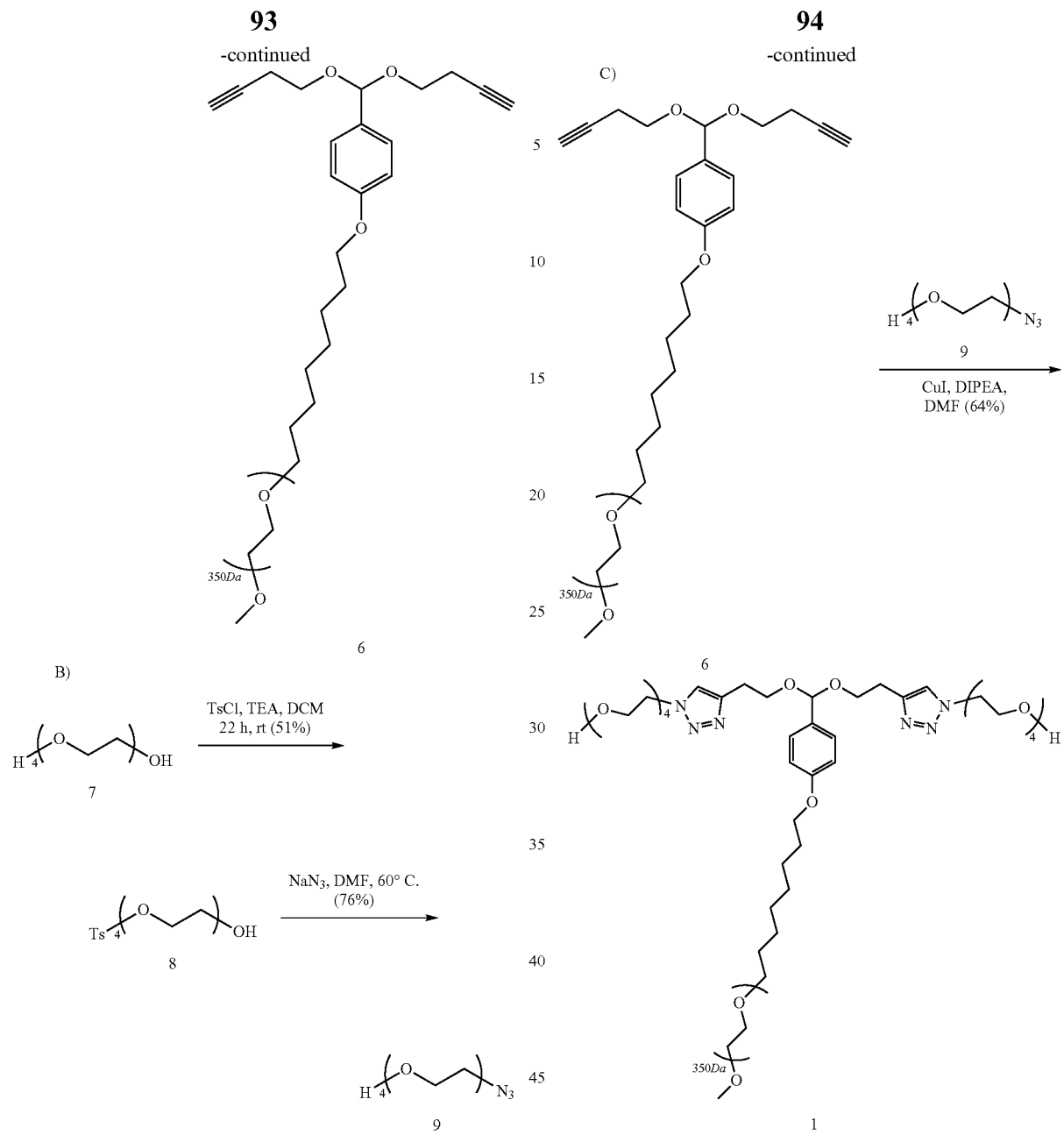
Scheme 2
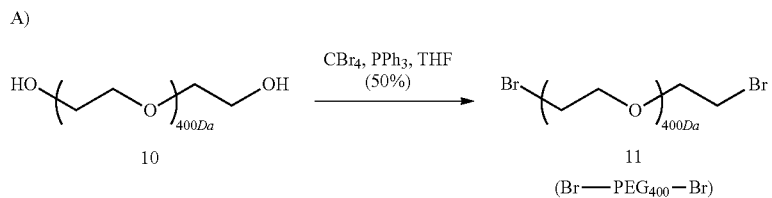

-continued
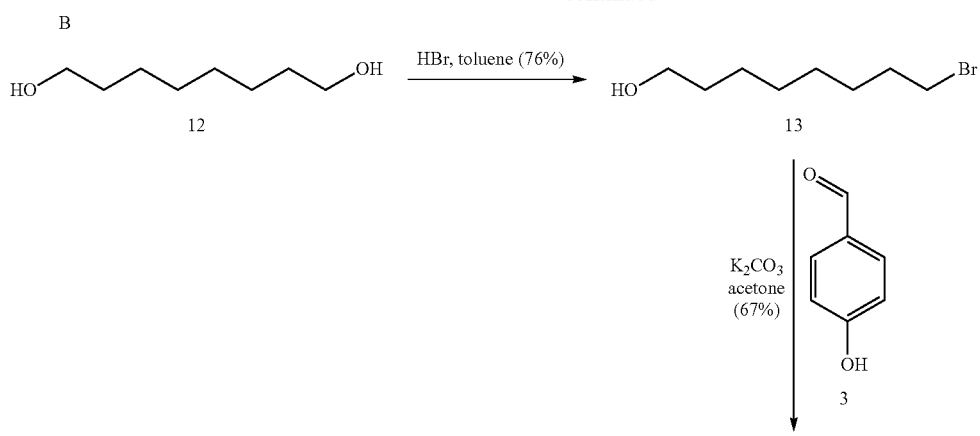
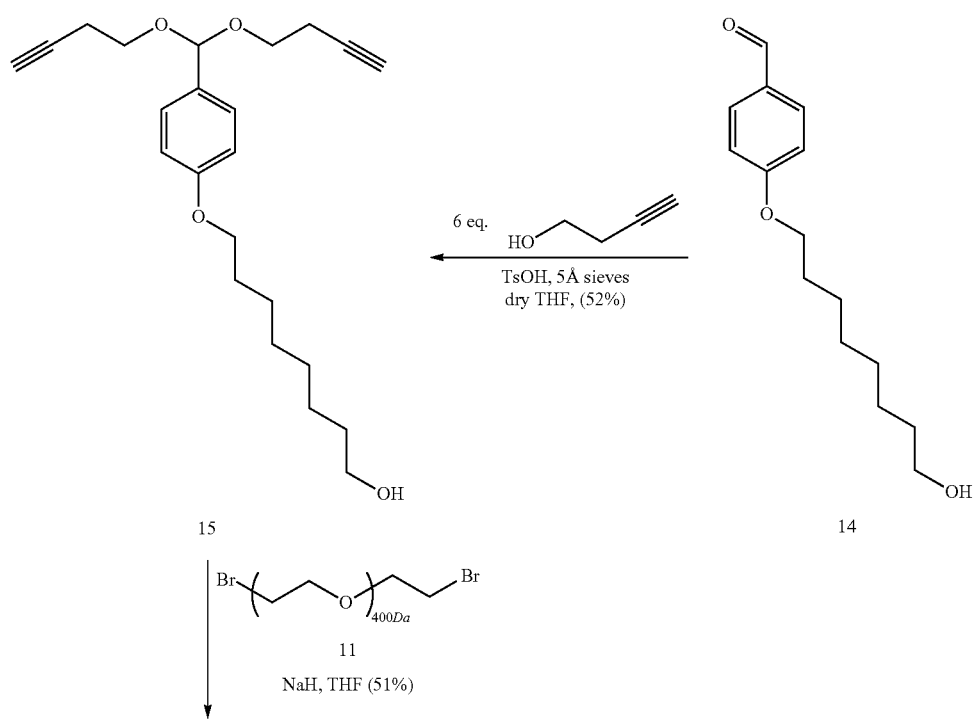

97
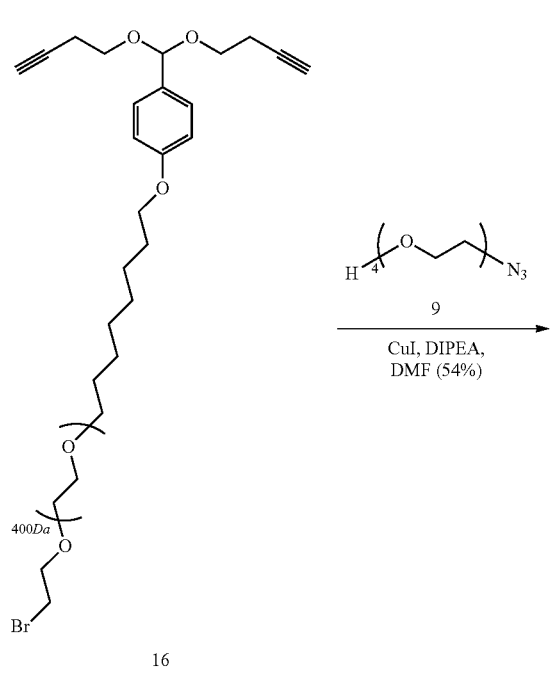
16
98
-continued
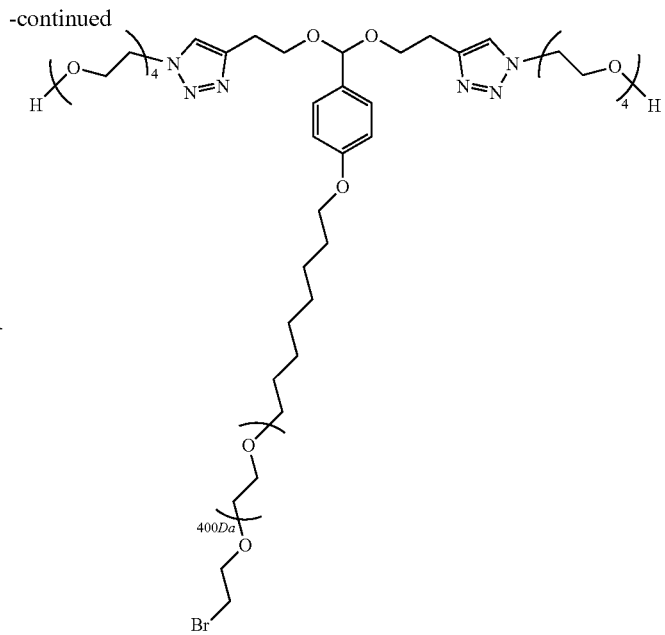
17
C)
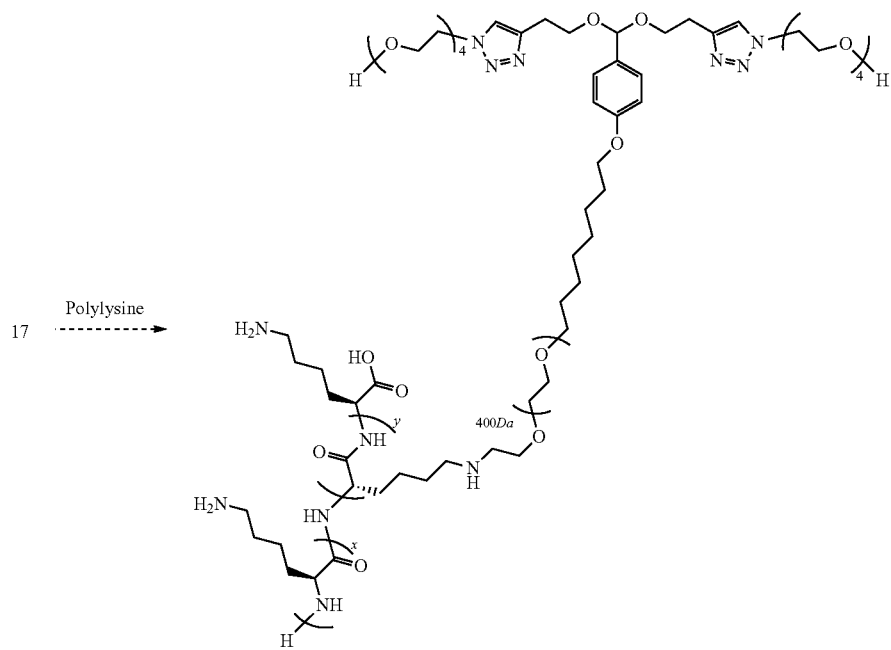
2

Scheme 3

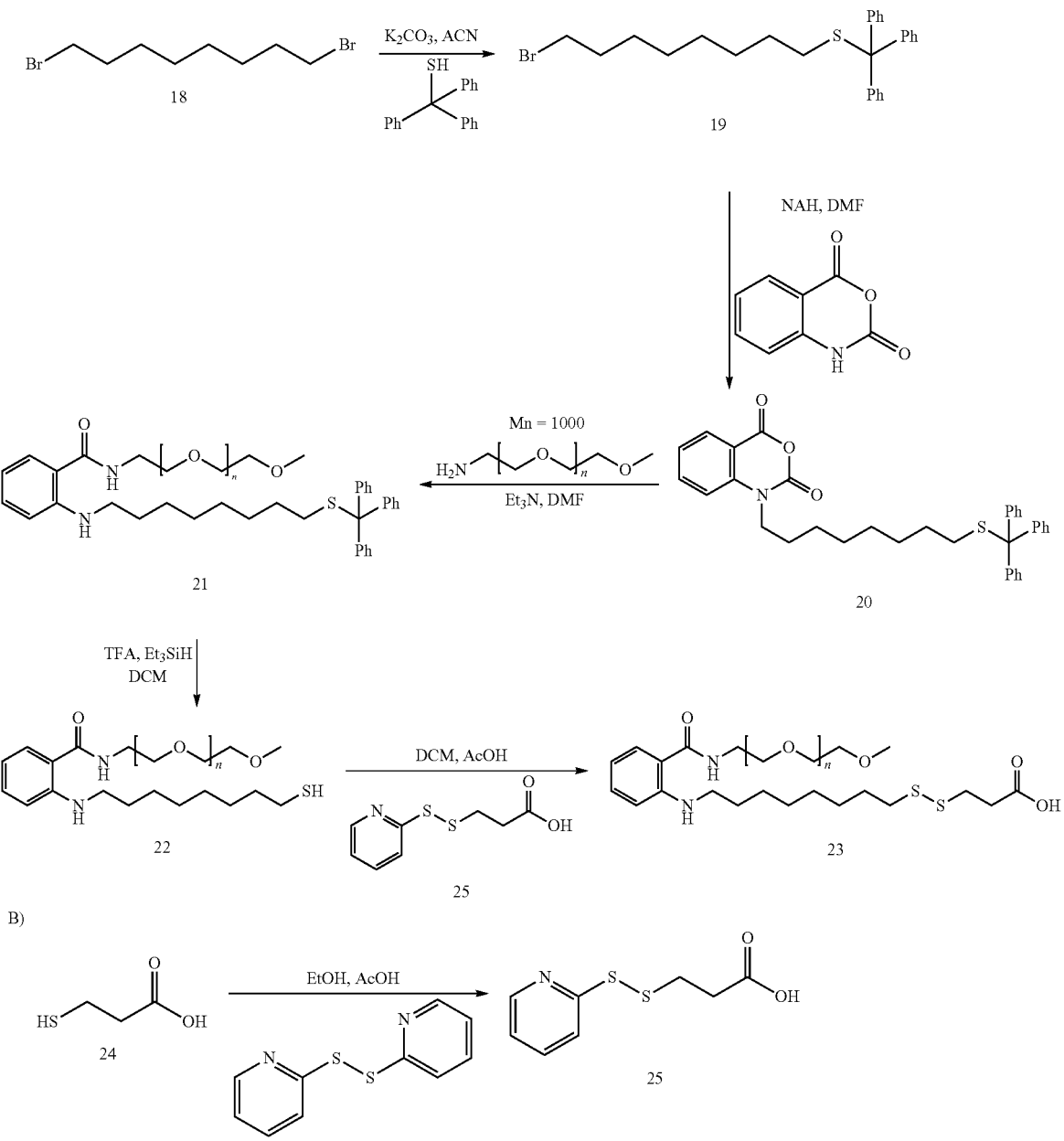

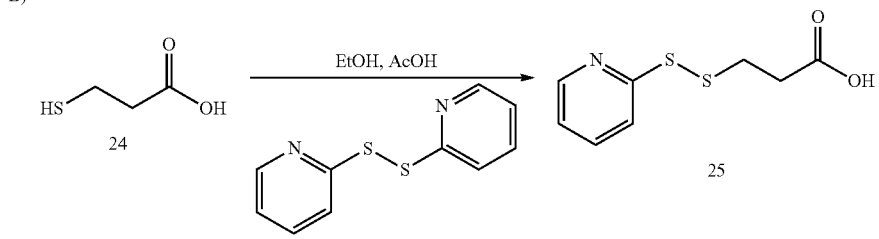

Scheme 1 shows an exemplary procedure for synthesizing an endosomal disruptor that includes nucleophilic conjugation of an aryl-containing group to a hydrophobic tail, e.g. by reaction of a hydroxy group and an alkyl bromide, conjugation through formation of an acetal, nucleophilic conjugation with a hydrophilic tail, and a "click" conjugation with hydrophilic masking groups.

Scheme 2 shows an exemplary procedure for synthesizing an endosomal disruptor that includes mono-bromination of a bis-hydroxy molecule, nucleophilic conjugation, conjugation through formation of an acetal, nucleophilic conjugation with a hydrophilic tail, a "click" conjugation with hydrophilic masking groups, and nucleophilic conjugation with a chemoselective tag.

Scheme 3 shows an exemplary procedure for synthesizing an endosomal disruptor that includes nucleophilic conjugation, a second nucleophilic conjugation, conjugation with a polyethylene glycol group containing molecule, conversion to a thiol group, and conjugation through formation of a disulfide bond.

Figure 13:
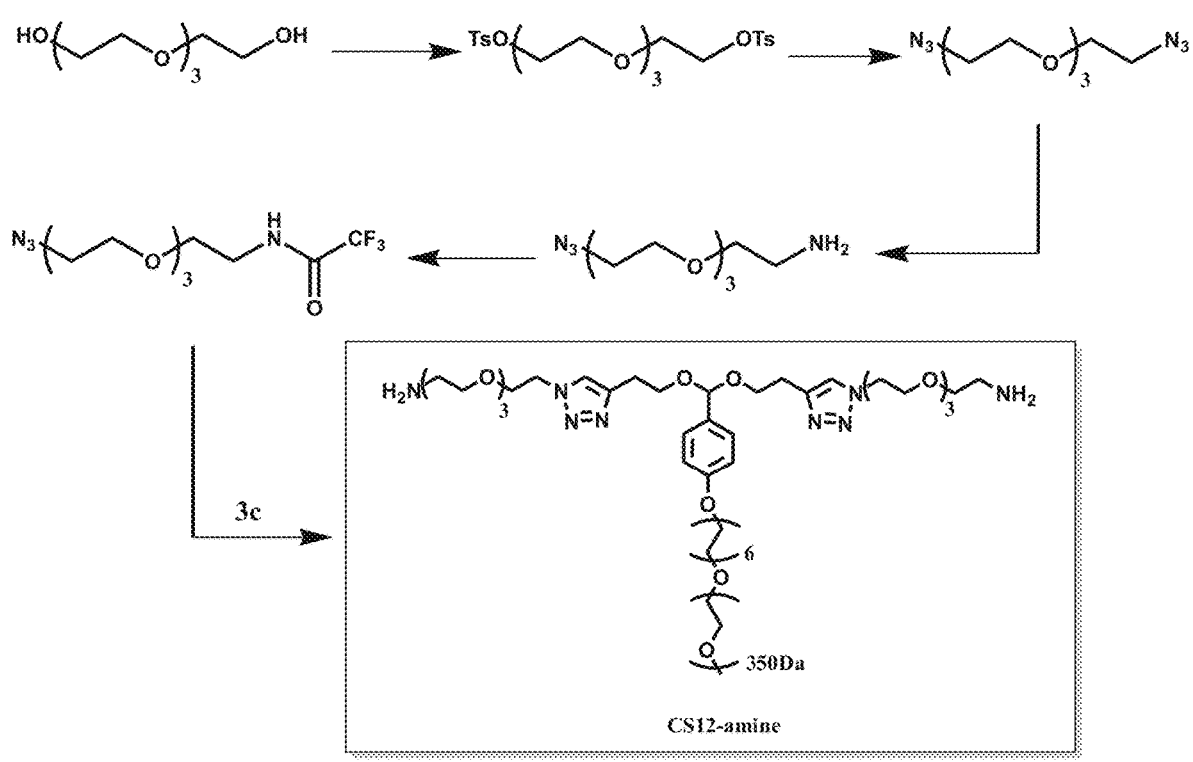
FIG. 13 illustrates the chemical synthesis of endosomal disruptor compound CS12-diamine.

FIG. 13 shows an additional exemplary procedure for synthesizing an endosomal disruptor, CS12-amine, that includes tosylation of a bis-hydroxyl compound, azidation, conversion of one azide group to an amine group, protection of the amine group, conjugation with endosomal disrupting surfactant through a "click" chemistry reaction, and deprotection of the amino group.

Synthesis of Endosomal Disruptors

Exemplary endosomal disruptors were synthesized according to Scheme 1, Scheme 2 or Scheme 3. With reference to Scheme 1, the alkyl chain or linker of compound 6 was prepared by alkylation of alcohol 3 with 1,8-dibromooctane to afford bromide 4. The aldehyde was then masked as the acetal 5, and subsequent treatment with poly(ethylene glycol) (PEG) afforded compound 6. Compound 6 was then subjected to an azide-alkyne cycloaddition reaction with azide 9 to afford the exemplary endosomal disruptor 1.

Chemical acronyms used in any of Schemes 1 to 3 are generally known in the art, by way of example, DMF, dimethylformamide; DIPEA, N,N-diisopropylethylamine; THF, tetrahydofuran; TEA, triethylamine; DCM, dichloromethane; ACN, acetonitrile; and TFA; trifluoroacetic acid.

With reference to Scheme 2, the alkyl chain or linker of compound 17 was prepared by alkylation of alcohol 3 with hydroxyl bromooctane 13 to obtain the primary alcohol 14. The aldehyde was masked as the acetal 15, and subsequent treatment with Br-PEG$_{400}$-Br (11) afforded the alkyl bromide 16. Compound 16 was then subjected to an azide-alkyne cycloaddition reaction with azide 9 to afford the alkyl bromide 17. The bromide functionality in compound 17 may then be used as a handle for further modification. For example, compound 17 may be treated under conditions to achieve attachment of a polycation such as polylysine to afford derivative 2.

With reference to Scheme 3, thiol 19 was prepared by mono-substitution of dibromide 18 with triphenylmethane thiol. Bromide 19 was then substituted with isatoic anhydride to obtain intermediate 20. Treatment of isatoic anhydride derivative 20 with an amine (e.g. a PEG substituted amine) effects ring-opening of the isatoic anhydride moiety to provide intermediate 21. Trityl deprotection with TFA furnishes thiol 22, which is subsequently treated with disulfide 25 to afford the exemplary endosomal disruptor 23 (also referred to herein as compound 3).

Example 2

Hemolysis Assay

In order to determine the hemolytic effect of the subject endosomal disruptors, exemplary compounds of the present disclosure were subjected to a standard hemolysis assay. To this end, compound 1 in phosphate buffered saline (PBS) (pH 7.4 or 6.0) (100 μL) was added to a microcentrifuge tube. 2% red blood cells (RBCs) (50 μL) was then added and the sample was incubated for 45 minutes at 37° C. The sample was then centrifuged and the absorbance was measured at 541 nm.

The results of the assay are illustrated in FIG. 1A, which shows that compound 1 exhibits pH-dependent hemolytic activity. At pH 6.0 (i.e. acidic pH), about 100% hemolysis by compound 1 was observed at concentrations of about 1.5 mM or greater. The hemolytic activity of compound 1 measures hemoglobin release as an indicator of membrane disruption. At acidic pH, compound 1 is undergoing the following hydrolysis reaction to provide the hydrophobic endosomal disruption compound 1A. Without being bound to any particular theory, the inventors have discovered that hydrolysis of the acetal group triggers endosomal disruption, thus allowing cytosolic release of any co-delivered therapeutics.

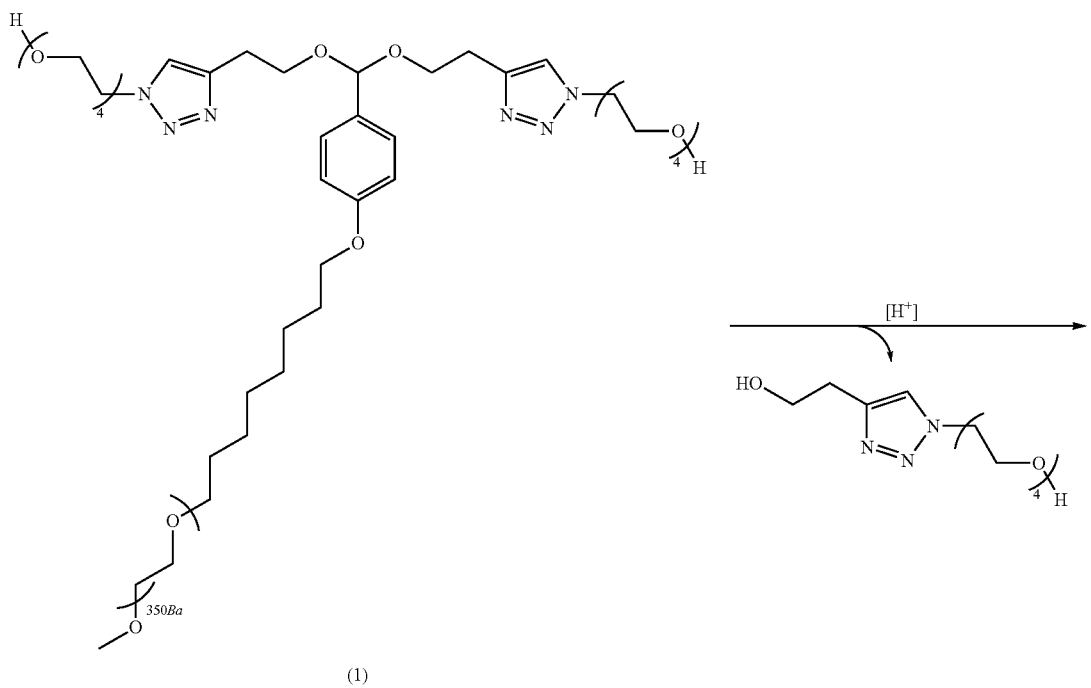

(1)

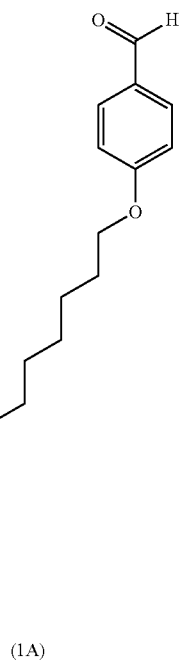

(1A)

By contrast, at pH 7.4 (i.e. neutral pH) the acetal group was not hydrolyzed and hemolysis by compound 1 was not observed.

In a similar manner, hemolysis of compound 3A was measured. At acidic pH (e.g. at conditions in the endosomal compartment) glutathione reduction cleaves the disulfide bond in compound 3 to afford the endosomal disrupting surfactant 3A, as shown below and further illustrated in FIG. 1B.

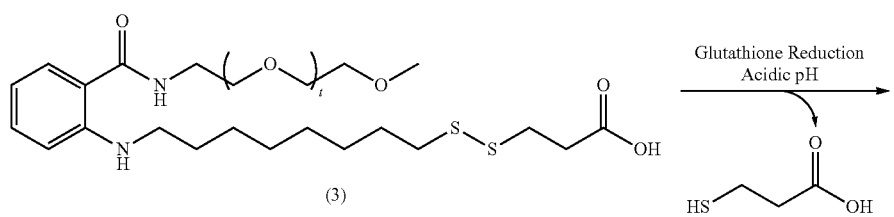

(3)

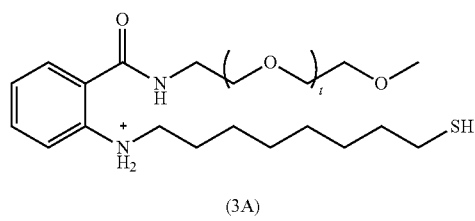

(3A)

Figure 1C:
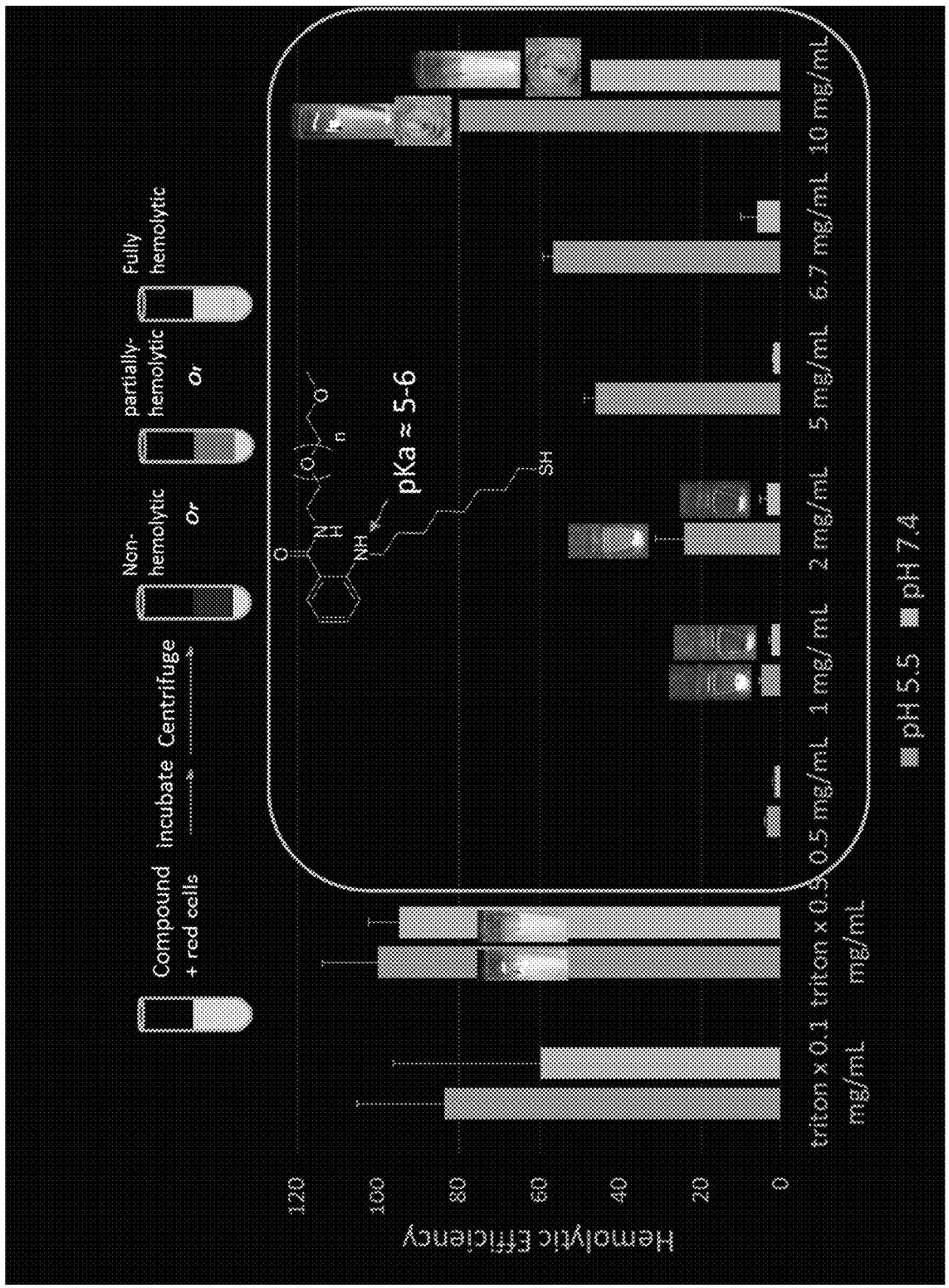

Compound 3A was subjected to a standard hemolysis assay. The results of the hemolysis assay are illustrated in FIG. 1C, which shows that compound 3A exhibits pH-dependent hemolytic activity. At pH 5.5 (i.e. acidic pH), greater hemolytic efficiency by compound 3A was observed at concentrations of 0.5 mg/mL up to 10 mg/mL. In addition, greater hemolytic efficiency was observed at increased concentrations of compound 3A at both pH 5.5 (i.e. acidic pH) and pH 7.4 (i.e. neutral pH). For example, at a concentration of 10 mg/mL full hemolysis by compound 3A was observed.

Example 3

Hydrolysis Assay

To determine if the rate of hydrolysis fits with the endosomal pathway, compound 1 of the present disclosure was subjected to kinetic studies to determine if the hydrolysis of the acetal group was pH dependent. To this end, the half-life for the acetal hydrolysis of compound 1 was measured from a pH of 3.5 to 7.4.

Figure 2:
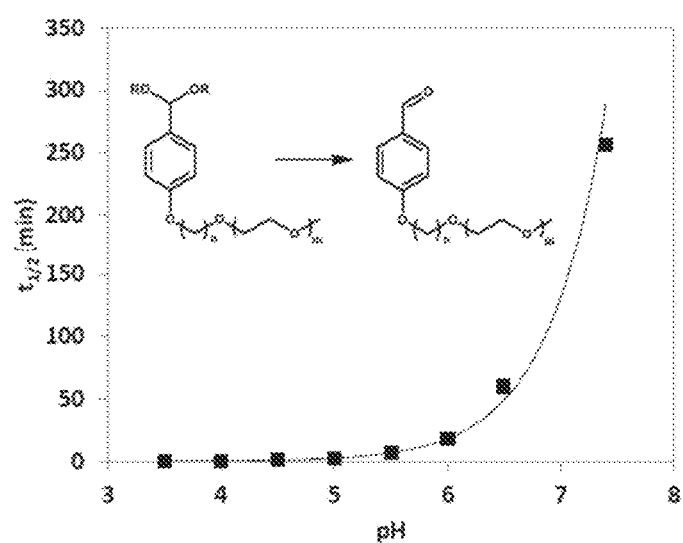
FIG. 2 illustrates the rate of hydrolysis of an exemplary endosomal disruptor.

FIG. 2 shows the results of the hydrolysis assay. With reference to FIG. 2, the kinetic studies confirmed that the hydrolysis reaction was pH dependent with an observed half-live of greater than 4 hours at pH 7.4 and half-lives of 2.5 min or less observed at a pH of 5.0 or less. Without being bound to any particular theory, in order to fit with the endosomal pathway, the acetal group may hydrolyze in the timescale of from 1 to 20 minutes at a pH of about 5. Thus, the observed rate of hydrolysis for compound 1 at pH 5.0 fits with the endosomal pathway.

Example 4

Cytotoxicity in Vitro Studies

Figure 3:
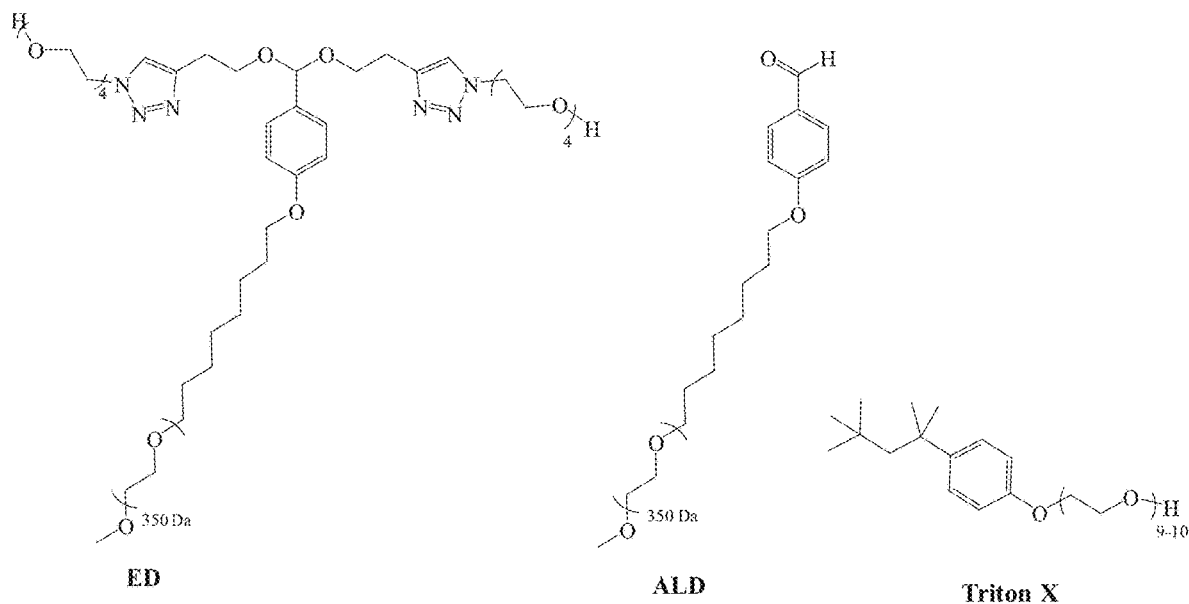
FIG. 3 illustrates the cytotoxicity of a masked and unmasked exemplary endosomal disruptor as compared to Triton X non-ionic detergent.

A cytotoxicity assay was carried out to compare the cytotoxicity in HEK293T cells of compound 1, the hydrophobic endosomal disruptor compound 1A and the known surfactant Triton X. The table exhibited in FIG. 3 shows that the hydrolyzed product 1A exhibits increased cytotoxicity in HEK293T cells as compared to compound 1 ($CC_{50}$ of 0.33 mM and 8.5 mM respectively). However, both compounds 1 and 1A exhibit decreased cytotoxicity in HEK293T as compared to Triton X (CC50 of 0.059 mM).

Example 5

Model Study with Saporin

Figure 4:
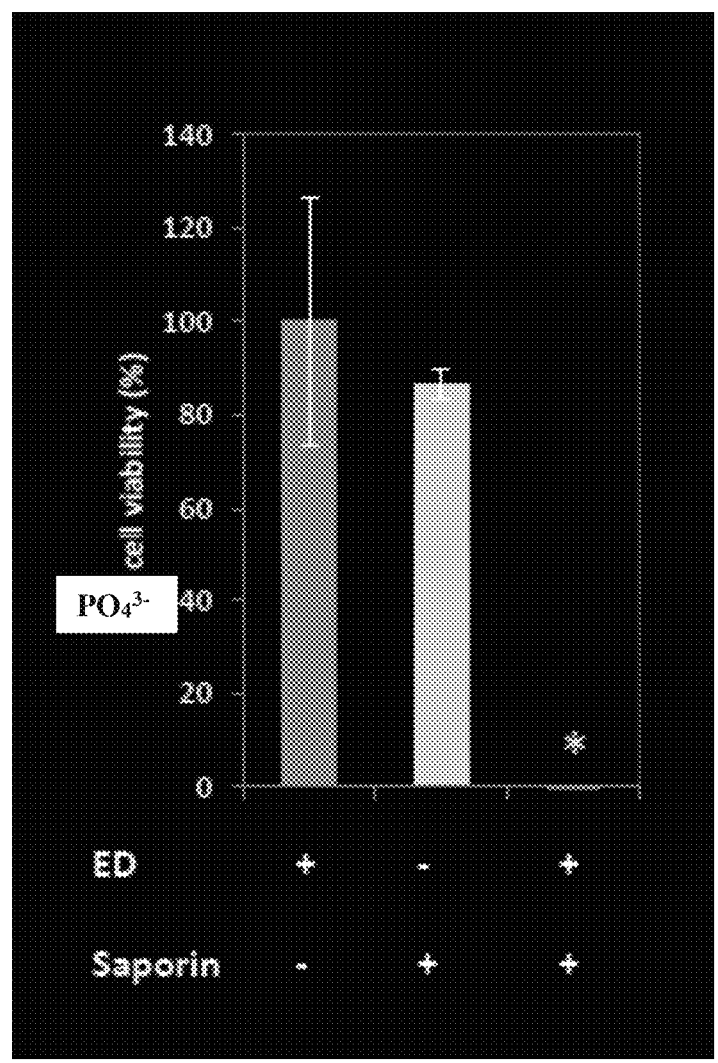
FIG. 4 illustrates that an exemplary endosomal disruptor increases Saporin toxicity in HEK293T cells.

Protein delivery was demonstrated using Saporin, a ribosome inactivation protein that has no mechanism of endosomal disruption (*Nat Chem* 2017, 9:nchem.2779), and its toxic effect is therefore dependent on induced cytosolic delivery. To this end, upon addition of compound 1 (5 mg/mL) to Saporin (10 µg/mL) in HEK293T cells, complete cell death was observed. By contrast, no cell death was observed in HEK293T cells treated with only Saporin or only compound 1 (results illustrated in FIG. 4).

Example 6

Model Study with DNA

Figure 5A:
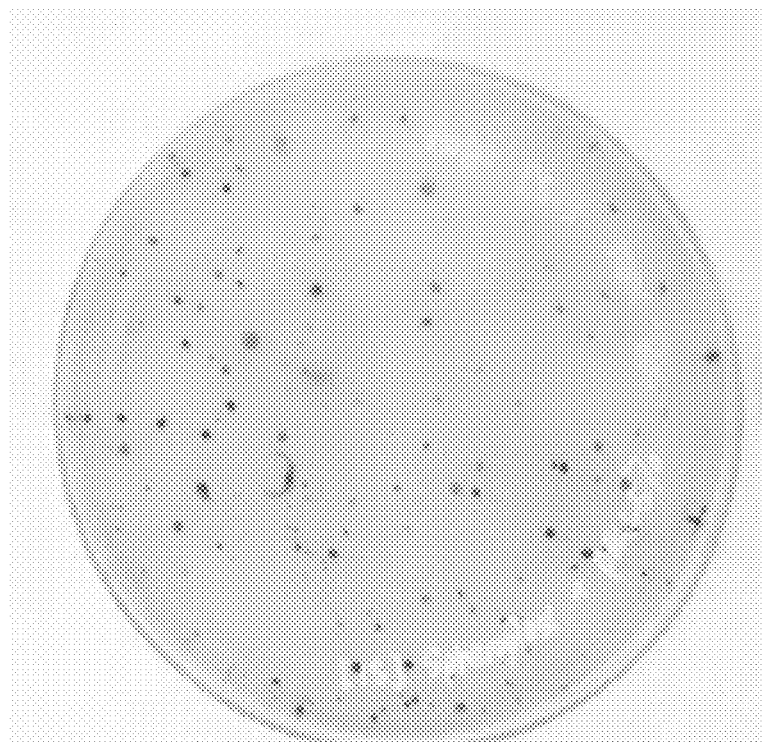
FIG. 5A-5B.
Figure 5B:
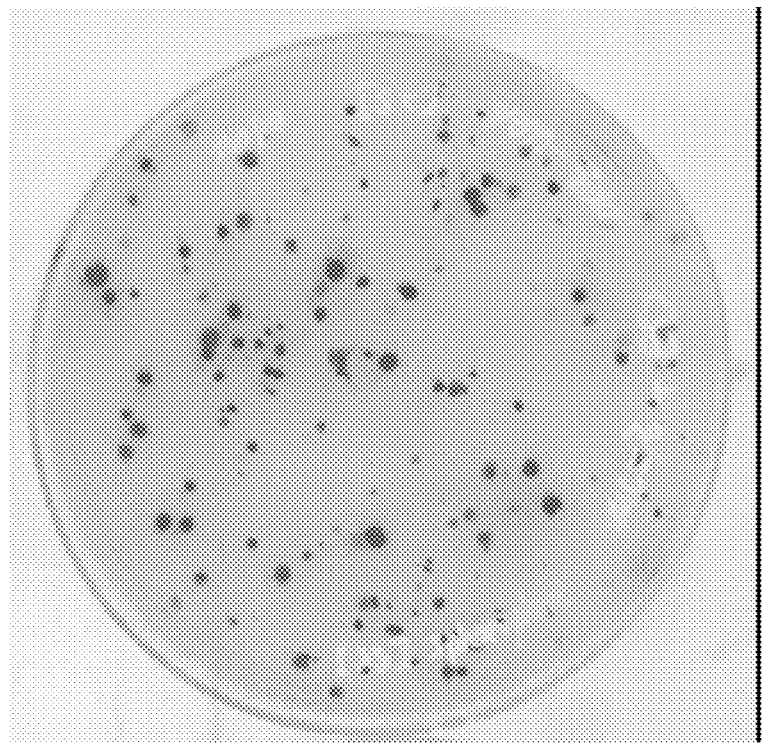

Nucleic acid delivery was investigated with DNA in yeast spheroplasts. It was observed that Compound 1 raises transformation efficiency in yeast spheroplasts. The results are illustrated in FIG. 5A and FIG. 5B. FIG. 5A, illustrates yeast spheroplasts with DNA in the absence of an exemplary endosomal disruptor; and FIG. 5B illustrates yeast spheroplasts with DNA in combination with an exemplary endosomal disruptor.

Example 6

Cas9 RNP Delivery with Lipofectamine in Vitro

Figure 9:
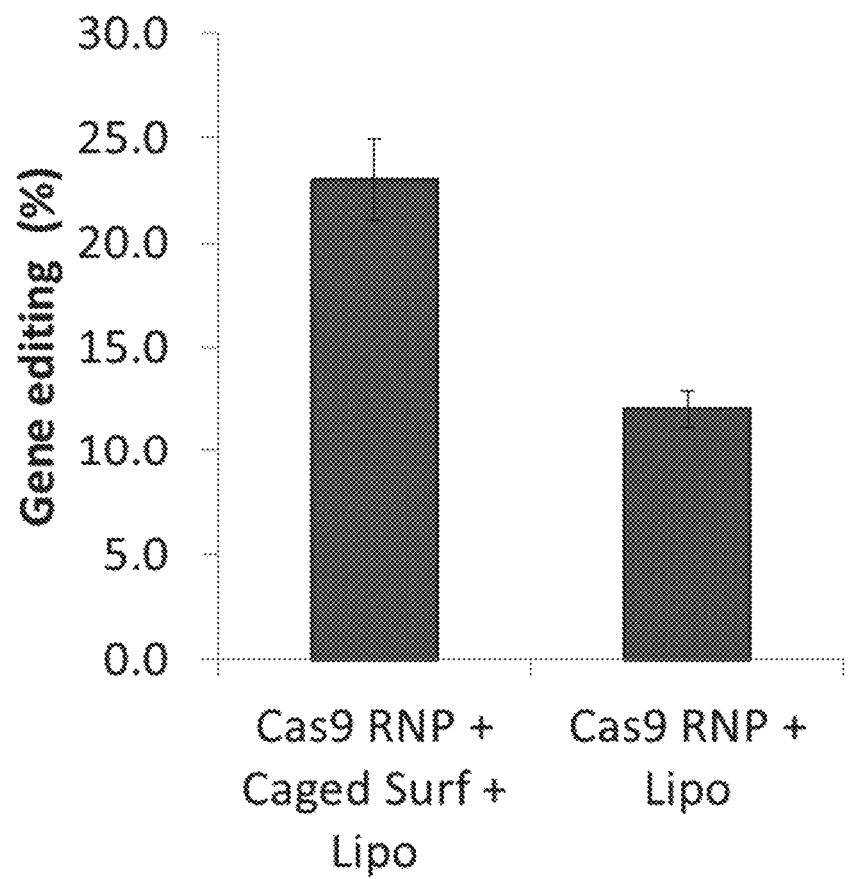
FIG. 9 illustrates the percentage of gene editing that occurred following delivery of Cas9 ribonucleoprotein (RNP) with lipofectamine transfection reagent in vitro with and without endosomal disruptor compound.

Delivery of Cas9 ribonucleoprotein (RNP) with lipofectamine to cells in vitro with and without endosomal disruptor compound was investigated. Green fluorescent protein (GFP) was used as an indicator for whether gene editing occurred. It was found that by adding an endosomal disruptor compound ("Caged Surf"), the measured amount of gene editing increased (results illustrated in FIG. 9).

Example 7

Hemolytic Efficacy with Different Endosomal Disruptor Compounds

Figure 10:
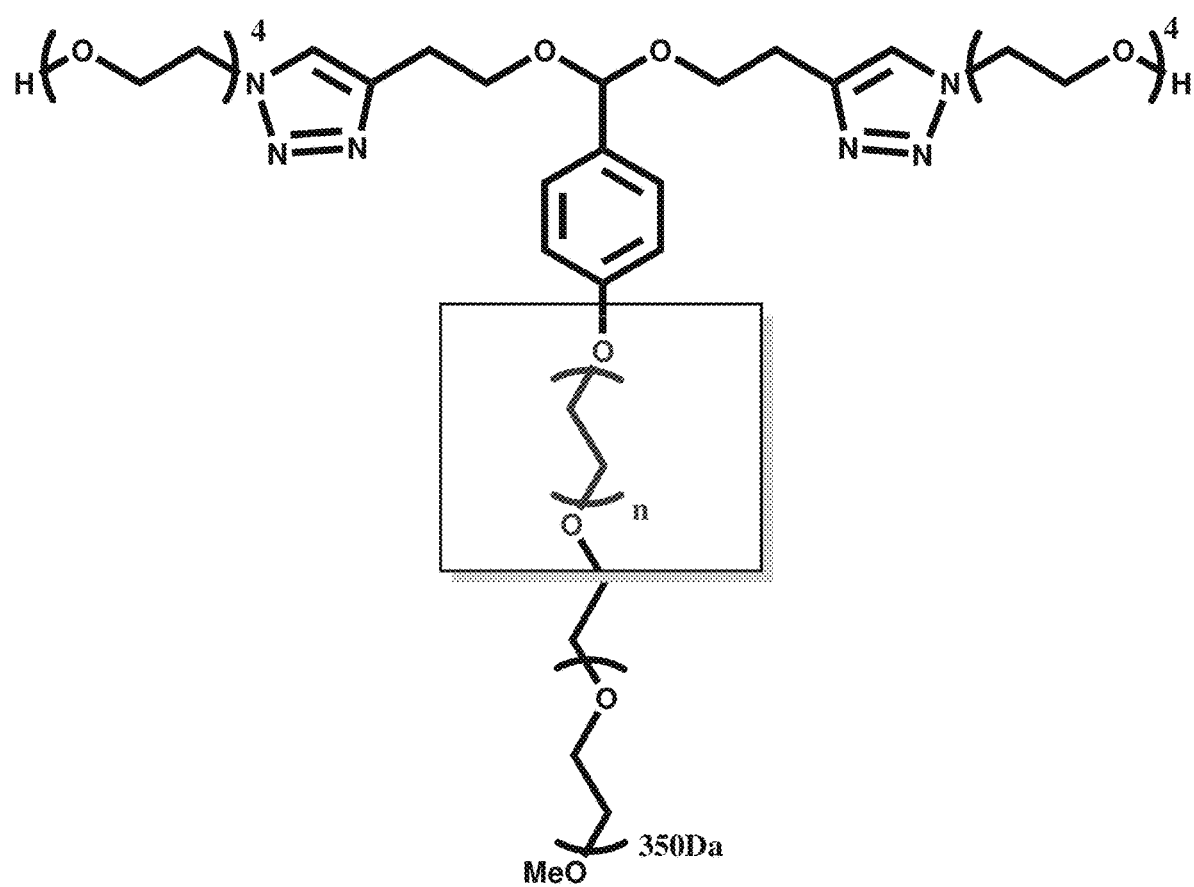
FIG. 10 illustrates the chemical structure of endosomal disruptor compounds used to test the effect of different lengths of hydrophobic tails on hemolytic efficacy.

A structure-activity study was performed in order to assess the effect of the chemical structure of the endosomal disruptor compound on hemolytic efficiency. In particular, endosomal disruptor compounds were synthesized wherein the number of adjacent —($CH_2CH_2$)— groups in the hydrophobic tail was 4, 5, 6, or 8 (i.e. n=4, 5, 6, or 8 as shown in FIG. 10), referred to as the C8, C10, C12, and C16 compounds, respectively.

Figure 11:
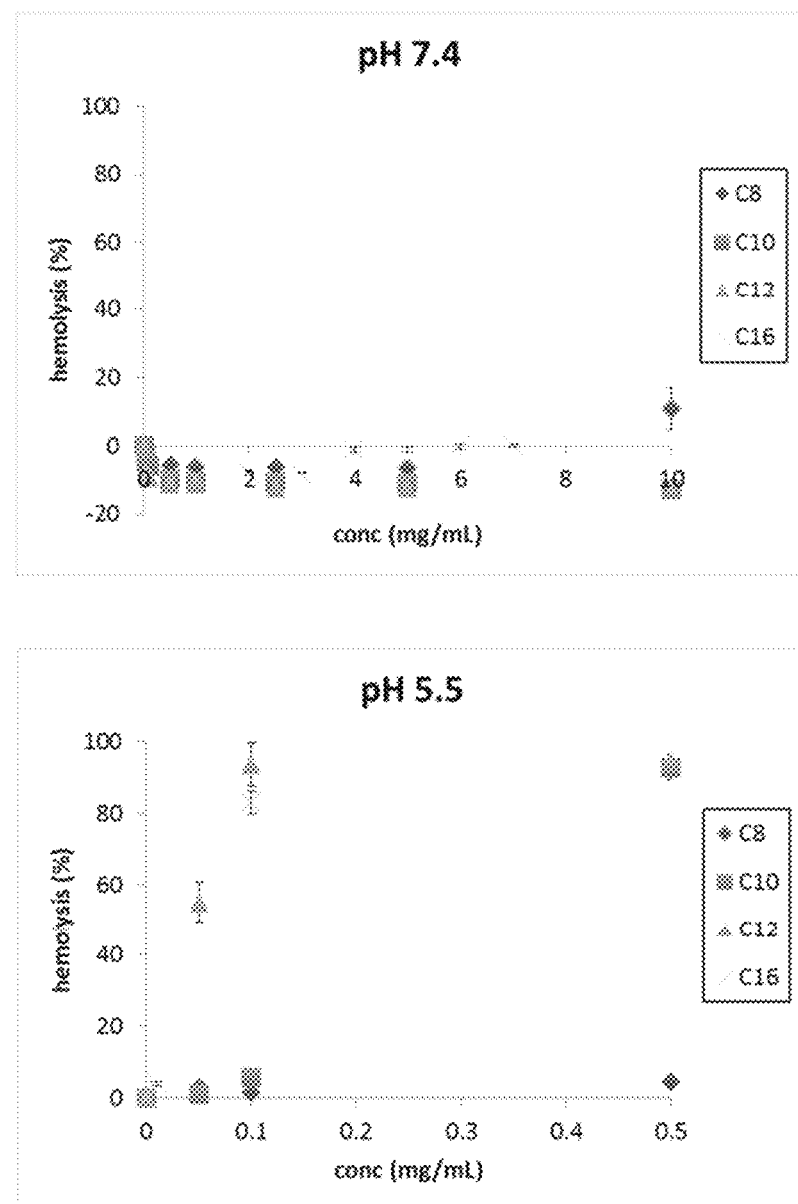
FIG. 11 illustrates the hemolytic efficiency of the endosomal disruptor compounds of FIG. 10 at pH 5.5 and 7.4.

Hemolytic efficiency was measured at pH 5.5 and pH 7.4 for the C8, C10, C12, and C16 compounds, showing that % hemolysis was significantly higher in the pH 5.5 experiments than in the pH 7.4 experiments (FIG. 11). In addition, the C12 and C16 compounds caused greater hemolysis than the C8 and C10 compounds, with C8 showing the lowest hemolysis.

Example 8

Effect of pH on Rate of Rate of Hydrolysis of Endosomal Disruptor Compounds

Figure 12:
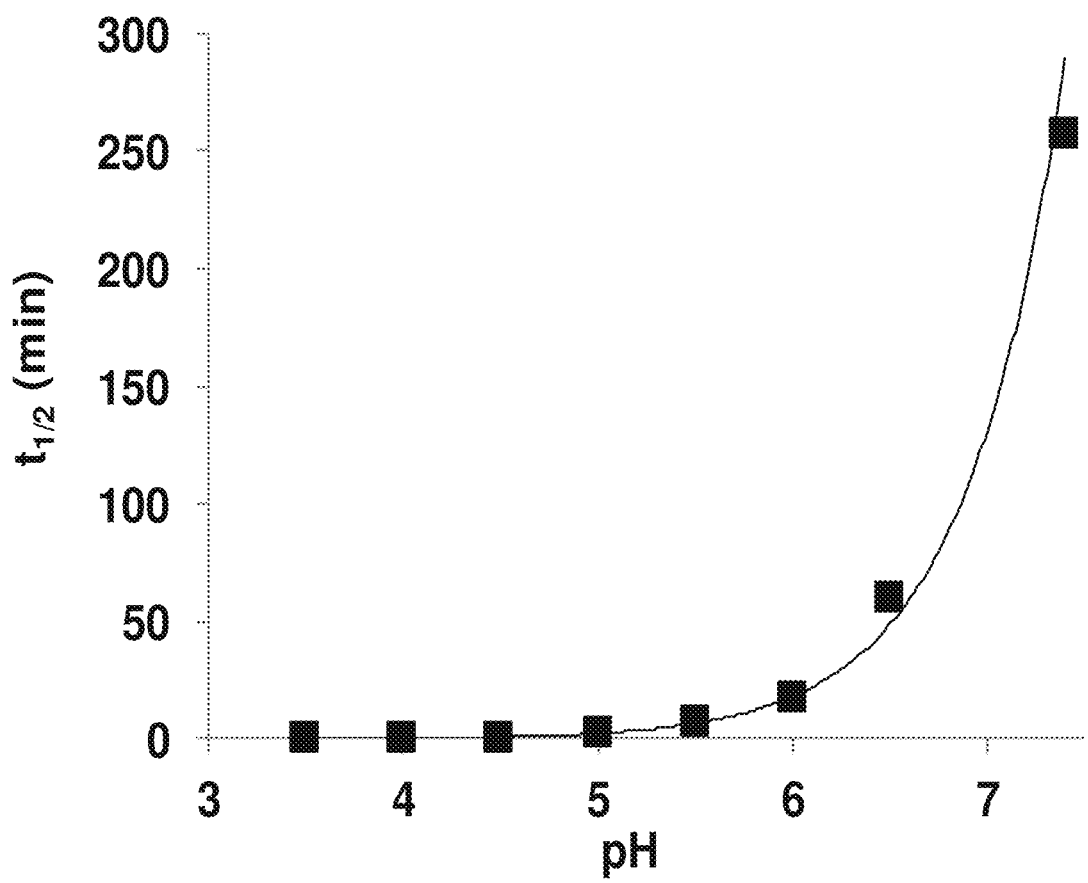
FIG. 12 illustrates the effect of pH on the rate of hydrolysis of endosomal disruptor compounds.

In view of the observed pH effect on hemolysis described above, the effect of pH on the rate of hydrolysis of endosomal disruptor compounds was investigated. The hydrolysis rate of the endosomal disruptor compounds was measured via absorption spectroscopy, at a 50 µg/mL concentration at 37° C. in aqueous buffer. FIG. 12 demonstrates that the endosomal disruptor compounds hydrolyze to release their PEG chains in a pH sensitive manner They have a $k_{2nd}$=261 $s^{-1}M^{-1}$, with a hydrolysis half-life of 4 minutes at pH 5.0 and 4 hours at pH 7.4.

Example 9

Synthesis of the Endosomal Disruptor Compound CS12-Diamine

The endosomal disruptor compound CS12-diamine was synthesized as shown in FIG. 13. As used herein, "diamine" in "CS12-diamine" refers to the presence of two amino groups in the CS12-diamine endosomal disruptor compound.

Example 10

Effect of pH on the Recovery of Free DNA from Endosomes

Figure 14:
FIG. 14 illustrates the effect of pH on the recovery of DNA from endosomes.

The effect of pH on the recovery of DNA from endosomes was investigated. The endosomal disruptor compound CS12-diamine was contacted with 45-bp dsDNA for 1 hour, after which the pH was adjusted to either 7.0, 6.4, or 6.0. A gel analysis was then performed to assess the amount of dsDNA recovered from the endosomes. As shown in FIG. 14, lower pH values resulted in increased recovery of free DNA. The lanes of FIG. 14 correspond, from left to right, to the samples of pH 7.0, pH 6.4, pH 6.0, DNA in the absence of CS12-diamine, and ladder.

Example 11

Effect of N/P Ratio on DNA Retention

The effect of the N/P ratio (i.e. the ratio of moles of the amine groups of the endosomal disruptor to the moles of the phosphate groups of DNA) on DNA retention was investigated by agarose gel analysis. First, a 10 mg/mL endosomal disruptor solution was made by mixing 1.0 mg of the endosomal disruptor compound, 1.5 µL of 6 M NaOH and 8 µL of 1,4-dioxane, giving a roughly 1.2 M NaOH solution. This solution was then allowed to sit at room temperature for 2 hours, after which 90 µL of phosphate buffer was added and the pH was checked. Next, samples were made by mixing the endosomal disruptor solution with a 50 ng/µL GFP-plasmid ("DNA") solution and phosphate buffer according to Table 2. After mixing the DNA and endosomal disruptor solutions for sample 8, 5 µL of 0.25 HCl was also added to sample 8.

TABLE 2

Table 2 lists the volumes of DNA solution, endosomal disruptor solution, and phosphate buffer used to create the samples described in Example 11.

| sample | DNA (µL) | Endosomal Disruptor (µL) | Phosphate Buffer (µL) | N/P Ratio | Endosomal Disruptor Concentration (mg/mL) |
|---|---|---|---|---|---|
| 1 | 5.0 | 5.0 | 0.0 | 111 | 5.0 |
| 2 | 5.0 | 2.5 | 2.5 | 56 | 2.5 |
| 3 | 5.0 | 1.0 | 4.0 | 22 | 1.0 |
| 4 | 5.0 | 0.5 | 4.5 | 11 | 0.5 |
| 5 | 5.0 | 0.2 | 4.8 | 4 | 0.2 |
| 6 | 5.0 | 0.0 | 5.0 | 0 | 0.0 |
| 7 | ladder | — | — | — | — |
| 8 | 5.0 | 5.0 | 0.0 | 111 | 5.0 |

The samples were allowed to sit for 1 hour and then an agarose gel analysis was performed using 1% agarose. The agarose gel analysis was performed by adding 2 µL of loading dye to the mixtures and then running the gel. The results of the agarose gel analysis are shown in FIG. 15. The relative area values shown in FIG. 15 were calculated by measuring the relative area of the visible bands within $R_f=0.18$ to $R_f=0.21$ regions. FIG. 15 shows that higher relative areas were observed at lower N/P ratios, whereas lower relative areas were observed at higher N/P ratios.

Example 12: dsDNA Retention with a 1 kb dsDNA

Figure 16:
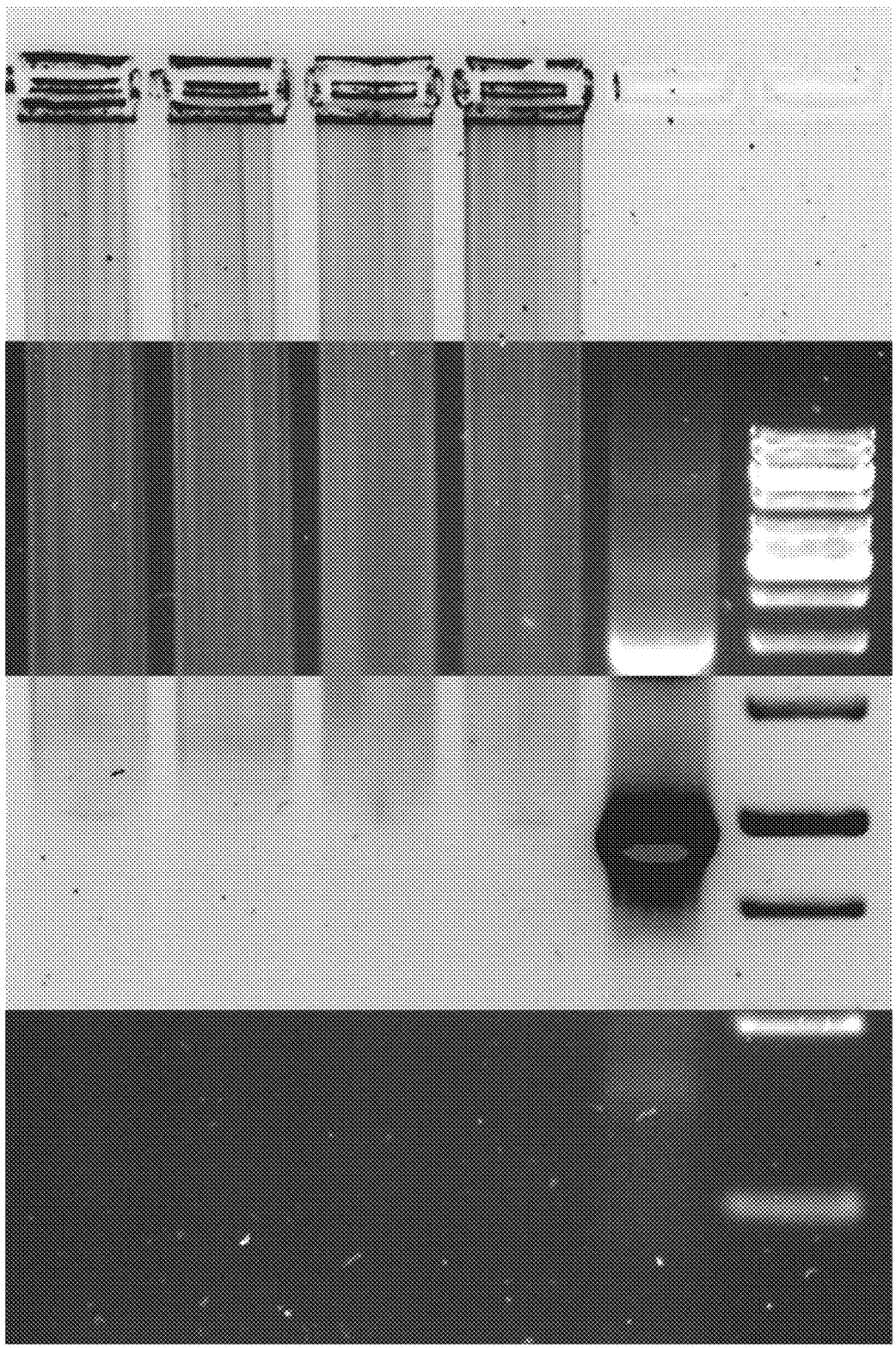
FIG. 16 illustrates results regarding dsDNA retention by endosomal disruptor compound CS12-diamine with a 1 kb dsDNA.

The diamino-aged endosomal disruptor compound CS12-diamine was treated with 1 kb dsDNA with N/P ratios of 40, 32, 24, and 16. Agarose gel analysis showed that larger DNA molecules require lower N/P ratios to be retained, as shown in FIG. 16. In FIG. 16, the lanes from left to right correspond to N/P of 40, N/P of 32, N/P of 24, N/P of 16, DNA only, and ladder.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

The patent contains a lengthy sequence listing. A copy of the sequence listing is available in electronic form from the USPTO web site (https://seqdata.uspto.gov/?pageRequest=docDetail&DocID=US12059407B2). An electronic copy of the sequence listing will also be available from the USPTO upon request and payment of the fee set forth in 37 CFR 1.19(b)(3).

What is claimed is:

1. An endosomal disruptor of the formula (I):

   (I)

wherein:
M is a hydrophilic masking group;
Z is a cleavable linker capable of cleavage with an endosome to release M and produce an endosomal disrupting surfactant;
A is a masked hydrophobic group comprising:
(a) a cyclic group selected from:

(A1)

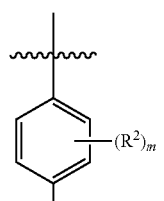

(A2)

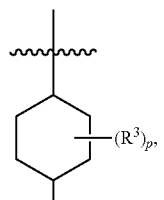

(A3)

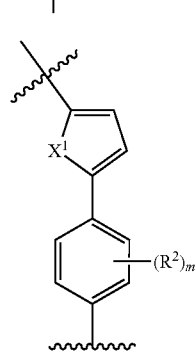

, and (A4)

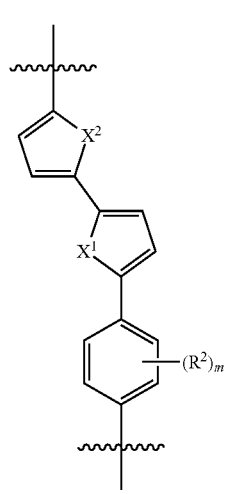

wherein:
$R^2$ and $R^3$ are each independently selected from the group consisting of OH, alkyl, substituted alkyl, alkenyl, substituted alkenyl, alkoxy, substituted alkoxy, —$OCF_3$, halogen, amine, substituted amine, amide, azide, heterocycle and substituted heterocycle;
$X^1$ and $X^2$ are each independently selected from a carbon atom and a heteroatom selected from S, O and N;
m is an integer from 0 to 4; and
p is an integer from 0 to 8; and
(b) a hydrophobic chain comprising:
a linear or branched hydrophobic chain selected from, alkyl, alkenylene, alkynylene, arylene, alkarylene, aralkylene, alkoxy and alkamine; or
(c) a hydrophobic chain selected from:

(B1)

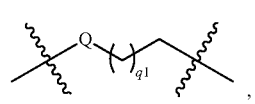

, (B2)

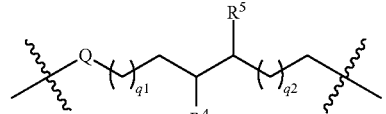

, and (B3)

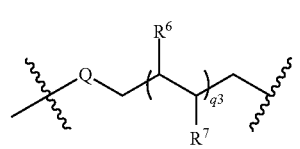

, wherein:
$R^4$, $R^5$, $R^6$ and $R^7$ are each independently selected from alkyl and substituted alkyl; and
q, $q^1$, $q^2$ and $q^3$ are each independently an integer from 1 to 20;
T is a hydrophilic tail group; and
Y is an optional group selected from a terminal group, a linker, a chemoselective tag, a member of a specific binding pair, a linked biomolecule and a linked cell delivery agent;
or a pharmaceutically acceptable salt.

2. The endosomal disruptor of claim 1, wherein M is an inert hydrophilic masking group.

3. The endosomal disruptor of claim 1, of the formula (II):

(II)

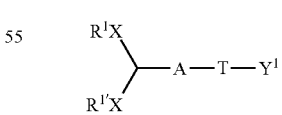

wherein:
$R^1$ and $R^{1'}$ are independently selected from alkyl, alkenyl, heterocycle, substituted heterocycle, substituted heterocycle, carbocycle, substituted carbocycle, polyethylene glycol (PEG), substituted PEG, alkyl-$Y^1$ and alkenyl-$Y^1$, wherein $Y^1$ is selected from the group consisting of, heterocycle, substituted heterocycle, heteroaryl, substituted heteroaryl, carbocycle, substituted carbocycle, polyethylene glycol (PEG), modified PEG, and wherein each $Y^1$ group is optionally substituted with one or more additional groups selected from alkyl, substituted alkyl, PEG and modified PEG;

or $R^1$ and $R^{1'}$ together with the carbon to which they are attached form a group selected from heterocycle and substituted heterocycle;

X is O or S;

A is a masked hydrophobic group comprising:

(a) a cyclic group selected from:

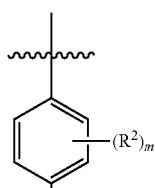
(A1)

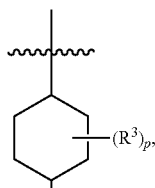
(A2)

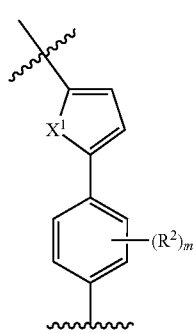
(A3)

, and

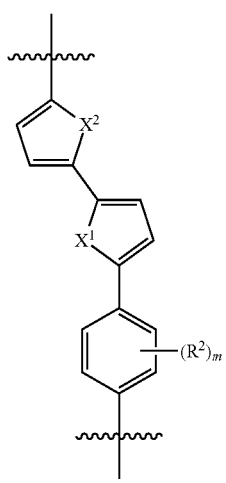
(A4)

wherein:
$R^2$ and $R^3$ are each independently selected from the group consisting of OH, alkyl, substituted alkyl, alkenyl, substituted alkenyl, alkoxy, substituted alkoxy, —OCF$_3$, halogen, amine, substituted amine, amide, azide, heterocycle and substituted heterocycle;

$X^1$ and $X^2$ are each independently selected from a carbon atom and a heteroatom selected from S, O and N;

m is an integer from 0 to 4; and
p is an integer from 0 to 8; and (b) a hydrophobic chain comprising:
a linear or branched hydrophobic chain selected from, alkyl, alkenylene, alkynylene, arylene, alkarylene, aralkylene, alkoxy and alkamine; or (c) a hydrophobic chain selected from:

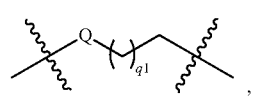
(B1)

,

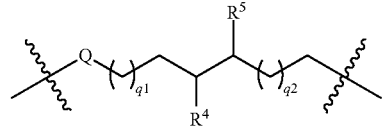
(B2)

, and

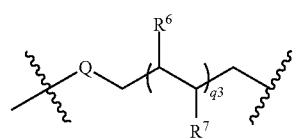
(B3)

, wherein:
$R^4$, $R^5$, $R^6$ and $R^7$ are each independently selected from alkyl and substituted alkyl; and
q, $q^1$, $q^2$ and $q^3$ are each independently an integer from 1 to 20;

T is a hydrophilic tail selected from a polyethylene glycol (PEG), a modified PEG, a oligoethyleneglycol, a phosphate, a phosphonate, a boric acid, a carboxylate, a sulfate, a sulfonate, an amine, a glycerol, a sugar, an amino acid, a substituted amino acid; and $Y^1$ is an optional group selected from a terminal group, a linker, a chemoselective tag, a member of a specific binding pair, a linked biomolecule and a linked cell delivery agent;

or a pharmaceutically acceptable salt.

4. The endosomal disruptor of claim 3, of the formula (III)

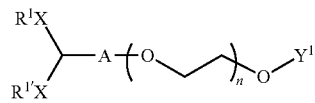
(III)

wherein:
$R^1$ and $R^{1'}$ are independently selected from alkyl, alkenyl, heterocycle, substituted heterocycle, substituted heterocycle, carbocycle, substituted carbocycle, polyethylene glycol (PEG), substituted PEG, alkyl-$Y^1$ and alkenyl-$Y^1$, wherein $Y^1$ is selected from the group consisting of, heterocycle, substituted heterocycle, heteroaryl, substituted heteroaryl, carbocycle, substituted carbocycle, polyethylene glycol (PEG), modified PEG, and wherein each $Y^1$ group is optionally substituted with one or more additional groups selected from alkyl, substituted alkyl, PEG and modified PEG;

or $R^1$ and $R^{1'}$ together with the carbon to which they are attached form a group selected from heterocycle and substituted heterocycle;

X is O or S;

A is a masked hydrophobic group comprising:
(a) a cyclic group selected from:

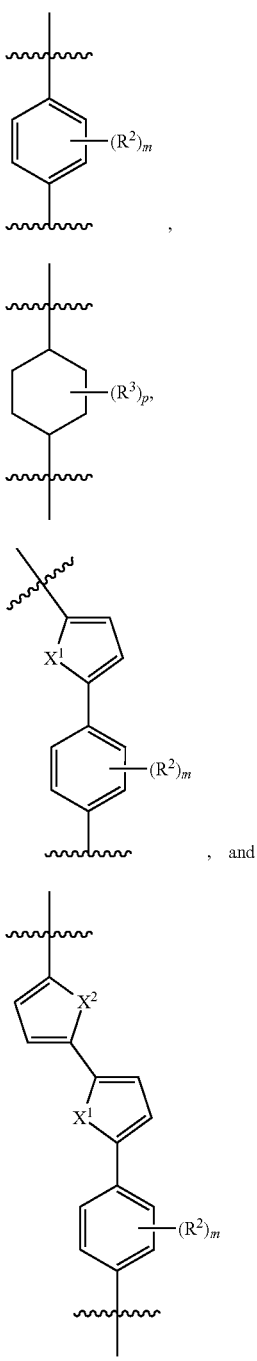

wherein:
$R^2$ and $R^3$ are each independently selected from the group consisting of OH, alkyl, substituted alkyl, alkenyl, substituted alkenyl, alkoxy, substituted alkoxy, —OCF$_3$, halogen, amine, substituted amine, amide, azide, heterocycle and substituted heterocycle;

$X^1$ and $X^2$ are each independently selected from a carbon atom and a heteroatom selected from S, O and N;

m is an integer from 0 to 4; and
p is an integer from 0 to 8; and
(b) a hydrophobic chain comprising:
a linear or branched hydrophobic chain selected from, alkyl, alkenylene, alkynylene, arylene, alkarylene, aralkylene, alkoxy and alkamine; or
(c) a hydrophobic chain selected from:

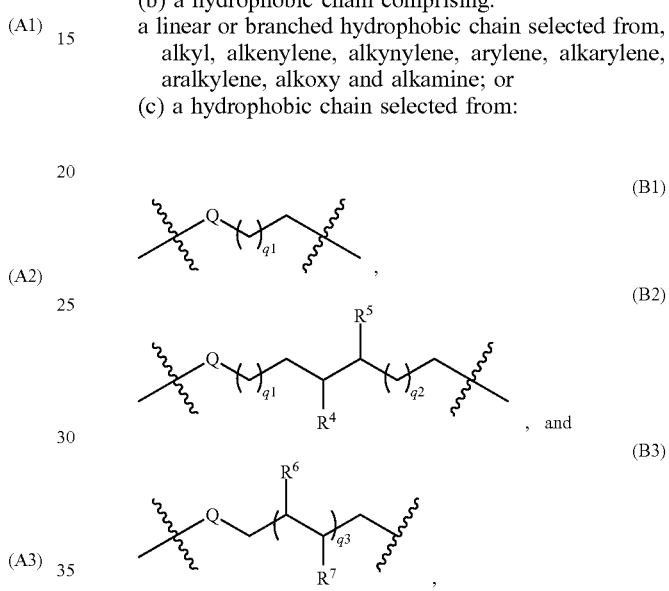

wherein:
$R^4$, $R^5$, $R^6$ and $R^7$ are each independently selected from alkyl and substituted alkyl; and
q, $q^1$, $q^2$ and $q^3$ are each independently an integer from 1 to 20;
n is an integer up to 500 Da; and
$Y^1$ is selected from a terminal group, a linker, a chemoselective tag, a member of a specific binding pair, a linked biomolecule and a linked cell delivery agent;
or a pharmaceutically acceptable salt.

5. The endosomal disruptor of claim 1, of the formula (IV):

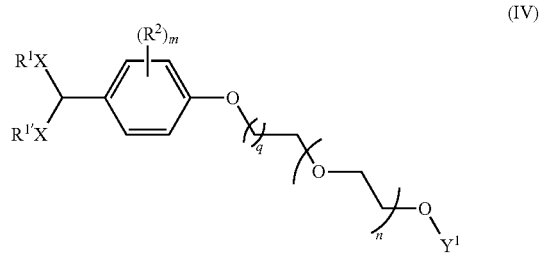

wherein:
$R^1$ and $R^{1'}$ are independently selected from alkyl, alkenyl, heterocycle, substituted heterocycle, substituted heterocycle, carbocycle, substituted carbocycle, polyethylene glycol (PEG), substituted PEG, alkyl-$Y^1$ and alkenyl-$Y^1$, wherein $Y^1$ is selected from the group consisting of, heterocycle, substituted heterocycle, heteroaryl, substituted heteroaryl, carbocycle, substituted carbocycle, polyethylene glycol (PEG), modified PEG, and wherein each $Y^1$ group is optionally substituted with one or more additional groups selected from alkyl, substituted alkyl, PEG and modified PEG;

or $R^1$ and $R^{1'}$ together with the carbon to which they are attached form a group selected from heterocycle and substituted heterocycle;

each $R^2$ are independently selected from the group consisting of OH, alkyl, substituted alkyl, alkenyl, substituted alkenyl, alkoxy, substituted alkoxy, —$OCF_3$, halogen, amine, substituted amine, amide, azide, heterocycle and substituted heterocycle;

X is O or S;

m is an integer from 0 to 4;

q is an integer from 1 to 20;

n is an integer up to 500 Da; and $Y^1$ is selected from a terminal group, a linker, a chemoselective tag, a linked biomolecule, a member of a specific binding pair, and a linked cell delivery agent; or a pharmaceutically acceptable salt.

6. The endosomal disruptor of claim 1, wherein:

(a) Y or $Y^1$ is a chemoselective tag comprising a group selected from amine and carboxylic acid; or (b) Y or $Y^1$ comprises a chemoselective tag configured to conjugate to a peptide, a protein or a polycation selected from a cationic peptide, a cationic peptide derivative, linear synthetic polymer, branched synthetic polymer, polysaccharide, natural polymer, activated dendrimer and a non-activated dendrimer.

7. The endosomal disruptor of claim 6, wherein the polycation is a cationic peptide.

8. The endosomal disruptor of claim 3, wherein:

(a) each X group is O; or (b) $R^1$ and $R^{1'}$ are both:

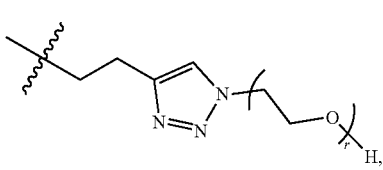

and r is an integer from 1 to 10.

9. The endosomal disruptor of claim 1, having one of the following structures:

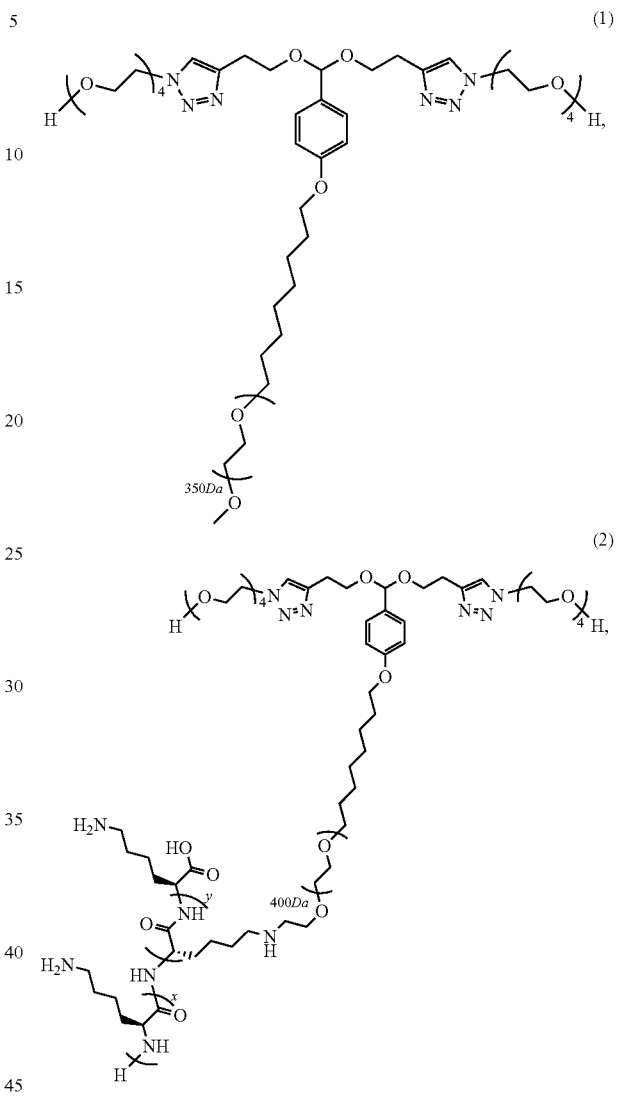

wherein x and y combined equal an integer from 25 to 30.

10. A composition comprising:
a) an endosomal disruptor of claim 1; and
b) one or more macromolecules.

11. The composition of claim 10, wherein the one or more macromolecules comprise:
i) an RNA-guided endonuclease;
ii) a guide RNA; and
iii) a donor DNA.

12. A method of delivering a macromolecule to the cytoplasm of a eukaryotic cell, the method comprising contacting the cell with a composition of claim 10.

* * * * *